US006172078B1

(12) United States Patent
Nagase et al.

(10) Patent No.: US 6,172,078 B1
(45) Date of Patent: Jan. 9, 2001

(54) QUINOLINOMORPHINANE DERIVATIVES AND MEDICINAL USE THEREOF

(75) Inventors: Hiroshi Nagase; Yoshifumi Imamura; Hiroshi Ohno; Masanobu Kaneeda; Susumu Matsuda; Yasushi Miyauchi, all of Kanagawa (JP)

(73) Assignee: Toray Industries, Inc., Tokyo (JP)

( * ) Notice: Under 35 U.S.C. 154(b), the term of this patent shall be extended for 0 days.

(21) Appl. No.: 09/194,538

(22) PCT Filed: Mar. 30, 1998

(86) PCT No.: PCT/JP98/01443

§ 371 Date: Jan. 13, 1999

§ 102(e) Date: Jan. 13, 1999

(87) PCT Pub. No.: WO98/43977

PCT Pub. Date: Oct. 8, 1998

(30) Foreign Application Priority Data

Mar. 31, 1997 (JP) .................................................. 9-081756

(51) Int. Cl.[7] ........................ C07D 515/00; A61K 31/44
(52) U.S. Cl. ............................................ 514/279; 546/37
(58) Field of Search ............................... 546/37; 514/279

(56) References Cited

FOREIGN PATENT DOCUMENTS

| | | |
|---|---|---|
| 3218313A | 9/1991 | (JP) . |
| 3223288A | 10/1991 | (JP) . |
| WO 8900995A1 | 2/1989 | (WO) . |
| WO 9407896A1 | 4/1994 | (WO) . |

*Primary Examiner*—Zinna Northington Davis
(74) *Attorney, Agent, or Firm*—Birch, Stewart, Kolasch & Birch, LLP

(57) ABSTRACT

The present invention provides a quinolinomorphinan derivative or a pharmacologically acceptable acid addition salt thereof, and an agent for curing or preventing cerebral disorders composed of the derivative and salt thereof, which is represented by the following formula (I):

(I)

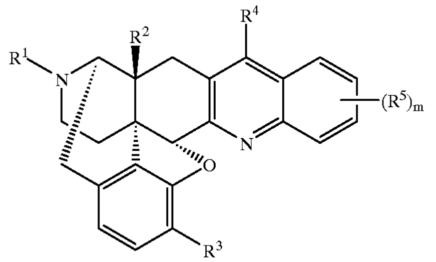

(wherein $R^1$ represents cyclopropylmethyl or the like; $R^2$ and $R^3$ independently represent hydroxy, methoxy, or the like; $R^4$ represents hydrogen, methyl, amino or the like; and $(R^5)_m$ represents hydrogen, substituted benzo, or the like. The compounds of the present invention prevent damages of the cerebral nerve cells and are useful as medicine for curing or preventing various cerebral diseases such as cerebral stroke, traumatic cerebral diseases, cerebral edema, and cerebral neurodegenerative diseases. The compounds of the present invention also ameliorate the after-effects of these diseases and prevent the recurrence of these diseases by inhibiting various ischemic, hemorrhagic or traumatic cerebral disorders, and damages of the cerebral nerve cells caused by various nerve degenerations.

29 Claims, No Drawings

QUINOLINOMORPHINANE DERIVATIVES AND MEDICINAL USE THEREOF

This application is the national phase under 35 U.S.C. §371 of prior PCT International Application No. PCT/JP98/01443 which has an International filing date of Mar. 30, 1998 which designated the United States of America.

TECHNICAL FIELD

The present invention relates to quinolinomorphinan derivatives or pharmacologically acceptable acid addition salts thereof, and an agent for curing or preventing worsening of cerebral disorders comprising one of the derivatives or salts thereof, and particularly to a medicine useful for ameliorating various cerebral diseases and aftereffects thereof, and preventing the recurrence thereof.

BACKGROUND ART

In recent years, cases of diseases in the cerebral region such as various cerebrovascular diseases have increased with the arrival of the aging society. Cerebrovascular diseases are possibly caused by aging, hypertension, arterial sclerosis, hyperlipidemia, and the like, and are generally referred to as "cerebral stroke". In a broad sense, cerebral vascular diseases possibly include functional disorders of the brain due to head trauma.

Cerebral stroke is roughly classified into ischemic (infarcted) diseases and hemorrhagic diseases. Examples of the former include cerebral infarction (cerebral thrombosis, cerebral embolism), and the like, and examples of the latter include cerebral hemorrhage, subarachnoid hemorrhage, and the like. In these diseases, the blood flow is clogged due to a cerebrovascular disorder, and thus glucose and oxygen, which are energy sources of the action of the cerebral nerve cells, are insufficiently supplied, resulting in various damages of the nerve cells. These diseases are fundamentally caused by death of the cerebral nerve cells of a damage area and the periphery thereof. Such cerebrovascular diseases cause occurrence of various aftereffects such as cerebrovascular dementia, which are critical medical and social problems at present.

Medicines which have been developed as agents for curing such cerebrovascular diseases in Japan are mainly used for ameliorating aftereffects such as psychoneurosis and the like, and main medicines have the function to increase the amount of the blood flow to the brain to promote the supply of glucose and oxygen to an ischemic area. From the viewpoint of the functional mechanism, these medicines are expressed by vague terms such as medicines for ameliorating the cerebral blood flow, medicines for activating cerebral metabolism, and medicines for ameliorating cerebral function. However, almost all of these medicines are effective in ameliorating marginal symptoms such as volition disorders, affective disorders, behavioral abnormality, and the like, while the activity to the nucleus symptoms of dementia such as memory disorders and the like is considered as doubtful. Also some anti cerebral edema agents, antithrombotic agents, and thrombolytic agents are clinically used, particularly, in the acute stage of a cerebrovascular disease. These agents also have no direct action on the cerebral nerve cells, but are used only for symptomatic therapy. In any case, the above present medicines have substantially no effect on damage of the cerebral nerve cells in cerebrovascular diseases, and have no action to inhibit directly the death of the cerebral nerve cells.

As described above, there is now no medicine effective against damage of the cerebral nerve cells which are fundamental causes of cerebrovascular diseases. It is known that the degree of such damage has correlation to the ischemia time the cerebral blood flow is clogged, and a long ischemia time causes organic damage of the cerebral nerve cells which are not ameliorated even by recovery of the blood flow. For such cerebrovascular disorders, it is important to cure the disorders in the acute stage within 24 hours from the occurrence of the diseases. Therefore, there is now demand for developing, as early as possible, a safe medicine which has a secure protective effect on damages of the cerebral nerve cells and which is easy to use.

In addition to such cerebrovascular disorders, an increase in cerebral neurodegenerative diseases such as Alzheimer's disease is also a problem, and approach for elucidating causes and developing a therapeutic method is actively carried out in various fields. Although the main object of the approach is to activate, particularly, the acetylcholine nervous system, approach is also carried out by employing the neuroprotective action by a substance related to a nerve growth factor, a neurotrophic factor for the death of the nerve cells due to cerebral neurodegenerative diseases. Also the effect of a medicine having the cerebral neuroprotective action is expected.

The present invention relates to an agent for curing or preventing worsening of cerebral disorders, and an object of the present invention is to provide a medicine useful for ameliorating various cerebral diseases and aftereffects thereof, and preventing the recurrence thereof. Particularly, the present invention provides a medicine useful for curing or preventing worsening of cerebral stroke, traumatic cerebral diseases, cerebral edema, and cerebral neurodegenerative diseases by inhibiting various ischemic, hemorrhagic or traumatic cerebral disorders and damage of the cerebral nerve cells caused by various nerve degeneration, to protect the cerebral nerve cells.

DISCLOSURE OF INVENTION

The object can be achieved by the present invention described below.

The present invention relates to an agent for curing or preventing worsening of cerebral disorders comprising a quinolinomorphinan derivative or a pharmacologically acceptable acid addition salt thereof, which is represented by the following formula (I):

(I)

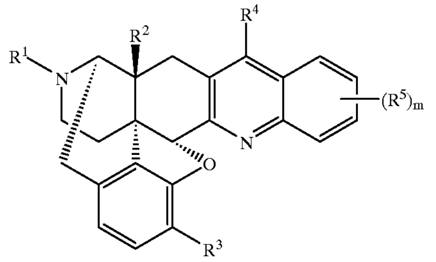

wherein $R^1$ represents hydrogen, alkyl having 1 to 5 carbon atoms, cycloalkylalkyl having 4 to 7 carbon atoms, cycloalkenylalkyl having 5 to 7 carbon atoms, aryl having 6 to 12 carbon atoms, aralkyl having 7 to 13 carbon atoms, alkenyl having 2 to 7 carbon atoms, alkanoyl having 1 to 5 carbon atoms, furan-2-ylalkyl (wherein an alkyl moiety has 1 to 5 carbon atoms), or thiophene-2-ylalkyl (wherein an alkyl moiety has 1 to 5 carbon atoms);

$R^2$ and $R^3$ independently represent hydrogen, hydroxy, alkoxy having 1 to 5 carbon atoms, alkanoyloxy having 1 to 5 carbon atoms, aralkyloxy having 7 to 13 carbon atoms, or arylcarbonyloxy having 7 to 13 carbon atoms;

m represents an integer of 0 to 4;

$R^5$ is each of m substituents on the benzene ring, which independently represent $R^{18}$, or two $R^5$ substituted at adjacent carbons form together a fused ring structure A (wherein residual 0 to 2 substituents $R^5$ each represent $R^{18}$ or form another fused ring structure A);

the fused ring structure A is benzo, indeno, naphtho, pyrido, or cycloalkeno having 5 to 7 carbon atoms, which is substituted by 0 to 4 substituents $R^9$, or unsubstituted dioxoleno;

$R^9$ and $R^{18}$ (1) independently represent fluoro, chloro, bromo, iodo, nitro, hydroxy, alkyl having 1 to 5 carbon atoms, alkoxy having 1 to 5 carbon atoms, isothiocyanato, trifluoromethyl, trifluoromethoxy, cyano, phenyl, hydroxyalkyl having 1 to 3 carbon atoms, $SR^6$, $SOR^6$, $SO_2R^6$, $(CH_2)_kCO_2R^7$, $SO_2NR^7R^8$, $CONR^7R^8$, $(CH_2)_kNR^7R^8$, or $(CH_2)_kN(R^7)COR^8$ (wherein k represents an integer of 0 to 5, $R^6$ represents alkyl having 1 to 5 carbon atoms, and $R^7$ and $R^8$ independently represent hydrogen, alkyl having 1 to 5 carbon atoms, or cycloalkylalkyl having 4 to 6 carbon atoms), and/or (2) $R^9$ and $R^{18}$ substituted at adjacent carbons with a ring junction therebetween form together any one of ethano, propano and o-benzeno bridged structures $R^9$—$R^{18}$; and $R^4$ represents hydrogen, alkyl having 1 to 5 carbon atoms, hydroxyalkyl having 1 to 5 carbon atoms, aryl having 6 to 12 carbon atoms (which may be substituted by at least one substituent $R^{17}$), $NR^{10}R^{11}$, $OR^{12}$, $COOR^{13}$ or $CONR^{14}R^{15}$, or any one of bridged structures $R^4$—$R^5$ of $N(R^{16})CO$, $N(R^{16})C(=NH)$, $N(R^{16})CH_2$, o-benzeno, ethano, propano, and butano, which are formed together by $R^4$ and $R^5$ substituted at the peri position;

$R^{17}$ represents fluoro, chloro, bromo, iodo, nitro, amino, hydroxy, alkyl having 1 to 5 carbon atoms, alkoxy 1 to 5 carbon atoms, alkanoyloxy having 1 to 5 carbon atoms, trifluoromethyl, trifluoromethoxy or cyano;

$R^{10}$, $R^{11}$, $R^{12}$ and $R^{16}$ independently represent hydrogen, alkyl having 1 to 5 carbon atoms, cycloalkylalkyl having 4 to 7 carbon atoms, aralkyl having 7 to 13 carbon atoms, or alkanoyl having 1 to 5 carbon atoms; and $R^{13}$, $R^{14}$ and $R^{15}$ independently represent hydrogen, alkyl having 1 to 5 carbon atoms, aryl having 6 to 12 carbon atoms, or aralkyl having 7 to 13 carbon atoms; and formula (I) includes (+) form, (−) form and (±) form].

The present invention also relates to quinolinomorphinan derivatives and pharmacologically acceptable acid addition salts thereof represented by the following formula (II):

(II)

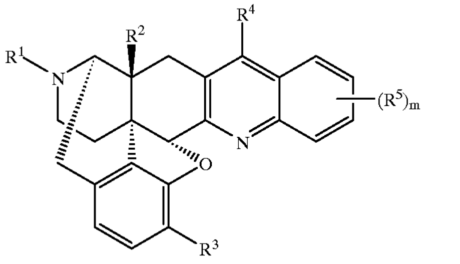

[wherein $R^1$, $R^2$, $R^3$, m, $R^5$, k, $R^6$, $R^7$, $R^8$, A, $R^9$, $R^{18}$, $R^4$, $R^{17}$, $R^{10}$, $R^{11}$, $R^{12}$, $R^{13}$, $R^{14}$, $R^{15}$ and $R^{16}$ are defined as the same as the above (wherein with hydrogen as $R^4$, when (1) m is 1, $R^5$ is $R^{18}$ which represents hydroxy, and when (2) m is an integer of 2 to 4, $R^5$ is $R^{18}$ at least one of which represents hydroxy, or two $R^5$ form together a fused ring structure A, and the residual 0 to 2 $R^5$ independently represent $R^{18}$ (wherein when the fused ring structure A is benzo, pyrido, or cycloalkeno having 5 to 7 carbon atoms, at least one $R^{18}$ represents hydroxy, or at least one $R^9$ and one $R^{18}$ substituted at adjacent carbons with a ring junction therebetween form together a bridged structure $R^9$—$R^{18}$ which is any one of ethano, propano and o-benzeno), or must form another fused ring structure A); and formula (II) includes (+) form, (−) form and (±) form].

BEST MODE FOR CARRYING OUT THE INVENTION

Preferred embodiments of the agent for curing or preventing worsening of cerebral disorders comprising an quinolinomorphinan derivative or a pharmacologically acceptable acid addition salt thereof represented by formula (I) of the present invention are as follows.

$R^1$ is preferably hydrogen, alkyl having 1 to 5 carbon atoms, cycloalkylmethyl having 4 to 7 carbon atoms, cycloalkenylmethyl having 5 to 7 carbon atoms, phenyl, naphthyl, phenylalkyl having 7 to 13 carbon atoms, alkenyl having 2 to 7 carbon atoms, alkanoyl having 1 to 5 carbon atoms, furan-2-ylalkyl having 1 to 5 carbon atoms (wherein the number of carbons indicates the number of the carbons of the alkyl moiety of furan-2-ylalkyl), or thiophene-2-ylalkyl having 1 to 5 carbon atoms (wherein the number of carbons indicates the number of the carbons of the alkyl moiety of thiophene-2-ylalkyl), and more preferably hydrogen, methyl, ethyl, propyl, butyl, cyclopropylmethyl, cyclobutylmethyl, cyclopentylmethyl, benzyl, phenethyl, allyl, 2-butenyl, 3-butenyl, 2-methyl-2-butenyl, 3-methyl-2-butenyl, 3-methyl-3-butenyl, acetyl, furan-2-ylmethyl, or thiophene-2-ylmethyl. Of these groups, hydrogen, methyl, cyclopropylmethyl, cyclobutylmethyl, benzyl, phenethyl, ally and acetyl are preferred.

$R^2$ and $R^3$ are preferably hydrogen, hydroxy, methoxy, ethoxy, propoxy, acetoxy, benzyloxy, or benzoyloxy. Of these groups, $R^2$ is more preferably hydroxy, methoxy, or acetoxy, and $R^3$ is more preferably hydrogen, hydroxy or methoxy.

When $R^5$ does not form the fused ring structure A, $R^5$ represents $R^{18}$ which is preferably fluoro, chloro, bromo, iodo, nitro, hydroxy, methyl, ethyl, propyl, butyl, methoxy, ethoxy, isothiocyanato, trifluoromethyl, trifluoromethoxy, cyano, phenyl, hydroxymethyl, $SR^6$, $SOR^6$, $SO_2R^6$, $CO_2R^7$, $CH_2CO_2R^7$, $(CH_2)_2CO_2R^7$, $SO_2NR^7R^8$, $CONR^7R^8$, $NR^7R^8$, $CH_2NR^7R^8$, $(CH_2)_2NR^7R^8$, $N(R^7)COR^8$, $CH_2N(R^7)COR^8$, or $(CH_2)_2N(R^7)COR^8$, wherein $R^6$ is preferably methyl or ethyl, $R^7$ is preferably hydrogen or methyl, and $R^8$ is preferably hydrogen, methyl, ethyl, propyl, butyl, cyclopropylmethyl, or cyclobutylmethyl. When two groups $R^5$ form together a fused ring structure A, the residual 0 to 2 groups $R^5$ are the above $R^{18}$, or the residual two $R^5$ form together another fused ring structure A. The fused ring structure A is preferably benzo, indeno, naphtho, pyrido or cyclohexeno, which is substituted by 0 or 2 groups $R^9$, or unsubstituted dioxoleno. Particularly, benzo, indeno and cyclohexeno which are substituted by 0 to 1 $R^9$, and unsubstituted dioxoleno are preferable. For example, when two $R^5$ groups form together a fused ring structure A which is benzo, examples of compounds of formula (I) include compounds represented by the following formulae (IVa), (IVb), (IVc) and (IVd). However, the compounds of formula (I) are not limited to these compounds.

(IVa)

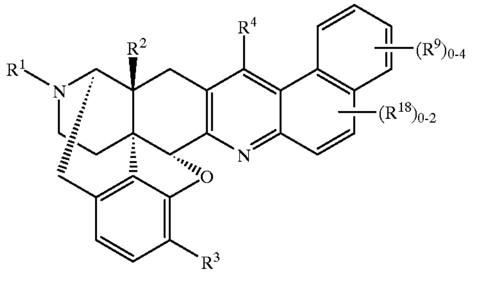

(IVb)

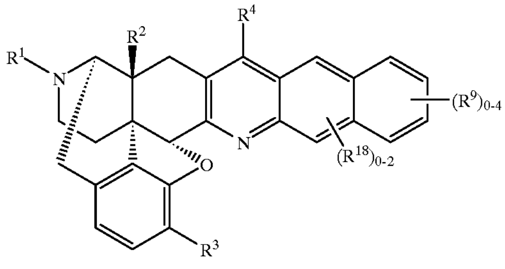

(IVc)

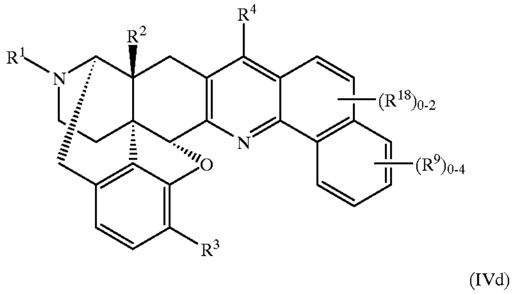

(IVd)

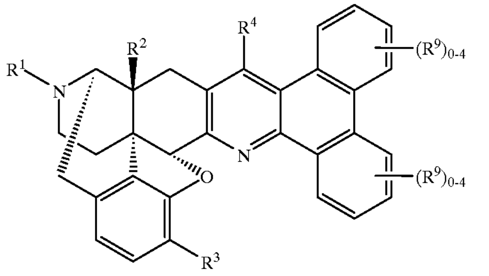

When $R^9$ does not form a bridged structure $R^9$—$R^{18}$ together with $R^{18}$, $R^9$ is preferably fluoro, chloro, bromo, iodo, nitro, hydroxy, methyl, ethyl, propyl, butyl, methoxy, ethoxy, isothiocyanato, trifluoromethyl, trifluoromethoxy, cyano, phenyl, hydroxymethyl, $SR^6$, $SOR^6$, $SO_2R^6$, $CH_2CO_2R^7$, $(CH_2)_2CO_2R^7$, $SO_2NR^7R^8$, $CONR^7R^8$, $NR^7R^8$, $CH_2NR^7R^8$, $(CH_2)_2NR^7R^8$, $N(R^7)COR^8$, $CH_2N(R^7)COR^8$, or $(CH_2)_2N(R^7)COR^8$, wherein $R^6$ is preferably methyl or ethyl, $R^7$ is preferably hydrogen or methyl, and $R^8$ is preferably hydrogen, methyl, ethyl, propyl, butyl, cyclopropylmethyl, or cyclobutylmethyl. $R^9$ and $R^{18}$ may form a bridged structure of $R^9$—$R^{18}$ together. In this case, ethano or o-benzeno is preferable as the bridged structure. For example, the bridged structure is ethano, and the fused ring structure A is benzo, examples of compounds of formula (I) include compounds represented by the following formulae (Va), (Vb), (Vc) and (Vd). The compounds of formula (I) are not limited to these compounds.

(Va)

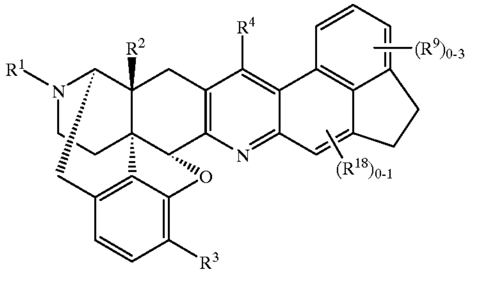

(Vb)

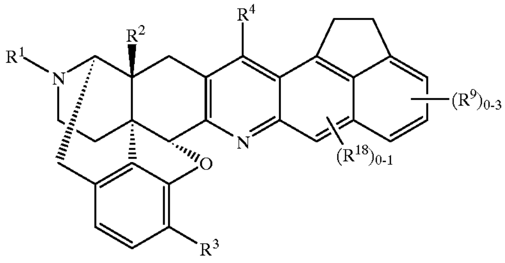

(Vc)

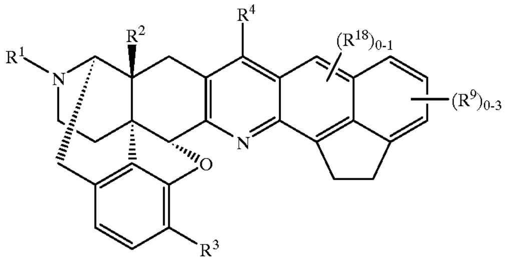

(Vd)

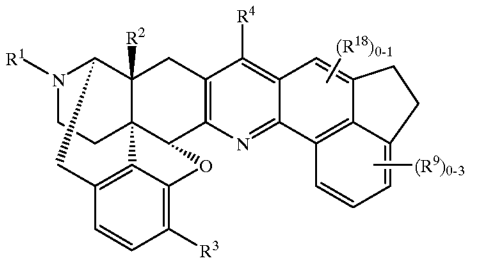

When $R^4$ and $R^5$ substituted at the peri position do not form together a bridged structure $R^4$—$R^5$, $R^4$ is preferably hydrogen, methyl, ethyl, propyl, isopropyl, hydroxyalkyl having 1 to 3 carbon atoms, aryl having 6 to 12 carbon atoms (which may be substituted by at least one substituent $R^{17}$), $NR^{10}R^{11}$, $OR^{12}$, $COOR^{13}$ or $CONR^{14}R^{15}$, wherein $R^{10}$ is preferably hydrogen or methyl, $R^{11}$ is preferably hydrogen, alkyl having 1 to 5 carbon atoms, cycloalkylalkyl having 4 to 7 carbon atoms, benzyl, phenethyl or alkanoyl having 1 to 5 carbon atoms, $R^{12}$ is preferably hydrogen, methyl or acetyl, $R^{13}$ is preferably hydrogen, methyl, ethyl, phenyl or benzyl, $R^{14}$ is preferably hydrogen, methyl, ethyl, phenyl or benzyl, $R^{15}$ is preferably hydrogen, methyl, ethyl, phenyl or benzyl, and $R^{17}$ is preferably fluoro, chloro, bromo, amino, methyl or ethyl.

Of these groups, $R^4$ is preferably hydrogen, methyl, ethyl, isopropyl, hydroxymethyl, hydroxyethyl, phenyl, naphthyl, amino, methylamino, dimethylamino, (cyclohexylmethyl) amino, benzylamino, phenethylamino, formylamino, acetylamino, propionylamino, hydroxy, methoxy, acetoxy, carboxy, methoxycarbonyl, ethoxycarbonyl, phenoxycarbonyl, benzyloxycarbonyl, carbamoyl, methylcarbamoyl, phenylcarbamoyl, benzylcarbamoyl or dimethylcarbamoyl; particularly hydrogen, methyl, ethyl, isopropyl, hydroxymethyl, phenyl, amino, methylamino, dimethylamino, (cyclohexylmethyl)amino, benzylamino, formylamino, acetylamino, hydroxy, methoxy, carboxy, methoxycarbonyl, carbamoyl, methylcarbamoyl or dimethylcarbamoyl. When $R^4$ and $R^5$ substituted at the peri position form together a bridged structure $R^4$—$R^5$, the bridged structure $R^4$—$R^5$ is preferably $N(R^{16})CO$, $N(R^{16})C(=NH)$, $N(R^{16})CH_2$, o-benzeno, or propano; particularly $N(R^{16})CO$, $N(R^{16})C(=NH)$, or $N(R^{16})CH_2$. In this case, $R^{16}$ is preferably hydrogen, methyl, ethyl, benzyl, or acetyl. For example, $R^4$ and $R^5$ substituted at peri-position form together a bridged structure $R^4$—$R^5$ which is $N(R^{16})CO$, compounds of formula (I) are represented by the following formula (VI). However, compounds of formula (I) are not limited to these compounds.

(VI)

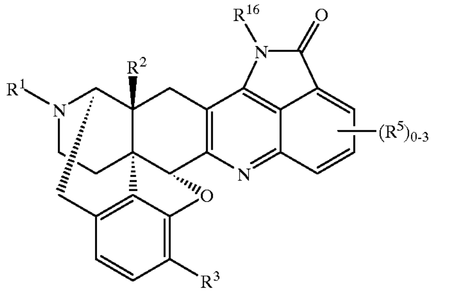

Preferred embodiments of the quinolinomorphinan derivatives or pharmacologically acceptable acid addition salts thereof represented by formula (II) of the present invention are basically the same as preferred embodiments of the agent for curing or preventing worsening of cerebral disorder comprising any one of the quinolinomorphinan derivatives or pharmacologically acceptable acid addition salts thereof represented by formula (I) of the present invention. However, with hydrogen as $R^4$, (1) when m is 1, $R^5$ is hydroxy, and (2) when m is an integer of 2 to 4, $R^5$ represents hydroxy, or two $R^5$ groups necessarily form together a fused ring structure A, and the residual 0 or 2 $R^5$ groups are independently $R^{18}$ or must form another fused ring structure A. In this case, the fused ring structure A is preferably benzo, pyrido or cycloalkeno having 5 to 7 carbon atoms, which is substituted by 1 or 2 substituents $R^9$, or indeno or naphtho unsubstituted by $R^9$, or unsubstituted dioxoleno. Particularly, when the fused ring structure A is benzo, pyrido or cycloalkeno having 5 to 7 carbon atoms, which is substituted by 1 or 2 substituents $R^9$, at least one substituent $R^{18}$ is hydroxy, or at least one $R^9$ and one $R^{18}$ substituted at adjacent carbons with a ring junction therebetween necessarily form a bridged structure $R^9$—$R^{18}$ together which is any one of ethano, propano, and o-benzeno structures. In this case, as the bridged structure $R^9$—$R^{18}$, ethano and o-benzeno are preferable.

Preferable examples of pharmacologically acceptable acid addition salts include inorganic salts such as a hydrochloride, a sulfate, a nitrate, a hydrobromide, a hydroiodide, a phosphate, and the like; organic carboxylates such as an acetate, a lactate, a citrate, an oxalate, a glutarate, a malate, a tartrate, a fumarate, a mandelate, a maleate, a benzoate, a phthalate, and the like; organic sulfonates such as a methanesulfonate, an ethanesulfonate, a benzenesulfonate, a p-toluenesulfonate, a camphorsulfonate, and the like. Particularly, a hydrochloride, a phosphate, a tartrate, a methanesulfonate, and the like are preferable, but, of course, the salts are not limited to these salts.

Of the compounds of formula (I) of the present invention, compound 1 is designated 17-cyclopropylmethyl-6,7-dehydro-4,5α-epoxy-3,14β-dihydroxy-6,7,2',3'-quinolinomorphinan, in which $R^1$ is cyclopropylmethyl, $R^2$ and $R^3$ are each hydroxy, $R^4$ is hydrogen, and m is 0.

1

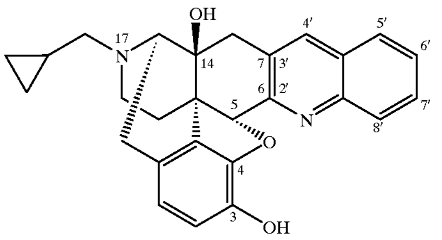

Of the compounds of formula (I) of the present invention, compound 36 is designated 17-cyclopropylmethyl-6,7-dehydro-4,5α-epoxy-3,14β-dihydroxy-6,7,2',3'-(7',8'-benzoquinolino)morphinan, in which $R^1$ is cyclopropylmethyl, $R^2$ and $R^3$ are each hydroxy, $R^4$ is hydrogen, m is 2, and two $R^5$ groups are substituents at the 7' and 8'-positions of the quinoline ring and form together the fused ring structure A which is benzo.

36

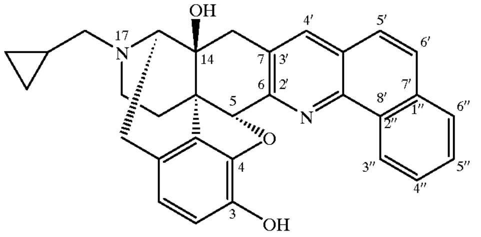

Of the compounds of formula (I) of the present invention, compound 44 is designated 17-cyclopropylmethyl- 6,7-dehydro-4,5α-epoxy-3,14β-dihydroxy-6,7,2',3'-(6',6"-ethano-7',8'-benzoquinolino)morphinan, in which $R^1$ is cyclopropylmethyl, $R^2$ and $R^3$ are each hydroxy, $R^4$ is hydrogen, m is 3, two $R^5$ groups are substituents at the 7' and 8'-positions of the quinoline ring and form together the fused ring structure A which is benzo substituted by one $R^9$, and the residual one $R^5$ is $R^{18}$ substituted at the 6'-position of the quinoline ring and forming ethano as a bridged structure $R^9$—$R^{18}$ together with $R^9$ substituted at the 6"-position of the benzene ring adjacent to $R^{18}$ with the ring junction therebetween.

44

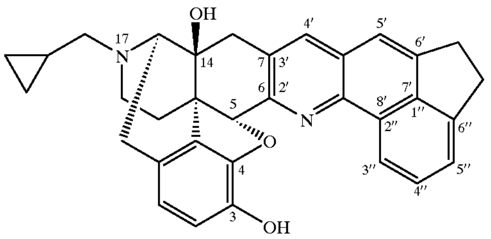

Of the compounds of formula (I) of the present invention, compound 39 is designated 17-cyclopropylmethyl-6,7-dehydro-4,5α-epoxy-3,14β-dihydroxy-6,7,2',3'-(7',8'- cyclohexenoquinolino)morphinan, in which $R^1$ is cyclopropylmethyl, $R^2$ and $R^3$ are each hydroxy, $R^4$ is hydrogen, m is 2, and two $R^5$ groups are substituents at the 7' and 8'-positions of the quinoline ring and form together the fused ring structure A which is cyclohexeno.

39

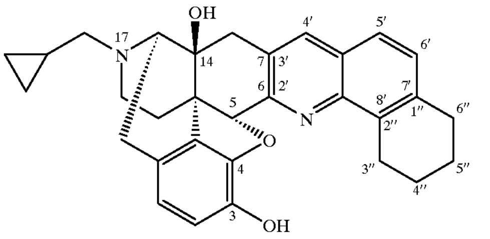

Of the compounds of formula (I) of the present invention, compound 29 is designated 17-cyclopropylmethyl-6,7-dehydro-4,5α-epoxy-3,14β-dihydroxy-6,7,2',3'-(4'-methyl-6',7'-dioxolenoquinolino)morphinan, in which $R^1$ is cyclopropylmethyl, $R^2$ and $R^3$ are each hydroxy, $R^4$ is methyl, m is 2, and two $R^5$ groups are substituents at the 6' and 7'-positions of the quinoline ring and form together the fused ring structure A which is dioxoleno.

29

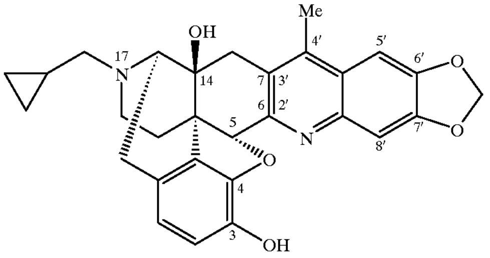

Of the compounds of formula (I) of the present invention, compound 34 is designated 17-cyclopropylmethyl- 6,7-dehydro-4,5α-epoxy-3,14β-dihydroxy-6,7,2',3'-[4',5'-[imino(oxomethano)]quinolino]morphinan, in which $R^1$ is cyclopropylmethyl, $R^2$ and $R^3$ are each hydroxy, and $R^4$ forms a bridged structure $R^4$—$R^5$ together with $R^5$ substituted at the 5'-position as the peri position of the quinoline ring which is $N(R^{16})CO$ wherein $R^{16}$ is hydrogen.

34

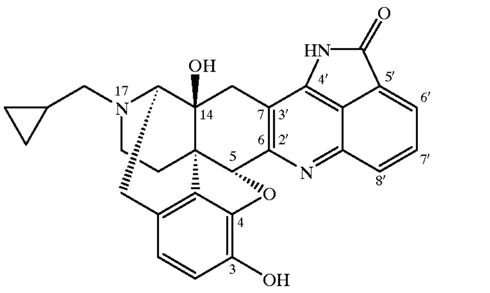

Although examples of compounds as the quinolinomorphinan derivatives represented by formula (I) of the present invention include the following compounds listed in the tables below, the present invention not limited to these compounds.

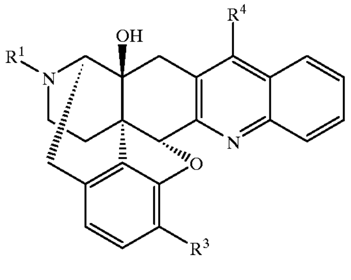

| $R^1$ | $R^3$ | $R^4$ |
|---|---|---|
| H | OH | H |
| Me | OH | H |
| cyclopropylmethyl | OH | H |
| cyclobutylmethyl | OH | H |
| benzyl | OH | H |
| 2-phenethyl | OH | H |
| allyl | OH | H |
| acetyl | OH | H |
| H | $OCH_3$ | H |
| Me | $OCH_3$ | H |
| cyclopropylmethyl | $OCH_3$ | H |
| cyclobutylmethyl | $OCH_3$ | H |
| benzyl | $OCH_3$ | H |
| 2-phenethyl | $OCH_3$ | H |
| allyl | $OCH_3$ | H |
| acetyl | $OCH_3$ | H |
| H | OH | Me |
| Me | OH | Me |
| cyclopropylmethyl | OH | Me |
| cyclobutylmethyl | OH | Me |
| benzyl | OH | Me |
| 2-phenethyl | OH | Me |
| allyl | OH | Me |
| acetyl | OH | Me |
| H | $OCH_3$ | Me |
| Me | $OCH_3$ | Me |
| cyclopropylmethyl | $OCH_3$ | Me |
| cyclobutylmethyl | $OCH_3$ | Me |
| benzyl | $OCH_3$ | Me |
| 2-phenethyl | $OCH_3$ | Me |
| allyl | $OCH_3$ | Me |
| acetyl | $OCH_3$ | Me |
| H | OH | Et |
| Me | OH | Et |
| cyclopropylmethyl | OH | Et |
| cyclobutylmethyl | OH | Et |
| benzyl | OH | Et |
| 2-phenethyl | OH | Et |
| allyl | OH | Et |
| acetyl | OH | Et |
| H | $OCH_3$ | Et |
| Me | $OCH_3$ | Et |
| cyclopropylmethyl | $OCH_3$ | Et |
| cyclobutylmethyl | $OCH_3$ | Et |
| benzyl | $OCH_3$ | Et |
| 2-phenethyl | $OCH_3$ | Et |
| allyl | $OCH_3$ | Et |
| acetyl | $OCH_3$ | Et |
| H | OH | $CH_2OH$ |
| Me | OH | $CH_2OH$ |
| cyclopropylmethyl | OH | $CH_2OH$ |
| cyclobutylmethyl | OH | $CH_2OH$ |
| benzyl | OH | $CH_2OH$ |
| 2-phenethyl | OH | $CH_2OH$ |
| allyl | OH | $CH_2OH$ |
| acetyl | OH | $CH_2OH$ |
| H | $OCH_3$ | $CH_2OH$ |
| Me | $OCH_3$ | $CH_2OH$ |
| cyclopropylmethyl | $OCH_3$ | $CH_2OH$ |
| cyclobutylmethyl | $OCH_3$ | $CH_2OH$ |
| benzyl | $OCH_3$ | $CH_2OH$ |
| 2-phenethyl | $OCH_3$ | $CH_2OH$ |

-continued

| | | |
|---|---|---|
| allyl | $OCH_3$ | $CH_2OH$ |
| acetyl | $OCH_3$ | $CH_2OH$ |
| H | OH | $CH_2OH_2OH$ |
| Me | OH | $CH_2OH_2OH$ |
| cyclopropylmethyl | OH | $CH_2OH_2OH$ |
| cyclobutylmethyl | OH | $CH_2OH_2OH$ |
| benzyl | OH | $CH_2OH_2OH$ |
| 2-phenethyl | OH | $CH_2OH_2OH$ |
| allyl | OH | $CH_2OH_2OH$ |
| acetyl | OH | $CH_2OH_2OH$ |
| H | $OCH_3$ | $CH_2OH_2OH$ |
| Me | $OCH_3$ | $CH_2OH_2OH$ |
| cyclopropylmethyl | $OCH_3$ | $CH_2OH_2OH$ |
| cyclobutylmethyl | $OCH_3$ | $CH_2OH_2OH$ |
| benzyl | $OCH_3$ | $CH_2OH_2OH$ |
| 2-phenethyl | $OCH_3$ | $CH_2OH_2OH$ |
| allyl | $OCH_3$ | $CH_2OH_2OH$ |
| acetyl | $OCH_3$ | $CH_2OH_2OH$ |
| H | OH | Phenyl |
| Me | OH | Phenyl |
| cyclopropylmethyl | OH | Phenyl |
| cyclobutylmethyl | OH | Phenyl |
| benzyl | OH | Phenyl |
| 2-phenethyl | OH | Phenyl |
| allyl | OH | Phenyl |
| acetyl | OH | Phenyl |
| H | $OCH_3$ | Phenyl |
| Me | $OCH_3$ | Phenyl |
| cyclopropylmethyl | $OCH_3$ | Phenyl |
| cyclobutylmethyl | $OCH_3$ | Phenyl |
| benzyl | $OCH_3$ | Phenyl |
| 2-phenethyl | $OCH_3$ | Phenyl |
| allyl | $OCH_3$ | Phenyl |
| acetyl | $OCH_3$ | Phenyl |
| H | OH | naphthyl |
| Me | OH | naphthyl |
| cyclopropylmethyl | OH | naphthyl |
| cyclobutylmethyl | OH | naphthyl |
| benzyl | OH | naphthyl |
| 2-phenethyl | OH | naphthyl |
| allyl | OH | naphthyl |
| acetyl | OH | naphthyl |
| H | $OCH_3$ | naphthyl |
| Me | $OCH_3$ | naphthyl |
| cyclopropylmethyl | $OCH_3$ | naphthyl |
| cyclobutylmethyl | $OCH_3$ | naphthyl |
| benzyl | $OCH_3$ | naphthyl |
| 2-phenethyl | $OCH_3$ | naphthyl |
| allyl | $OCH_3$ | naphthyl |
| acetyl | $OCH_3$ | naphthyl |
| H | OH | $NH_2$ |
| Me | OH | $NH_2$ |
| cyclopropylmethyl | OH | $NH_2$ |
| cyclobutylmethyl | OH | $NH_2$ |
| benzyl | OH | $NH_2$ |
| 2-phenethyl | OH | $NH_2$ |
| allyl | OH | $NH_2$ |
| acetyl | OH | $NH_2$ |
| H | $OCH_3$ | $NH_2$ |
| Me | $OCH_3$ | $NH_2$ |
| cyclopropylmethyl | $OCH_3$ | $NH_2$ |
| cyclobutylmethyl | $OCH_3$ | $NH_2$ |
| benzyl | $OCH_3$ | $NH_2$ |
| 2-phenethyl | $OCH_3$ | $NH_2$ |
| allyl | $OCH_3$ | $NH_2$ |
| acetyl | $OCH_3$ | $NH_2$ |
| H | OH | NHMe |
| Me | OH | NHMe |
| cyclopropylmethyl | OH | NHMe |
| cyclobutylmethyl | OH | NHMe |
| benzyl | OH | NHMe |
| 2-phenethyl | OH | NHMe |
| allyl | OH | NHMe |
| acetyl | OH | NHMe |
| H | $OCH_3$ | NHMe |
| Me | $OCH_3$ | NHMe |
| cyclopropylmethyl | $OCH_3$ | NHMe |
| cyclobutylmethyl | $OCH_3$ | NHMe |

-continued

| | | |
|---|---|---|
| benzyl | $OCH_3$ | NHMe |
| 2-phenethyl | $OCH_3$ | NHMe |
| allyl | $OCH_3$ | NHMe |
| acetyl | $OCH_3$ | NHMe |
| H | OH | NHEt |
| Me | OH | NHEt |
| cyclopropylmethyl | OH | NHEt |
| cyclobutylmethyl | OH | NHEt |
| benzyl | OH | NHEt |
| 2-phenethyl | OH | NHEt |
| allyl | OH | NHEt |
| acetyl | OH | NHEt |
| H | $OCH_3$ | NHEt |
| Me | $OCH_3$ | NHEt |
| cyclopropylmethyl | $OCH_3$ | NHEt |
| cyclobutylmethyl | $OCH_3$ | NHEt |
| benzyl | $OCH_3$ | NHEt |
| 2-phenethyl | $OCH_3$ | NHEt |
| allyl | $OCH_3$ | NHEt |
| acetyl | $OCH_3$ | NHEt |
| H | OH | $NMe_2$ |
| Me | OH | $NMe_2$ |
| cyclopropylmethyl | OH | $NMe_2$ |
| cyclobutylmethyl | OH | $NMe_2$ |
| benzyl | OH | $NMe_2$ |
| 2-phenethyl | OH | $NMe_2$ |
| allyl | OH | $NMe_2$ |
| acetyl | OH | $NMe_2$ |
| H | $OCH_3$ | $NMe_2$ |
| Me | $OCH_3$ | $NMe_2$ |
| cyclopropylmethyl | $OCH_3$ | $NMe_2$ |
| cyclobutylmethyl | $OCH_3$ | $NMe_2$ |
| benzyl | $OCH_3$ | $NMe_2$ |
| 2-phenethyl | $OCH_3$ | $NMe_2$ |
| allyl | $OCH_3$ | $NMe_2$ |
| acetyl | $OCH_3$ | $NMe_2$ |
| H | OH | (cyclohexylmethyl)amino |
| Me | OH | (cyclohexylmethyl)amino |
| cyclopropylmethyl | OH | (cyclohexylmethyl)amino |
| cyclobutylmethyl | OH | (cyclohexylmethyl)amino |
| benzyl | OH | (cyclohexylmethyl)amino |
| 2-phenethyl | OH | (cyclohexylmethyl)amino |
| allyl | OH | (cyclohexylmethyl)amino |
| acetyl | OH | (cyclohexylmethyl)amino |
| H | $OCH_3$ | (cyclohexylmethyl)amino |
| Me | $OCH_3$ | (cyclohexylmethyl)amino |
| cyclopropylmethyl | $OCH_3$ | (cyclohexylmethyl)amino |
| cyclobutylmethyl | $OCH_3$ | (cyclohexylmethyl)amino |
| benzyl | $OCH_3$ | (cyclohexylmethyl)amino |
| 2-phenethyl | $OCH_3$ | (cyclohexylmethyl)amino |
| allyl | $OCH_3$ | (cyclohexylmethyl)amino |
| acetyl | $OCH_3$ | (cyclohexylmethyl)amino |
| H | OH | NHBn |
| Me | OH | NHBn |
| cyclopropylmethyl | OH | NHBn |
| cyclobutylmethyl | OH | NHBn |
| benzyl | OH | NHBn |
| 2-phenethyl | OH | NHBn |
| allyl | OH | NHBn |
| acetyl | OH | NHBn |
| H | $OCH_3$ | NHBn |
| Me | $OCH_3$ | NHBn |
| cyclopropylmethyl | $OCH_3$ | NHBn |
| cyclobutylmethyl | $OCH_3$ | NHBn |
| benzyl | $OCH_3$ | NHBn |
| 2-phenethyl | $OCH_3$ | NHBn |
| allyl | $OCH_3$ | NHBn |
| acetyl | $OCH_3$ | NHBn |
| H | OH | $NH(CH_2)_2Ph$ |
| Me | OH | $NH(CH_2)_2Ph$ |
| cyclopropylmethyl | OH | $NH(CH_2)_2Ph$ |
| cyclobutylmethyl | OH | $NH(CH_2)_2Ph$ |
| benzyl | OH | $NH(CH_2)_2Ph$ |
| 2-phenethyl | OH | $NH(CH_2)_2Ph$ |
| allyl | OH | $NH(CH_2)_2Ph$ |
| acetyl | OH | $NH(CH_2)_2Pb$ |
| H | $OCH_3$ | $NH(CH_2)_2Ph$ |
| Me | $OCH_3$ | $NH(CH_2)_2Ph$ |

-continued

| | | |
|---|---|---|
| cyclopropylmethyl | $OCH_3$ | $NH(CH_2)_2Ph$ |
| cyclobutylmethyl | $OCH_3$ | $NH(CH_2)_2Ph$ |
| benzyl | $OCH_3$ | $NH(CH_2)_2Ph$ |
| 2-phenethyl | $OCH_3$ | $NH(CH_2)_2Ph$ |
| allyl | $OCH_3$ | $NH(CH_2)_2Ph$ |
| acetyl | $OCH_3$ | $NH(CH_2)_2Ph$ |
| H | OH | NHCHO |
| Me | OH | NHCHO |
| cyclopropylmethyl | OH | NHCHO |
| cyclobutylmethyl | OH | NHCHO |
| benzyl | OH | NHCHO |
| 2-phenethyl | OH | NHCHO |
| allyl | OH | NHCHO |
| acetyl | OH | NHCHO |
| H | $OCH_3$ | NHCHO |
| Me | $OCH_3$ | NHCHO |
| cyclopropylmethyl | $OCH_3$ | NHCHO |
| cyclobutylmethyl | $OCH_3$ | NHCHO |
| benzyl | $OCH_3$ | NHCHO |
| 2-phenethyl | $OCH_3$ | NHCHO |
| allyl | $OCH_3$ | NHCHO |
| acetyl | $OCH_3$ | NHCHO |
| H | OH | NHCOMe |
| Me | OH | NHCOMe |
| cyclopropylmethyl | OH | NHCOMe |
| cyclobutylmethyl | OH | NHCOMe |
| benzyl | OH | NHCOMe |
| 2-phenethyl | OH | NHCOMe |
| allyl | OH | NHCOMe |
| acetyl | OH | NHCOMe |
| H | $OCH_3$ | NHCOMe |
| Me | $OCH_3$ | NHCOMe |
| cyclopropylmethyl | $OCH_3$ | NHCOMe |
| cyclobutylmethyl | $OCH_3$ | NHCOMe |
| benzyl | $OCH_3$ | NHCOMe |
| 2-phenethyl | $OCH_3$ | NHCOMe |
| allyl | $OCH_3$ | NHCOMe |
| acetyl | $OCH_3$ | NHCOMe |
| H | OH | NHCOEt |
| Me | OH | NHCOEt |
| cyclopropylmethyl | OH | NHCOEt |
| cyclobutylmethyl | OH | NHCOEt |
| benzyl | OH | NHCOEt |
| 2-phenethyl | OH | NHCOEt |
| allyl | OH | NHCOEt |
| acetyl | OH | NHCOEt |
| H | $OCH_3$ | NHCOEt |
| Me | $OCH_3$ | NHCOEt |
| cyclopropylmethyl | $OCH_3$ | NHCOEt |
| cyclobutylmethyl | $OCH_3$ | NHCOEt |
| benzyl | $OCH_3$ | NHCOEt |
| 2-phenethyl | $OCH_3$ | NHCOEt |
| allyl | $OCH_3$ | NHCOEt |
| acetyl | $OCH_3$ | NHCOEt |
| H | OH | OH |
| Me | OH | OH |
| cyclopropylmethyl | OH | OH |
| cyclobutylmethyl | OH | OH |
| benzyl | OH | OH |
| 2-phenethyl | OH | OH |
| allyl | OH | OH |
| acetyl | OH | OH |
| H | $OCH_3$ | OH |
| Me | $OCH_3$ | OH |
| cyclopropylmethyl | $OCH_3$ | OH |
| cyclobutylmethyl | $OCH_3$ | OH |
| benzyl | $OCH_3$ | OH |
| 2-phenethyl | $OCH_3$ | OH |
| allyl | $OCH_3$ | OH |
| acetyl | $OCH_3$ | OH |
| H | OH | OMe |
| Me | OH | OMe |
| cyclopropylmethyl | OH | OMe |
| cyclobutylmethyl | OH | OMe |
| benzyl | OH | OMe |
| 2-phenethyl | OH | OMe |
| allyl | OH | OMe |
| acetyl | OH | OMe |

-continued

| | | |
|---|---|---|
| H | $OCH_3$ | OMe |
| Me | $OCH_3$ | OMe |
| cyclopropylmethyl | $OCH_3$ | OMe |
| cyclobutylmethyl | $OCH_3$ | OMe |
| benzyl | $OCH_3$ | OMe |
| 2-phenethyl | $OCH_3$ | OMe |
| allyl | $OCH_3$ | OMe |
| acetyl | $OCH_3$ | OMe |
| H | OH | OAc |
| Me | OH | OAc |
| cyclopropylmethyl | OH | OAc |
| cyclobutylmethyl | OH | OAc |
| benzyl | OH | OAc |
| 2-phenethyl | OH | OAc |
| allyl | OH | OAc |
| acetyl | OH | OAc |
| H | $OCH_3$ | OAc |
| Me | $OCH_3$ | OAc |
| cyclopropylmethyl | $OCH_3$ | OAc |
| cyclobutylmethyl | $OCH_3$ | OAc |
| benzyl | $OCH_3$ | OAc |
| 2-phenethyl | $OCH_3$ | OAc |
| allyl | $OCH_3$ | OAc |
| acetyl | $OCH_3$ | OAc |
| H | OH | $CO_2H$ |
| Me | OH | $CO_2H$ |
| cyclopropylmethyl | OH | $CO_2H$ |
| cyclobutylmethyl | OH | $CO_2H$ |
| benzyl | OH | $CO_2H$ |
| 2-phenethyl | OH | $CO_2H$ |
| allyl | OH | $CO_2H$ |
| acetyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| cyclobutylmethyl | $OCH_3$ | $CO_2H$ |
| benzyl | $OCH_3$ | $CO_2H$ |
| 2-phenethyl | $OCH_3$ | $CO_2H$ |
| allyl | $OCH_3$ | $CO_2H$ |
| acetyl | $OCH_3$ | $CO_2H$ |
| H | OH | $CO_2Me$ |
| Me | OH | $CO_2Me$ |
| cyclopropylmethyl | OH | $CO_2Me$ |
| cyclobutylmethyl | OH | $CO_2Me$ |
| benzyl | OH | $CO_2Me$ |
| 2-phenethyl | OH | $CO_2Me$ |
| allyl | OH | $CO_2Me$ |
| acetyl | OH | $CO_2Me$ |
| H | $OCH_3$ | $CO_2Me$ |
| Me | $OCH_3$ | $CO_2Me$ |
| cyclopropylmethyl | $OCH_3$ | $CO_2Me$ |
| cyclobutylmethyl | $OCH_3$ | $CO_2Me$ |
| benzyl | $OCH_3$ | $CO_2Me$ |
| 2-phenethyl | $OCH_3$ | $CO_2Me$ |
| allyl | $OCH_3$ | $CO_2Me$ |
| acetyl | $OCH_3$ | $CO_2Me$ |
| H | OH | $CO_2Et$ |
| Me | OH | $CO_2Et$ |
| cyclopropylmethyl | OH | $CO_2Et$ |
| cyclobutylmethyl | OH | $CO_2Et$ |
| benzyl | OH | $CO_2Et$ |
| 2-phenethyl | OH | $CO_2Et$ |
| allyl | OH | $CO_2Et$ |
| acetyl | OH | $CO_2Et$ |
| H | $OCH_3$ | $CO_2Et$ |
| Me | $OCH_3$ | $CO_2Et$ |
| cyclopropylmethyl | $OCH_3$ | $CO_2Et$ |
| cyclobutylmethyl | $OCH_3$ | $CO_2Et$ |
| benzyl | $OCH_3$ | $CO_2Et$ |
| 2-phenethyl | $OCH_3$ | $CO_2Et$ |
| allyl | $OCH_3$ | $CO_2Et$ |
| acetyl | $OCH_3$ | $CO_2Et$ |
| H | OH | $CO_2Ph$ |
| Me | OH | $CO_2Ph$ |
| cyclopropylmethyl | OH | $CO_2Ph$ |
| cyclobutylmethyl | OH | $CO_2Ph$ |
| benzyl | OH | $CO_2Ph$ |
| 2-phenethyl | OH | $CO_2Ph$ |

-continued

| | | |
|---|---|---|
| allyl | OH | $CO_2Ph$ |
| acetyl | OH | $CO_2Ph$ |
| H | $OCH_3$ | $CO_2Ph$ |
| Me | $OCH_3$ | $CO_2Ph$ |
| cyclopropylmethyl | $OCH_3$ | $CO_2Ph$ |
| cyclobutylmethyl | $OCH_3$ | $CO_2Ph$ |
| benzyl | $OCH_3$ | $CO_2Ph$ |
| 2-phenethyl | $OCH_3$ | $CO_2Ph$ |
| allyl | $OCH_3$ | $CO_2Ph$ |
| acetyl | $OCH_3$ | $CO_2Ph$ |
| H | OH | $CO_2Bn$ |
| Me | OH | $CO_2Bn$ |
| cyclopropylmethyl | OH | $CO_2Bn$ |
| cyclobutylmethyl | OH | $CO_2Bn$ |
| benzyl | OH | $CO_2Bn$ |
| 2-phenethyl | OH | $CO_2Bn$ |
| allyl | OH | $CO_2Bn$ |
| acetyl | OH | $CO_2Bn$ |
| H | $OCH_3$ | $CO_2Bn$ |
| Me | $OCH_3$ | $CO_2Bn$ |
| cyclopropylmethyl | $OCH_3$ | $CO_2Bn$ |
| cyclobutylmethyl | $OCH_3$ | $CO_2Bn$ |
| benzyl | $OCH_3$ | $CO_2Bn$ |
| 2-phenethyl | $OCH_3$ | $CO_2Bn$ |
| allyl | $OCH_3$ | $CO_2Bn$ |
| acetyl | $OCH_3$ | $CO_2Bn$ |
| H | OH | $CONH_2$ |
| Me | OH | $CONH_2$ |
| cyclopropylmethyl | OH | $CONH_2$ |
| cyclobutylmethyl | OH | $CONH_2$ |
| benzyl | OH | $CONH_2$ |
| 2-phenethyl | OH | $CONH_2$ |
| allyl | OH | $CONH_2$ |
| acetyl | OH | $CONH_2$ |
| H | $OCH_3$ | $CONH_2$ |
| Me | $OCH_3$ | $CONH_2$ |
| cyclopropylmethyl | $OCH_3$ | $CONH_2$ |
| cyclobutylmethyl | $OCH_3$ | $CONH_2$ |
| benzyl | $OCH_3$ | $CONH_2$ |
| 2-phenethyl | $OCH_3$ | $CONH_2$ |
| allyl | $OCH_3$ | $CONH_2$ |
| acetyl | $OCH_3$ | $CONH_2$ |
| H | OH | CONHMe |
| Me | OH | CONHMe |
| cyclopropylmethyl | OH | CONHMe |
| cyclobutylmethyl | OH | CONHMe |
| benzyl | OH | CONHMe |
| 2-phenethyl | OH | CONHMe |
| allyl | OH | CONHMe |
| acetyl | OH | CONHMe |
| H | $OCH_3$ | CONHMe |
| Me | $OCH_3$ | CONHMe |
| cyclopropylmethyl | $OCH_3$ | CONHMe |
| cyclobutylmethyl | $OCH_3$ | CONHMe |
| benzyl | $OCH_3$ | CONHMe |
| 2-phenethyl | $OCH_3$ | CONHMe |
| allyl | $OCH_3$ | CONHMe |
| acetyl | $OCH_3$ | CONHMe |
| H | OH | CONHPh |
| Me | OH | CONHPh |
| cyclopropylmethyl | OH | CONHPh |
| cyclobutylmethyl | OH | CONHPh |
| benzyl | OH | CONHPh |
| 2-phenethyl | OH | CONHPh |
| allyl | OH | CONHPh |
| acetyl | OH | CONHPh |
| H | $OCH_3$ | CONHPh |
| Me | $OCH_3$ | CONHPh |
| cyclopropylmethyl | $OCH_3$ | CONHPh |
| cyclobutylmethyl | $OCH_3$ | CONHPh |
| benzyl | $OCH_3$ | CONHPh |
| 2-phenethyl | $OCH_3$ | CONHPh |
| allyl | $OCH_3$ | CONHPh |
| acetyl | $OCH_3$ | CONHPh |
| H | OH | CONHBn |
| Me | OH | CONHBn |
| cyclopropylmethyl | OH | CONHBn |
| cyclobutylmethyl | OH | CONHBn |

-continued

| | | |
|---|---|---|
| benzyl | OH | CONHBn |
| 2-phenethyl | OH | CONHBn |
| allyl | OH | CONHBn |
| acetyl | OH | CONHBn |
| H | $OCH_3$ | CONHBn |
| Me | $OCH_3$ | CONHBn |
| cyclopropylmethyl | $OCH_3$ | CONHBn |
| cyclobutylmethyl | $OCH_3$ | CONHBn |
| benzyl | $OCH_3$ | CONHBn |
| 2-phenethyl | $OCH_3$ | CONHBn |
| allyl | $OCH_3$ | CONHBn |
| acetyl | $OCH_3$ | CONHBn |
| H | OH | $CONMe_2$ |
| Me | OH | $CONMe_2$ |
| cyclopropylmethyl | OH | $CONMe_2$ |
| cyclobutylmethyl | OH | $CONMe_2$ |
| benzyl | OH | $CONMe_2$ |
| 2-phenethyl | OH | $CONMe_2$ |
| allyl | OH | $CONMe_2$ |
| acetyl | OH | $CONMe_2$ |
| H | $OCH_3$ | $CONMe_2$ |
| Me | $OCH_3$ | $CONMe_2$ |
| cyclopropylmethyl | $OCH_3$ | $CONMe_2$ |
| cyclobutylmethyl | $OCH_3$ | $CONMe_2$ |
| benzyl | $OCH_3$ | $CONMe_2$ |
| 2-phenethyl | $OCH_3$ | $CONMe_2$ |
| allyl | $OCH_3$ | $CONMe_2$ |
| acetyl | $OCH_3$ | $CONMe_2$ |

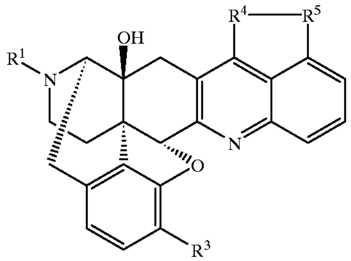

| $R^1$ | $R^3$ | $R^{4-R5}$ |
|---|---|---|
| H | OH | NHCO |
| Me | OH | NHCO |
| cyclopropylmethyl | OH | NHCO |
| cyclobutylmethyl | OH | NHCO |
| benzyl | OH | NHCO |
| 2-phenethyl | OH | NHCO |
| allyl | OH | NHCO |
| acetyl | OH | NHCO |
| H | $OCH_3$ | NHCO |
| Me | $OCH_3$ | NHCO |
| cyclopropylmethyl | $OCH_3$ | NHCO |
| cyclobutylmethyl | $OCH_3$ | NHCO |
| benzyl | $OCH_3$ | NHCO |
| 2-phenethyl | $OCH_3$ | NHCO |
| allyl | $OCH_3$ | NHCO |
| acetyl | $OCH_3$ | NHCO |
| H | OH | N(Me)CO |
| Me | OH | N(Me)CO |
| cyclopropylmethyl | OH | N(Me)CO |
| cyclobutylmethyl | OH | N(Me)CO |
| benzyl | OH | N(Me)CO |
| 2-phenethyl | OH | N(Me)CO |
| allyl | OH | N(Me)CO |
| acetyl | OH | N(Me)CO |
| H | $OCH_3$ | N(Me)CO |
| Me | $OCH_3$ | N(Me)CO |
| cyclopropylmethyl | $OCH_3$ | N(Me)CO |
| cyclobutylmethyl | $OCH_3$ | N(Me)CO |
| benzyl | $OCH_3$ | N(Me)CO |
| 2-phenethyl | $OCH_3$ | N(Me)CO |
| allyl | $OCH_3$ | N(Me)CO |
| acetyl | $OCH_3$ | N(Me)CO |
| H | OH | N(Et)CO |

-continued

| | | |
|---|---|---|
| Me | OH | N(Et)CO |
| cyclopropylmethyl | OH | N(Et)CO |
| cyclobutylmethyl | OH | N(Et)CO |
| benzyl | OH | N(Et)CO |
| 2-phenethyl | OH | N(Et)CO |
| allyl | OH | N(Et)CO |
| acetyl | OH | N(Et)CO |
| H | $OCH_3$ | N(Et)CO |
| Me | $OCH_3$ | N(Et)CO |
| cyclopropylmethyl | $OCH_3$ | N(Et)CO |
| cyclobutylmethyl | $OCH_3$ | N(Et)CO |
| benzyl | $OCH_3$ | N(Et)CO |
| 2-phenethyl | $OCH_3$ | N(Et)CO |
| allyl | $OCH_3$ | N(Et)CO |
| acetyl | $OCH_3$ | N(Et)CO |
| H | OH | N(Bn)CO |
| Me | OH | N(Bn)CO |
| cyclopropylmethyl | OH | N(Bn)CO |
| cyclobutylmethyl | OH | N(Bn)CO |
| benzyl | OH | N(Bn)CO |
| 2-phenethyl | OH | N(Bn)CO |
| allyl | OH | N(Bn)CO |
| acetyl | OH | N(Bn)CO |
| H | $OCH_3$ | N(Bn)CO |
| Me | $OCH_3$ | N(Bn)CO |
| cyclopropylmethyl | $OCH_3$ | N(Bn)CO |
| cyclobutylmethyl | $OCH_3$ | N(Bn)CO |
| benzyl | $OCH_3$ | N(Bn)CO |
| 2-phenethyl | $OCH_3$ | N(Bn)CO |
| allyl | $OCH_3$ | N(Bn)CO |
| acetyl | $OCH_3$ | N(Bn)CO |
| H | OH | N(Ac)CO |
| Me | OH | N(An)CO |
| cyclopropylmethyl | OH | N(Ac)CO |
| cyclobutylmethyl | OH | N(Ac)CO |
| benzyl | OH | N(Ac)CO |
| 2-phenethyl | OH | N(Ac)CO |
| allyl | OH | N(Ac)CO |
| acetyl | OH | N(Ac)CO |
| H | $OCH_3$ | N(Ac)CO |
| Me | $OCH_3$ | N(Ac)CO |
| cyclopropylmethyl | $OCH_3$ | N(Ac)CO |
| cyclobutylmethyl | $OCH_3$ | N(Ac)CO |
| benzyl | $OCH_3$ | N(Ac)CO |
| 2-phenethyl | $OCH_3$ | N(Ac)CO |
| allyl | $OCH_3$ | N(Ac)CO |
| acetyl | $OCH_3$ | N(Ac)CO |
| H | OH | NHC(=NH) |
| Me | OH | NHC(=NH) |
| cyclopropylmethyl | OH | NHC(=NH) |
| cyclobutylmethyl | OH | NHC(=NH) |
| benzyl | OH | NHC(=NH) |
| 2-phenethyl | OH | NHC(=NH) |
| allyl | OH | NHC(=NH) |
| acetyl | OH | NHC(=NH) |
| H | $OCH_3$ | NHC(=NH) |
| Me | $OCH_3$ | NHC(=NH) |
| cyclopropylmethyl | $OCH_3$ | NHC(=NH) |
| cyclobutylmethyl | $OCH_3$ | NHC(=NH) |
| benzyl | $OCH_3$ | NHC(=NH) |
| 2-phenethyl | $OCH_3$ | NHC(=NH) |
| allyl | $OCH_3$ | NHC(=NH) |
| acetyl | $OCH_3$ | NHC(=NH) |
| H | OH | N(Me)C(=NH) |
| Me | OH | N(Me)C(=NH) |
| cyclopropylmethyl | OH | N(Me)C(=NH) |
| cyclobutylmethyl | OH | N(Me)C(=NH) |
| benzyl | OH | N(Me)C(=NH) |
| 2-phenethyl | OH | N(Me)C(=NH) |
| allyl | OH | N(Me)C(=NH) |
| acetyl | OH | N(Me)C(=NH) |
| H | $OCH_3$ | N(Me)C(=NH) |
| Me | $OCH_3$ | N(Me)C(=NH) |
| cyclopropylmethyl | $OCH_3$ | N(Me)C(=NH) |
| cyclobutylmethyl | $OCH_3$ | N(Me)C(=NH) |
| benzyl | $OCH_3$ | N(Me)C(=NH) |
| 2-phenethyl | $OCH_3$ | N(Me)C(=NH) |
| allyl | $OCH_3$ | N(Me)C(=NH) |

-continued

| | | |
|---|---|---|
| acetyl | $OCH_3$ | N(Me)C(=NH) |
| H | OH | N(Et)C(=NH) |
| Me | OH | N(Et)C(=NH) |
| cyclopropylmethyl | OH | N(Et)C(=NH) |
| cyclobutylmethyl | OH | N(Et)C(=NH) |
| benzyl | OH | N(Et)C(=NH) |
| 2-phenethyl | OH | N(Et)C(=NH) |
| allyl | OH | N(Et)C(=NH) |
| acetyl | OH | N(Et)C(=NH) |
| H | $OCH_3$ | N(Et)C(=NH) |
| Me | $OCH_3$ | N(Et)C(=NH) |
| cyclopropylmethyl | $OCH_3$ | N(Et)C(=NH) |
| cyclobutylmethyl | $OCH_3$ | N(Et)C(=NH) |
| benzyl | $OCH_3$ | N(Et)C(=NH) |
| 2-phenethyl | $OCH_3$ | N(Et)C(=NH) |
| allyl | $OCH_3$ | N(Et)C(=NH) |
| acetyl | $OCH_3$ | N(Et)C(=NH) |
| H | OH | $NHCH_2$ |
| Me | OH | $NHCH_2$ |
| cyclopropylmethyl | OH | $NHCH_2$ |
| cyclobutylmethyl | OH | $NHCH_2$ |
| benzyl | OH | $NHCH_2$ |
| 2-phenethyl | OH | $NHCH_2$ |
| allyl | OH | $NHCH_2$ |
| acetyl | OH | $NHCH_2$ |
| H | $OCH_3$ | $NHCH_2$ |
| Me | $OCH_3$ | $NHCH_2$ |
| cyclopropylmethyl | $OCH_3$ | $NHCH_2$ |
| cyclobutylmethyl | $OCH_3$ | $NHCH_2$ |
| benzyl | $OCH_3$ | $NHCH_2$ |
| 2-phenethyl | $OCH_3$ | $NHCH_2$ |
| allyl | $OCH_3$ | $NHCH_2$ |
| acetyl | $OCH_3$ | $NHCH_2$ |
| H | OH | $N(Me)CH_2$ |
| Me | OH | $N(Me)CH_2$ |
| cyclopropylmethyl | OH | $N(Me)CH_2$ |
| cyclobutylmethyl | OH | $N(Me)CH_2$ |
| benzyl | OH | $N(Me)CH_2$ |
| 2-phenethyl | OH | $N(Me)CH_2$ |
| allyl | OH | $N(Me)CH_2$ |
| acetyl | OH | $N(Me)CH_2$ |
| H | $OCH_3$ | $N(Me)CH_2$ |
| Me | $OCH_3$ | $N(Me)CH_2$ |
| cyclopropylmethyl | $OCH_3$ | $N(Me)CH_2$ |
| cyclobutylmethyl | $OCH_3$ | $N(Me)CH_2$ |
| benzyl | $OCH_3$ | $N(Me)CH_2$ |
| 2-phenethyl | $OCH_3$ | $N(Me)CH_2$ |
| allyl | $OCH_3$ | $N(Me)CH_2$ |
| acetyl | $OCH_3$ | $N(Me)CH_2$ |
| H | OH | benzeno |
| Me | OH | benzeno |
| cyclopropylmethyl | OH | benzeno |
| cyclobutylmethyl | OH | benzeno |
| benzyl | OH | benzeno |
| 2-phenethyl | OH | benzeno |
| allyl | OH | benzeno |
| acetyl | OH | benzeno |
| H | $OCH_3$ | benzeno |
| Me | $OCH_3$ | benzeno |
| cyclopropylmethyl | $OCH_3$ | benzeno |
| cyclobutylmethyl | $OCH_3$ | benzeno |
| benzyl | $OCH_3$ | benzeno |
| 2-phenethyl | $OCH_3$ | benzeno |
| allyl | $OCH_3$ | benzeno |
| acetyl | $OCH_3$ | benzeno |
| H | OH | propano |
| Me | OH | propano |
| cyclopropylmethyl | OH | propano |
| cyclobutylmethyl | OH | propano |
| benzyl | OH | propano |
| 2-phenethyl | OH | propano |
| allyl | OH | propano |
| acetyl | OH | propano |
| H | $OCH_3$ | propano |
| Me | $OCH_3$ | propano |
| cyclopropylmethyl | $OCH_3$ | propano |
| cyclobutylmethyl | $OCH_3$ | propano |
| benzyl | $OCH_3$ | propano |

-continued

| | | |
|---|---|---|
| 2-phenethyl | $OCH_3$ | propano |
| allyl | $OCH_3$ | propano |
| acetyl | $OCH_3$ | propano |

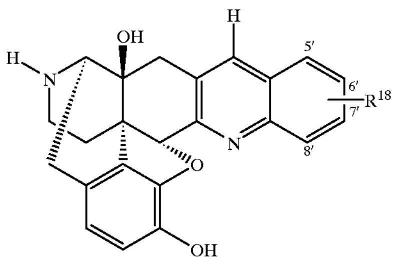

| $R^{16}$ | $R^{18}$ |
|---|---|
| 5'-F | 5'-NOS |
| 6'-F | 6'-NOS |
| 7'-F | 7'-NOS |
| 8'-F | 8'-NOS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

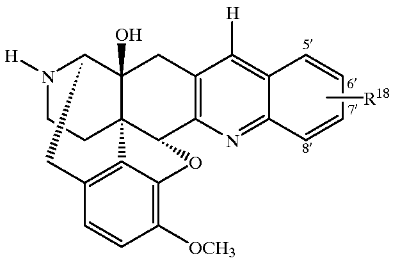

| $R^{16}$ | $R^{18}$ |
|---|---|
| 5'-F | 5'-NOS |
| 6'-F | 6'-NOS |
| 7'-F | 7'-NOS |
| 8'-F | 8'-NOS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

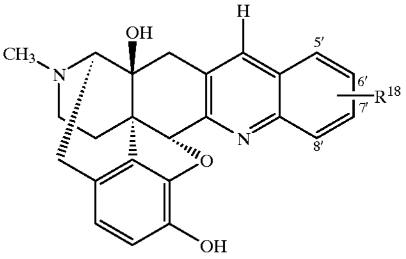

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$OC_2H$ |
| 6'-Et | 6'-$OC_2H$ |
| 7'-Et | 7'-$OC_2H$ |
| 8'-Et | 8'-$OC_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

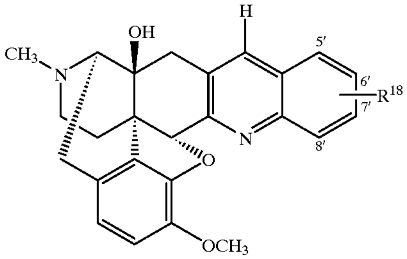

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

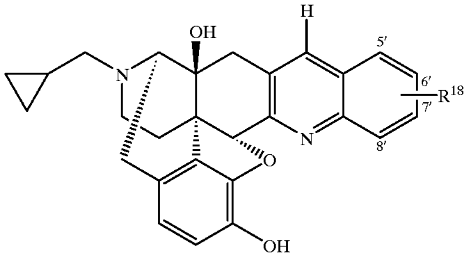

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

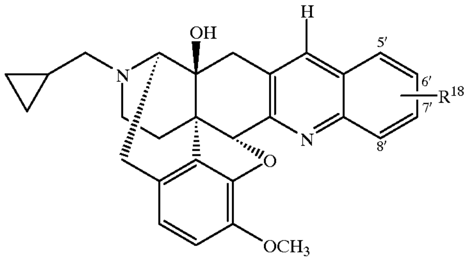

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

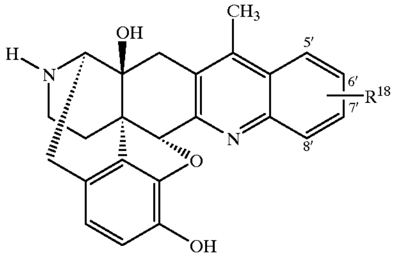

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

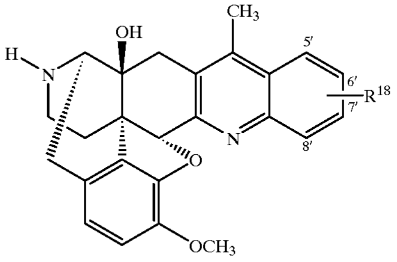

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

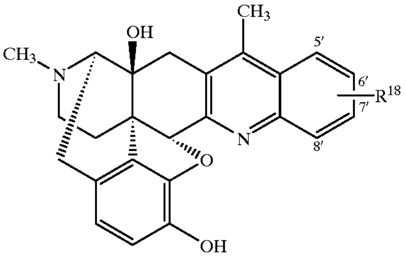

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

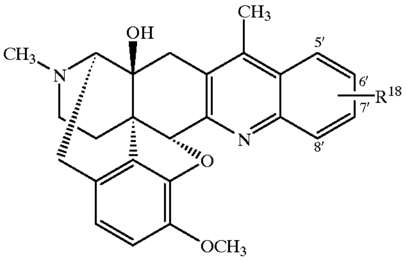

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

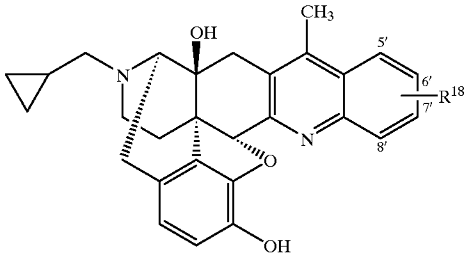

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

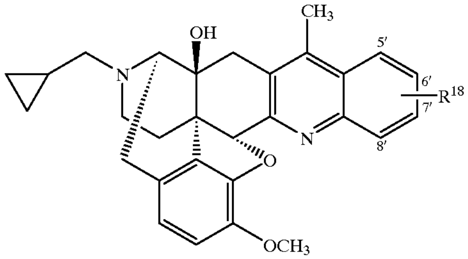

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

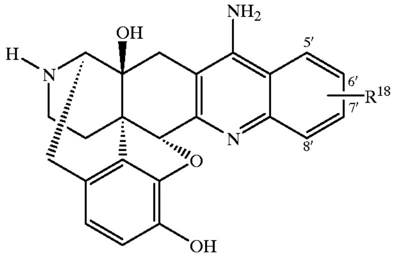

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

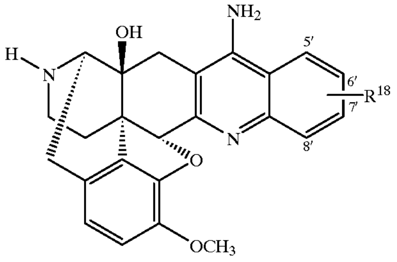

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

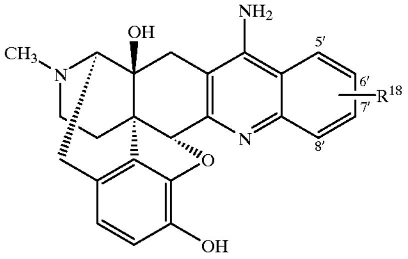

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

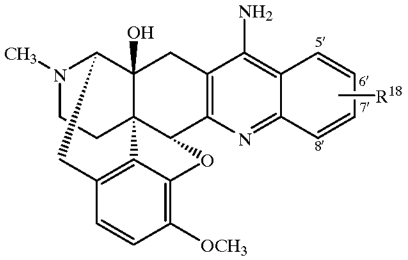

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$CF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

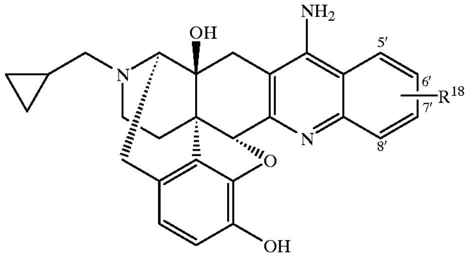

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

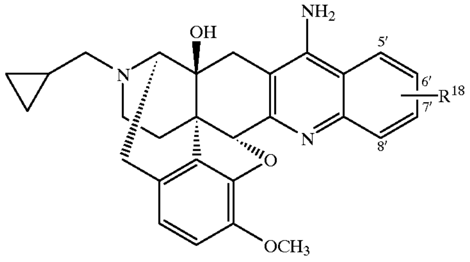

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

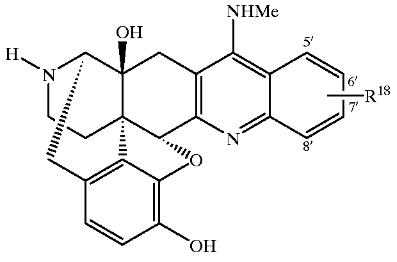

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

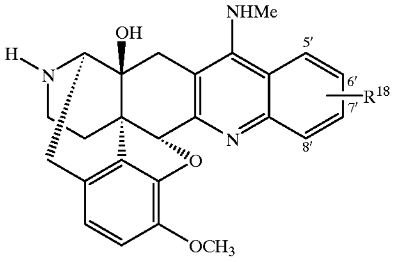

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

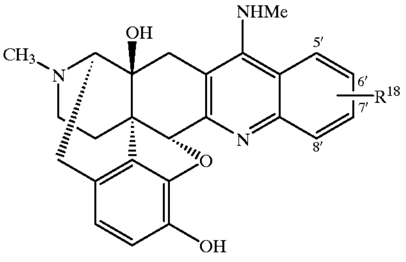

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

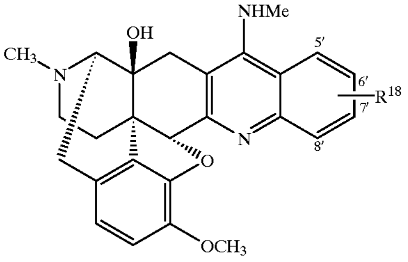

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

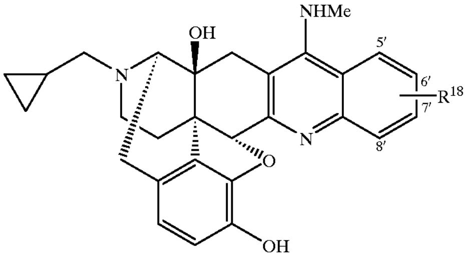

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-SCaMe |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

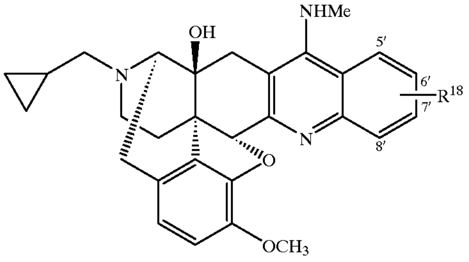

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

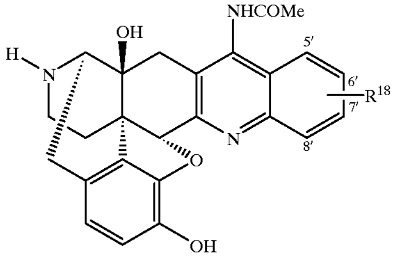

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

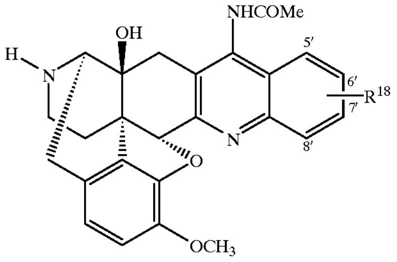

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

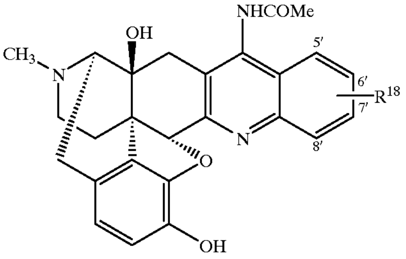

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

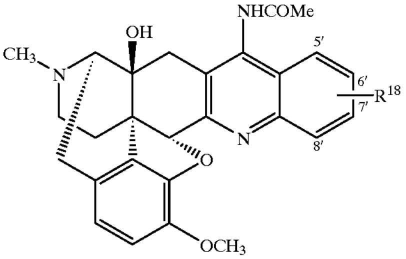

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$CCF_3$ |
| 8'-Br | 8'-$CCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

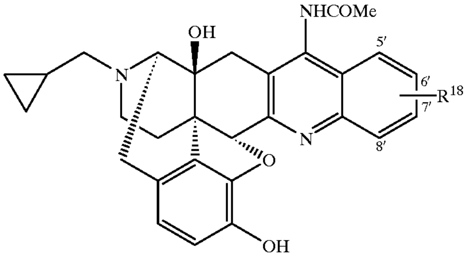

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

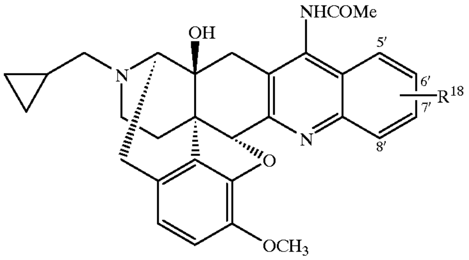

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

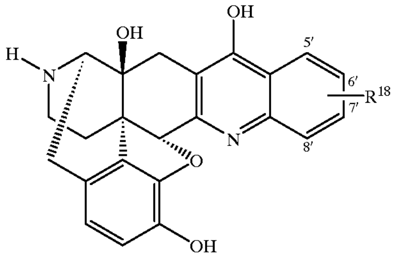

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

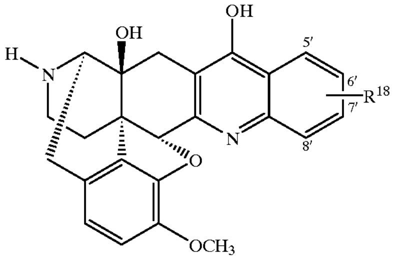

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

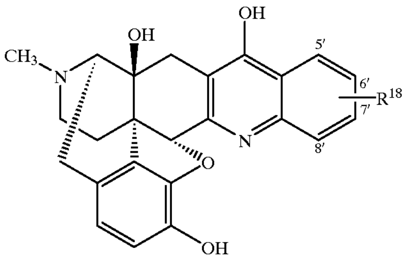

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 6'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

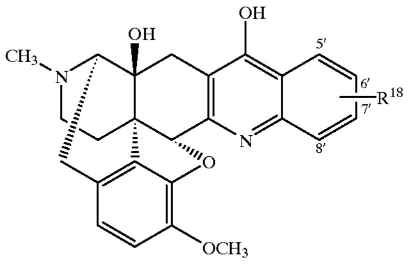

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

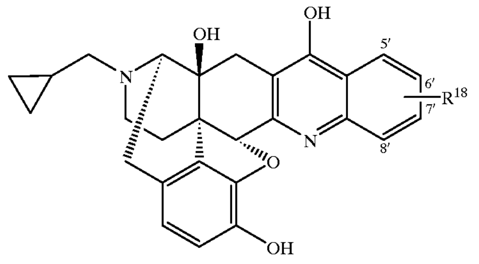

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

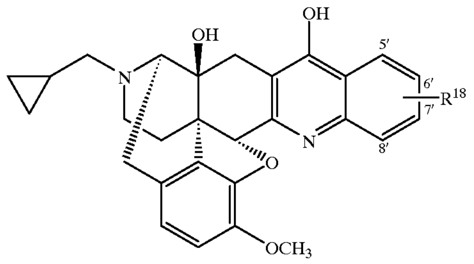

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

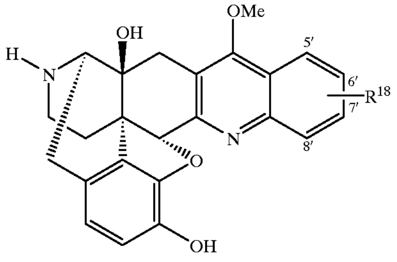

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

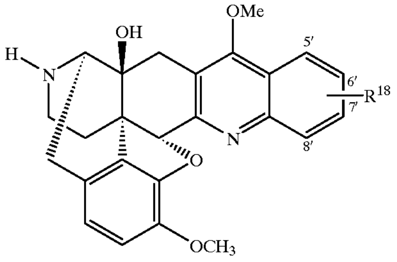

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

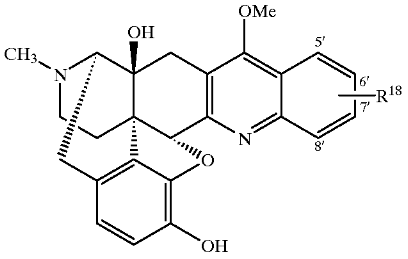

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

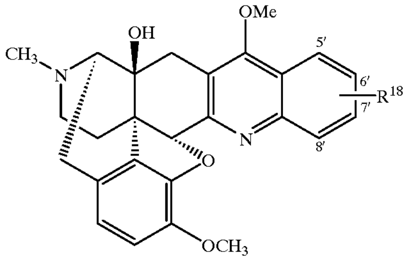

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2Me$ |
| 6'-Me | 6'-$SO_2Me$ |
| 7'-Me | 7'-$SO_2Me$ |
| 8'-Me | 8'-$SO_2Me$ |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

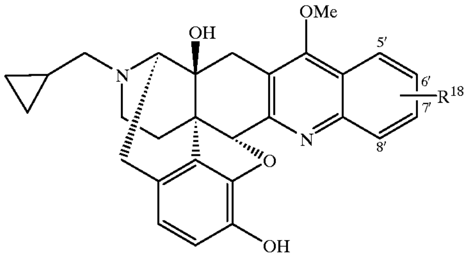

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

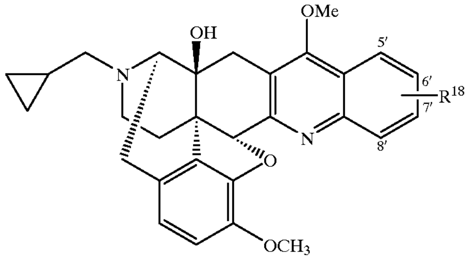

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2$H |
| 6'-Et | 6'-$CO_2$H |
| 7'-Et | 7'-$CO_2$H |
| 8'-Et | 8'-$CO_2$H |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2$OH |
| 6'-Bu | 6'-$CH_2$OH |
| 7'-Bu | 7'-$CH_2$OH |
| 8'-Bu | 8'-$CH_2$OH |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

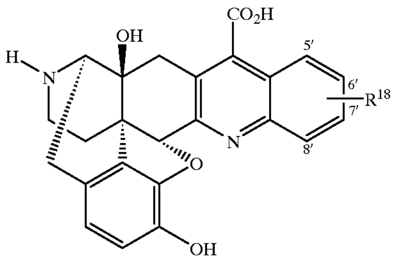

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

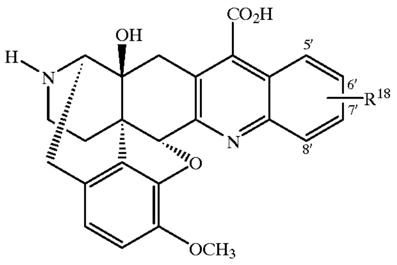

| $R^{16}$ | $R^{18}$ |
|---|---|
| 5'-F | 5'-NCS |
| 6'-F | 6'-NCS |
| 7'-F | 7'-NCS |
| 8'-F | 8'-NCS |
| 5'-Cl | 5'-$CF_3$ |
| 6'-Cl | 6'-$CF_3$ |
| 7'-Cl | 7'-$CF_3$ |
| 8'-Cl | 8'-$CF_3$ |
| 5'-Br | 5'-$OCF_3$ |
| 6'-Br | 6'-$OCF_3$ |
| 7'-Br | 7'-$OCF_3$ |
| 8'-Br | 8'-$OCF_3$ |
| 5'-I | 5'-CN |
| 6'-I | 6'-CN |
| 7'-I | 7'-CN |
| 8'-I | 8'-CN |
| 5'-$NO_2$ | 5'-Ph |
| 6'-$NO_2$ | 6'-Ph |
| 7'-$NO_2$ | 7'-Ph |
| 8'-$NO_2$ | 8'-Ph |
| 5'-OH | 5'-SMe |
| 6'-OH | 6'-SMe |
| 7'-OH | 7'-SMe |
| 8'-OH | 8'-SMe |
| 5'-Me | 5'-$SO_2$Me |
| 6'-Me | 6'-$SO_2$Me |
| 7'-Me | 7'-$SO_2$Me |
| 8'-Me | 8'-$SO_2$Me |
| 5'-Et | 5'-$CO_2H$ |
| 6'-Et | 6'-$CO_2H$ |
| 7'-Et | 7'-$CO_2H$ |
| 8'-Et | 8'-$CO_2H$ |
| 5'-Pr | 5'-$NH_2$ |
| 6'-Pr | 6'-$NH_2$ |
| 7'-Pr | 7'-$NH_2$ |
| 8'-Pr | 8'-$NH_2$ |
| 5'-Bu | 5'-$CH_2OH$ |
| 6'-Bu | 6'-$CH_2OH$ |
| 7'-Bu | 7'-$CH_2OH$ |
| 8'-Bu | 8'-$CH_2OH$ |
| 5'-OMe | 5'-$CONH_2$ |
| 6'-OMe | 6'-$CONH_2$ |
| 7'-OMe | 7'-$CONH_2$ |
| 8'-OMe | 8'-$CONH_2$ |
| 5'-OEt | 5'-NHMe |
| 6'-OEt | 6'-NHMe |

-continued

| | |
|---|---|
| 7'-OEt | 7'-NHMe |
| 8'-OEt | 8'-NHMe |

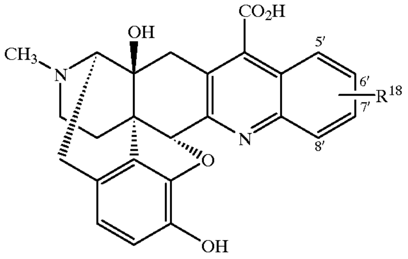

| $R^{16}$ | $R^{18}$ |
|---|---|
| 5'-F | 6'-Ph |
| 6'-F | 7'-Ph |
| 7'-F | 8'-Ph |
| 8'-F | 6'-SMe |
| 5'-Cl | 7'-SMe |
| 6'-Cl | 8'-SMe |
| 7'-Cl | 6'-$SO_2$Me |
| 8'-Cl | 7'-$SO_2$Me |
| 5'-Br | 8'-$SO_2$Me |
| 6'-Br | 6'-$CO_2$H |
| 7'-Br | 7'-$CO_2$H |
| 8'-Br | 8'-$CO_2$H |
| 5'-I | 6'-$NH_2$ |
| 6'-I | 7'-$NH_2$ |
| 7'-I | 8'-$NH_2$ |
| 8'-I | 6'-$CH_2$OH |
| 5'-$NO_2$ | 7'-$CH_2$OH |
| 6'-$NO_2$ | 8'-$CH_2$OH |
| 7'-$NO_2$ | 6'-$CONH_2$ |
| 8'-$NO_2$ | 7'-$CONH_2$ |
| 5'-OH | 8'-$CONH_2$ |
| 6'-OH | 6'-NHMe |
| 7'-OH | 7'-NHMe |
| 8'-OH | 8'-NHMe |
| 5'-Me | 6'-$CO_2$Me |
| 6'-Me | 7'-$CO_2$Me |
| 7'-Me | 8'-$CO_2$Me |
| 8'-Me | 6'-$CH_2CO_2$H |
| 5'-Et | 7'-$CH_2CO_2$H |
| 6'-Et | 8'-$CH_2CO_2$H |
| 7'-Et | 6'-$SO_2NH_2$ |
| 8'-Et | 7'-$SO_2NH_2$ |
| 5'-Pr | 8'-$SO_2NH_2$ |
| 6'-Pr | 6'-$SO_2$NHMe |
| 7'-Pr | 7'-$SO_2$NHMe |
| 8'-Pr | 8'-$SO_2$NHMe |
| 5'-Bu | 6'-CONHMe |
| 6'-Bu | 7'-CONHMe |
| 7'-Bu | 8'-CONHMe |
| 8'-Bu | 6'-$NMe_2$ |
| 5'-OMe | 7'-$NMe_2$ |
| 6'-OMe | 8'-$NMe_2$ |
| 7'-OMe | 6'-$CH_2NH_2$ |
| 8'-OMe | 7'-$CH_2NH_2$ |
| 5'-OEt | 8'-$CH_2NH_2$ |
| 6'-OEt | 6'-NHCHO |

-continued

| | |
|---|---|
| 7'-OEt | 7'-NHCHO |
| 8'-OEt | 8'-NHCHO |

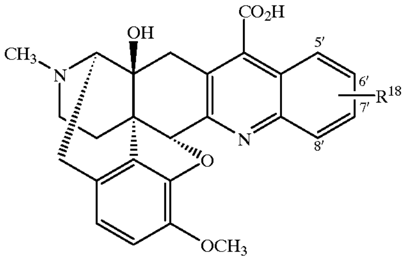

| $R^{16}$ | $R^{18}$ |
|---|---|
| 5'-F | 6'-Ph |
| 6'-F | 7'-Ph |
| 7'-F | 8'-Ph |
| 8'-F | 6'-SMe |
| 5'-Cl | 7'-SMe |
| 6'-Cl | 8'-SMe |
| 7'-Cl | 6'-$SO_2$Me |
| 8'-Cl | 7'-$SO_2$Me |
| 5'-Br | 8'-$SO_2$Me |
| 6'-Br | 6'-$CO_2$H |
| 7'-Br | 7'-$CO_2$H |
| 8'-Br | 8'-$CO_2$H |
| 5'-I | 6'-$NH_2$ |
| 6'-I | 7'-$NH_2$ |
| 7'-I | 8'-$NH_2$ |
| 8'-I | 6'-$CH_2$OH |
| 5'-$NO_2$ | 7'-$CH_2$OH |
| 6'-$NO_2$ | 8'-$CH_2$OH |
| 7'-$NO_2$ | 6'-$CONH_2$ |
| 8'-$NO_2$ | 7'-$CONH_2$ |
| 5'-OH | 8'-$CONH_2$ |
| 6'-OH | 6'-NHMe |
| 7'-OH | 7'-NHMe |
| 8'-OH | 8'-NHMe |
| 5'-Me | 6'-$CO_2$Me |
| 6'-Me | 7'-$CO_2$Me |
| 7'-Me | 8'-$CO_2$Me |
| 8'-Me | 6'-$CH_2CO_2$H |
| 5'-Et | 7'-$CH_2CO_2$H |
| 6'-Et | 8'-$CH_2CO_2$H |
| 7'-Et | 6'-$SO_2NH_2$ |
| 8'-Et | 7'-$SO_2NH_2$ |
| 5'-Pr | 8'-$SO_2NH_2$ |
| 6'-Pr | 6'-$SO_2$NHMe |
| 7'-Pr | 7'-$SO_2$NHMe |
| 8'-Pr | 8'-$SO_2$NHMe |
| 5'-Bu | 6'-CONHMe |
| 6'-Bu | 7'-CONHMe |
| 7'-Bu | 8'-CONHMe |
| 8'-Bu | 6'-$NMe_2$ |
| 5'-OMe | 7'-$NMe_2$ |
| 6'-OMe | 8'-$NMe_2$ |
| 7'-OMe | 6'-$CH_2NH_2$ |
| 8'-OMe | 7'-$CH_2NH_2$ |
| 5'-OEt | 8'-$CH_2NH_2$ |
| 6'-OEt | 6'-NHCHO |

-continued

| | |
|---|---|
| 7'-OEt | 7'-NHCHO |
| 8'-OEt | 8'-NHCHO |

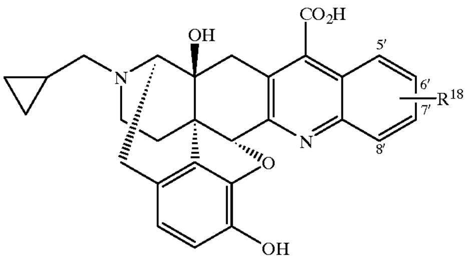

| $R^{16}$ | $R^{18}$ |
|---|---|
| 5'-F | 6'-Ph |
| 6'-F | 7'-Ph |
| 7'-F | 8'-Ph |
| 8'-F | 6'-SMe |
| 5'-Cl | 7'-SMe |
| 6'-Cl | 8'-SMe |
| 7'-Cl | 6'-$SO_2$Me |
| 8'-Cl | 7'-$SO_2$Me |
| 5'-Br | 8'-$SO_2$Me |
| 6'-Br | 6'-$CO_2H$ |
| 7'-Br | 7'-$CO_2H$ |
| 8'-Br | 8'-$CO_2H$ |
| 5'-I | 6'-$NH_2$ |
| 6'-I | 7'-$NH_2$ |
| 7'-I | 8'-$NH_2$ |
| 8'-I | 6'-$CH_2OH$ |
| 5'-$NO_2$ | 7'-$CH_2OH$ |
| 6'-$NO_2$ | 8'-$CH_2OH$ |
| 7'-$NO_2$ | 6'-$CONH_2$ |
| 8'-$NO_2$ | 7'-$CONH_2$ |
| 5'-OH | 8'-$CONH_2$ |
| 6'-OH | 6'-NHMe |
| 7'-OH | 7'-NHMe |
| 8'-OH | 8'-NHMe |
| 5'-Me | 6'-$CO_2$Me |
| 6'-Me | 7'-$CO_2$Me |
| 7'-Me | 8'-$CO_2$Me |
| 8'-Me | 6'-$CH_2CO_2H$ |
| 5'-Et | 7'-$CH_2CO_2H$ |
| 6'-Et | 8'-$CH_2CO_2H$ |
| 7'-Et | 6'-$SO_2NH_2$ |
| 8'-Et | 7'-$SO_2NH_2$ |
| 5'-Pr | 8'-$SO_2NH_2$ |
| 6'-Pr | 6'-$SO_2$NHMe |
| 7'-Pr | 7'-$SO_2$NHMe |
| 8'-Pr | 8'-$SO_2$NHMe |
| 5'-Bu | 6'-CONHMe |
| 6'-Bu | 7'-CONHMe |
| 7'-Bu | 8'-CONHMe |
| 8'-Bu | 6'-$NMe_2$ |
| 5'-OMe | 7'-$NMe_2$ |
| 6'-OMe | 8'-$NMe_2$ |
| 7'-OMe | 6'-$CH_2NH_2$ |
| 8'-OMe | 7'-$CH_2NH_2$ |
| 5'-OEt | 8'-$CH_2NH_2$ |
| 6'-OEt | 6'-NHCHO |
| 7'-OEt | 7'-NHCHO |
| 8'-OEt | 8'-NHCHO |

-continued

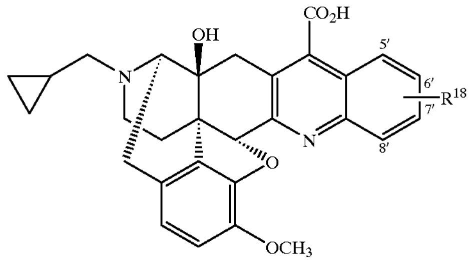

| $R^{16}$ | $R^{18}$ |
|---|---|
| 5'-F | 6'-Ph |
| 6'-F | 7'-Ph |
| 7'-F | 8'-Ph |
| 8'-F | 6'-SMe |
| 5'-Cl | 7'-SMe |
| 6'-Cl | 8'-SMe |
| 7'-Cl | 6'-$SO_2$Me |
| 8'-Cl | 7'-$SO_2$Me |
| 5'-Br | 8'-$SO_2$Me |
| 6'-Br | 6'-$CO_2H$ |
| 7'-Br | 7'-$CO_2H$ |
| 8'-Br | 8'-$CO_2H$ |
| 5'-I | 6'-$NH_2$ |
| 6'-I | 7'-$NH_2$ |
| 7'-I | 8'-$NH_2$ |
| 8'-I | 6'-$CH_2OH$ |
| 5'-$NO_2$ | 7'-$CH_2OH$ |
| 6'-$NO_2$ | 8'-$CH_2OH$ |
| 7'-$NO_2$ | 6'-$CONH_2$ |
| 8'-$NO_2$ | 7'-$CONH_2$ |
| 5'-OH | 8'-$CONH_2$ |
| 6'-OH | 6'-NHMe |
| 7'-OH | 7'-NHMe |
| 8'-OH | 8'-NHMe |
| 5'-Me | 6'-$CO_2$Me |
| 6'-Me | 7'-$CO_2$Me |
| 7'-Me | 8'-$CO_2$Me |
| 8'-Me | 6'-$CH_2CO_2H$ |
| 5'-Et | 7'-$CH_2CO_2H$ |
| 6'-Et | 8'-$CH_2CO_2H$ |
| 7'-Et | 6'-$SO_2NH_2$ |
| 8'-Et | 7'-$SO_2NH_2$ |
| 5'-Pr | 8'-$SO_2NH_2$ |
| 6'-Pr | 6'-$SO_2$NHMe |
| 7'-Pr | 7'-$SO_2$NHMe |
| 8'-Pr | 8'-$SO_2$NHMe |
| 5'-Bu | 6'-CONHMe |
| 6'-Bu | 7'-CONHMe |
| 7'-Bu | 8'-CONHMe |
| 8'-Bu | 6'-$NMe_2$ |
| 5'-OMe | 7'-$NMe_2$ |
| 6'-OMe | 8'-$NMe_2$ |
| 7'-OMe | 6'-$CH_2NH_2$ |
| 8'-OMe | 7'-$CH_2NH_2$ |
| 5'-OEt | 8'-$CH_2NH_2$ |
| 6'-OEt | 6'-NHCHO |
| 7'-OEt | 7'-NHCHO |
| 8'-OEt | 8'-NHCHO |

-continued

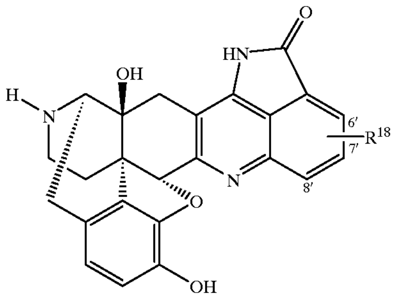

| $R^{16}$ | $R^{18}$ |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2$Me |
| 7'-Br | 7'-$SO_2$Me |
| 8'-Br | 8'-$SO_2$Me |
| 6'-I | 6'-$CO_2H$ |
| 7'-I | 7'-$CO_2H$ |
| 8'-I | 8'-$CO_2H$ |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2OH$ |
| 7'-OH | 7'-$CH_2OH$ |
| 8'-OH | 8'-$CH_2OH$ |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2$Me |
| 7'-Pr | 7'-$CO_2$Me |
| 8'-Pr | 8'-$CO_2$Me |
| 6'-Bu | 6'-$CH_2CO_2H$ |
| 7'-Bu | 7'-$CH_2CO_2H$ |
| 8'-Bu | 8'-$CH_2CO_2H$ |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2$NHMe |
| 7'-OEt | 7'-$SO_2$NHMe |
| 8'-OEt | 8'-$SO_2$NHMe |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

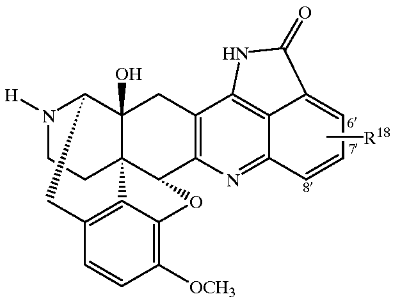

| $R^{16}$ | $R^{18}$ |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2$Me |
| 7'-Br | 7'-$SO_2$Me |
| 8'-Br | 8'-$SO_2$Me |
| 6'-I | 6'-$CO_2H$ |
| 7'-I | 7'-$CO_2H$ |
| 8'-I | 8'-$CO_2H$ |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2OH$ |
| 7'-OH | 7'-$CH_2OH$ |
| 8'-OH | 8'-$CH_2OH$ |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2$Me |
| 7'-Pr | 7'-$CO_2$Me |
| 8'-Pr | 8'-$CO_2$Me |
| 6'-Bu | 6'-$CH_2CO_2H$ |
| 7'-Bu | 7'-$CH_2CO_2H$ |
| 8'-Bu | 8'-$CH_2CO_2H$ |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2$NHMe |
| 7'-OEt | 7'-$SO_2$NHMe |
| 8'-OEt | 8'-$SO_2$NHMe |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

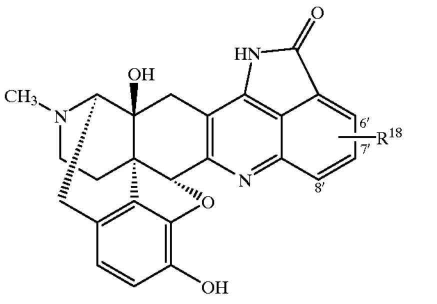

| $R^{16}$ | $R^{18}$ |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2Me$ |
| 7'-Br | 7'-$SO_2Me$ |
| 8'-Br | 8'-$SO_2Me$ |
| 6'-I | 6'-$CO_2H$ |
| 7'-I | 7'-$CO_2H$ |
| 8'-I | 8'-$CO_2H$ |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2OH$ |
| 7'-OH | 7'-$CH_2OH$ |
| 8'-OH | 8'-$CH_2OH$ |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2Me$ |
| 7'-Pr | 7'-$CO_2Me$ |
| 8'-Pr | 8'-$CO_2Me$ |
| 6'-Bu | 6'-$CH_2CO_2H$ |
| 7'-Bu | 7'-$CH_2CO_2H$ |
| 8'-Bu | 8'-$CH_2CO_2H$ |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2NHMe$ |
| 7'-OEt | 7'-$SO_2NHMe$ |
| 8'-OEt | 8'-$SO_2NHMe$ |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

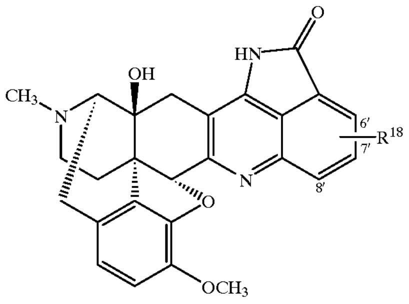

| $R^{16}$ | $R^{18}$ |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2Me$ |
| 7'-Br | 7'-$SO_2Me$ |
| 8'-Br | 8'-$SO_2Me$ |
| 6'-I | 6'-$CO_2H$ |
| 7'-I | 7'-$CO_2H$ |
| 8'-I | 8'-$CO_2H$ |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2OH$ |
| 7'-OH | 7'-$CH_2OH$ |
| 8'-OH | 8'-$CH_2OH$ |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2Me$ |
| 7'-Pr | 7'-$CO_2Me$ |
| 8'-Pr | 8'-$CO_2Me$ |
| 6'-Bu | 6'-$CH_2CO_2H$ |
| 7'-Bu | 7'-$CH_2CO_2H$ |
| 8'-Bu | 8'-$CH_2CO_2H$ |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2NHMe$ |
| 7'-OEt | 7'-$SO_2NHMe$ |
| 8'-OEt | 8'-$SO_2NHMe$ |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 5'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

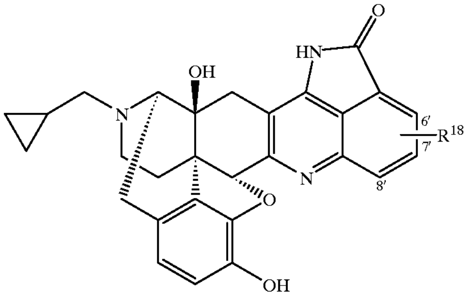

| R16 | R18 |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2$Me |
| 7'-Br | 7'-$SO_2$Me |
| 8'-Br | 8'-$SO_2$Me |
| 6'-I | 6'-$CO_2$H |
| 7'-I | 7'-$CO_2$H |
| 8'-I | 8'-$CO_2$H |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2$OH |
| 7'-OH | 7'-$CH_2$OH |
| 8'-OH | 8'-$CH_2$OH |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2$Me |
| 7'-Pr | 7'-$CO_2$Me |
| 8'-Pr | 8'-$CO_2$Me |
| 6'-Bu | 6'-$CH_2CO_2$H |
| 7'-Bu | 7'-$CH_2CO_2$H |
| 8'-Bu | 8'-$CH_2CO_2$H |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2$NHMe |
| 7'-OEt | 7'-$SO_2$NHMe |
| 8'-OEt | 8'-$SO_2$NHMe |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

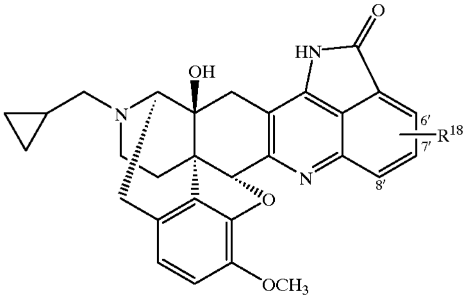

| R16 | R18 |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2$Me |
| 7'-Br | 7'-$SO_2$Me |
| 8'-Br | 8'-$SO_2$Me |
| 6'-I | 6'-$CO_2$H |
| 7'-I | 7'-$CO_2$H |
| 8'-I | 8'-$CO_2$H |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2$OH |
| 7'-OH | 7'-$CH_2$OH |
| 8'-OH | 8'-$CH_2$OH |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2$Me |
| 7'-Pr | 7'-$CO_2$Me |
| 8'-Pr | 8'-$CO_2$Me |
| 6'-Bu | 6'-$CH_2CO_2$H |
| 7'-Bu | 7'-$CH_2CO_2$H |
| 8'-Bu | 8'-$CH_2CO_2$H |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2$NHMe |
| 7'-OEt | 7'-$SO_2$NHMe |
| 8'-OEt | 8'-$SO_2$NHMe |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

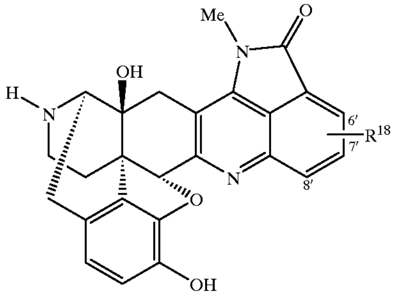

| $R^{16}$ | $R^{18}$ |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2$Me |
| 7'-Br | 7'-$SO_2$Me |
| 8'-Br | 8'-$SO_2$Me |
| 6'-I | 6'-$CO_2$H |
| 7'-I | 7'-$CO_2$H |
| 8'-I | 8'-$CO_2$H |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2$CH |
| 7'-OH | 7'-$CH_2$OH |
| 8'-OH | 8'-$CH_2$OH |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2$Me |
| 7'-Pr | 7'-$CO_2$Me |
| 8'-Pr | 8'-$CO_2$Me |
| 6'-Bu | 6'-$CH_2CO_2$H |
| 7'-Bu | 7'-$CH_2CO_2$H |
| 8'-Bu | 8'-$CH_2CO_2$H |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2$NHMe |
| 7'-OEt | 7'-$SO_2$NHMe |
| 8'-OEt | 8'-$SO_2$NHMe |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

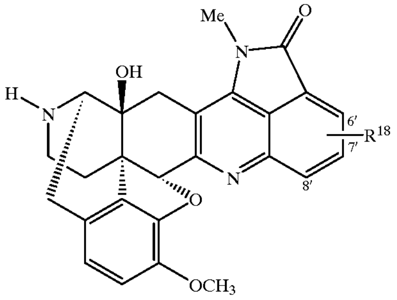

| $R^{16}$ | $R^{18}$ |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2$Me |
| 7'-Br | 7'-$SO_2$Me |
| 8'-Br | 8'-$SO_2$Me |
| 6'-I | 6'-$CO_2$H |
| 7'-I | 7'-$CO_2$H |
| 8'-I | 8'-$CO_2$H |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2$OH |
| 7'-OH | 7'-$CH_2$OH |
| 8'-OH | 8'-$CH_2$OH |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2$Me |
| 7'-Pr | 7'-$CO_2$Me |
| 8'-Pr | 8'-$CO_2$Me |
| 6'-Bu | 6'-$CH_2CO_2$H |
| 7'-Bu | 7'-$CH_2CO_2$H |
| 8'-Bu | 8'-$CH_2CO_2$H |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2$NHMe |
| 7'-OEt | 7'-$SO_2$NHMe |
| 8'-OEt | 8'-$SO_2$NHMe |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

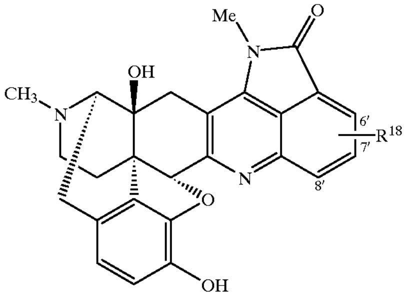

| $R^{16}$ | $R^{18}$ |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2$Me |
| 7'-Br | 7'-$SO_2$Me |
| 8'-Br | 8'-$SO_2$Me |
| 6'-I | 6'-$CO_2$H |
| 7'-I | 7'-$CO_2$H |
| 8'-I | 8'-$CO_2$H |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2$OH |
| 7'-OH | 7'-$CH_2$OH |
| 8'-OH | 8'-$CH_2$OH |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2$Me |
| 7'-Pr | 7'-$CO_2$Me |
| 8'-Pr | 8'-$CO_2$Me |
| 6'-Bu | 6'-$CH_2CO_2H$ |
| 7'-Bu | 7'-$CH_2CO_2H$ |
| 8'-Bu | 8'-$CH_2CO_2H$ |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2$NHMe |
| 7'-OEt | 7'-$SO_2$NHMe |
| 8'-OEt | 8'-$SO_2$NHMe |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

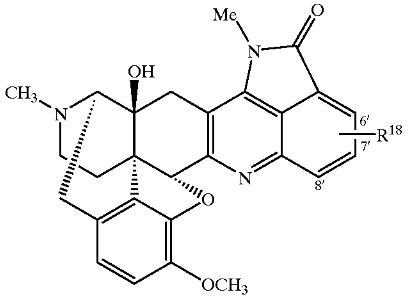

| $R^{16}$ | $R^{18}$ |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2$Me |
| 7'-Br | 7'-$SO_2$Me |
| 8'-Br | 8'-$SO_2$Me |
| 6'-I | 6'-$CO_2$H |
| 7'-I | 7'-$CO_2$H |
| 8'-I | 8'-$CO_2$H |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2$OH |
| 7'-OH | 7'-$CH_2$OH |
| 8'-OH | 8'-$CH_2$OH |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2$Me |
| 7'-Pr | 7'-$CO_2$Me |
| 8'-Pr | 8'-$CO_2$Me |
| 6'-Bu | 6'-$CH_2CO_2H$ |
| 7'-Bu | 7'-$CH_2CO_2H$ |
| 8'-Bu | 8'-$CH_2CO_2H$ |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2$NHMe |
| 7'-OEt | 7'-$SO_2$NHMe |
| 8'-OEt | 8'-$SO_2$NHMe |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

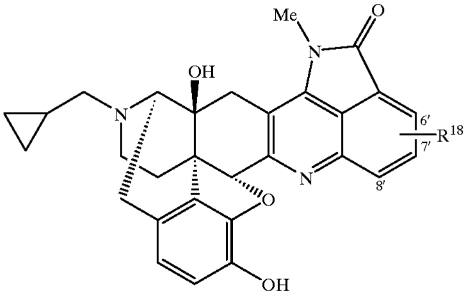

| $R^{16}$ | $R^{18}$ |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2$Me |
| 7'-Br | 7'-$SO_2$Me |
| 8'-Br | 8'-$SO_2$Me |
| 6'-I | 6'-$CO_2$H |
| 7'-I | 7'-$CO_2$H |
| 8'-I | 8'-$CO_2$H |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2$OH |
| 7'-OH | 7'-$CH_2$OH |
| 8'-OH | 8'-$CH_2$OH |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2$Me |
| 7'-Pr | 7'-$CO_2$Me |
| 8'-Pr | 8'-$CO_2$Me |
| 6'-Bu | 6'-$CH_2CO_2$H |
| 7'-Bu | 7'-$CH_2CO_2$H |
| 8'-Bu | 8'-$CH_2CO_2$H |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2$NHMe |
| 7'-OEt | 7'-$SO_2$NHMe |
| 8'-OEt | 8'-$SO_2$NHMe |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |
| 7'-CN | 7'-NHCHO |
| 8'-CN | 8'-NHCHO |

-continued

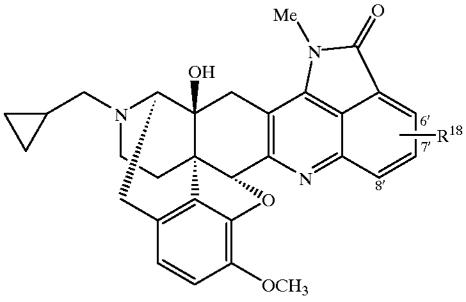

| $R^{16}$ | $R^{18}$ |
|---|---|
| 6'-F | 6'-Ph |
| 7'-F | 7'-Ph |
| 8'-F | 8'-Ph |
| 6'-Cl | 6'-SMe |
| 7'-Cl | 7'-SMe |
| 8'-Cl | 8'-SMe |
| 6'-Br | 6'-$SO_2$Me |
| 7'-Br | 7'-$SO_2$Me |
| 8'-Br | 8'-$SO_2$Me |
| 6'-I | 6'-$CO_2$H |
| 7'-I | 7'-$CO_2$H |
| 8'-I | 8'-$CO_2$H |
| 6'-$NO_2$ | 6'-$NH_2$ |
| 7'-$NO_2$ | 7'-$NH_2$ |
| 8'-$NO_2$ | 8'-$NH_2$ |
| 6'-OH | 6'-$CH_2$OH |
| 7'-OH | 7'-$CH_2$OH |
| 8'-OH | 8'-$CH_2$OH |
| 6'-Me | 6'-$CONH_2$ |
| 7'-Me | 7'-$CONH_2$ |
| 8'-Me | 8'-$CONH_2$ |
| 6'-Et | 6'-NHMe |
| 7'-Et | 7'-NHMe |
| 8'-Et | 8'-NHMe |
| 6'-Pr | 6'-$CO_2$Me |
| 7'-Pr | 7'-$CO_2$Me |
| 8'-Pr | 8'-$CO_2$Me |
| 6'-Bu | 6'-$CH_2CO_2$H |
| 7'-Bu | 7'-$CH_2CO_2$H |
| 8'-Bu | 8'-$CH_2CO_2$H |
| 6'-OMe | 6'-$SO_2NH_2$ |
| 7'-OMe | 7'-$SO_2NH_2$ |
| 8'-OMe | 8'-$SO_2NH_2$ |
| 6'-OEt | 6'-$SO_2$NHMe |
| 7'-OEt | 7'-$SO_2$NHMe |
| 8'-OEt | 8'-$SO_2$NHMe |
| 6'-NCS | 6'-CONHMe |
| 7'-NCS | 7'-CONHMe |
| 8'-NCS | 8'-CONHMe |
| 6'-$CF_3$ | 6'-$NMe_2$ |
| 7'-$CF_3$ | 7'-$NMe_2$ |
| 8'-$CF_3$ | 8'-$NMe_2$ |
| 6'-$OCF_3$ | 6'-$CH_2NH_2$ |
| 7'-$OCF_3$ | 7'-$CH_2NH_2$ |
| 8'-$OCF_3$ | 8'-$CH_2NH_2$ |
| 6'-CN | 6'-NHCHO |

-continued

| | |
|---|---|
| 7'-CN | 7'-NHCHO |
| 8'-CN | 8'-NHCHO |

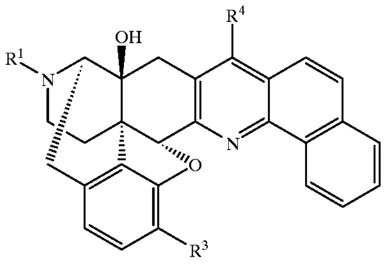

| $R^1$ | $R^3$ | $R^4$ |
|---|---|---|
| H | OH | H |
| Me | OH | H |
| cyclopropylmethyl | OH | H |
| H | $OCH_3$ | H |
| Me | $OCH_3$ | H |
| cyclopropylmethyl | $OCH_3$ | H |
| H | OH | Me |
| Me | OH | Me |
| cyclopropylmethyl | OH | Me |
| H | $OCH_3$ | Me |
| Me | $OCH_3$ | Me |
| cyclopropylmethyl | $OCH_3$ | Me |
| H | OH | $NH_2$ |
| Me | OH | $NH_2$ |
| cyclopropylmethyl | OH | $NH_2$ |
| H | $OCH_3$ | $NH_2$ |
| Me | $OCH_3$ | $NH_2$ |
| cyclopropylmethyl | $OCH_3$ | $NH_2$ |
| H | OH | NHMe |
| Me | OH | NHMe |
| cyclopropylmethyl | OH | NHMe |
| H | $OCH_3$ | NHMe |
| Me | $OCH_3$ | NHMe |
| cyclopropylmethyl | $OCH_3$ | NHMe |
| H | OH | NHCOMe |
| Me | OH | NHCOMe |
| cyclopropylmethyl | $OCH_3$ | NHCOMe |
| H | $OCH_3$ | NHCOMe |
| Me | $OCH_3$ | NHCOMe |
| cyclopropylmethyl | $OCH_3$ | NHCOMe |
| H | OH | OH |
| Me | OH | OH |
| cyclopropylmethyl | OH | OH |
| H | $OCH_3$ | OH |
| Me | $OCH_3$ | OH |
| cyclopropylmethyl | $OCH_3$ | OH |
| H | OH | $CO_2H$ |
| Me | OH | $CO_2H$ |
| cyclopropylmethyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| H | OH | $CO_2Me$ |
| Me | OH | $CO_2Me$ |
| cyclopropylmethyl | OH | $CO_2Me$ |
| H | $OCH_3$ | $CO_2Me$ |

-continued

| | | |
|---|---|---|
| Me | $OCH_3$ | $CO_2Me$ |
| cyclopropylmethyl | $OCH_3$ | $CO_2Me$ |

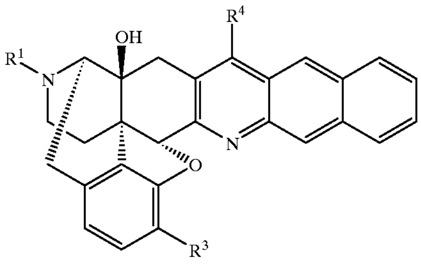

| $R^1$ | $R^3$ | $R^4$ |
|---|---|---|
| H | OH | H |
| Me | OH | H |
| cyclopropylmethyl | OH | H |
| H | $OCH_3$ | H |
| Me | $OCH_3$ | H |
| cyclopropylmethyl | $OCH_3$ | H |
| H | OH | Me |
| Me | OH | Me |
| cyclopropylmethyl | OH | Me |
| H | $OCH_3$ | Me |
| Me | $OCH_3$ | Me |
| cyclopropylmethyl | $OCH_3$ | Me |
| H | OH | $NH_2$ |
| Me | OH | $NH_2$ |
| cyclopropylmethyl | OH | $NH_2$ |
| H | $OCH_3$ | $NH_2$ |
| Me | $OCH_3$ | $NH_2$ |
| cyclopropylmethyl | $OCH_3$ | $NH_2$ |
| H | OH | NHMe |
| Me | OH | NHMe |
| cyclopropylmethyl | OH | NHMe |
| H | $OCH_3$ | NHMe |
| Me | $OCH_3$ | NHMe |
| cyclopropylmethyl | $OCH_3$ | NHMe |
| H | OH | NHCOMe |
| Me | OH | NHCOMe |
| cyclopropylmethyl | OH | NHCOMe |
| H | $OCH_3$ | NHCOMe |
| Me | $OCH_3$ | NHCOMe |
| cyclopropylmethyl | $OCH_3$ | NHCOMe |
| H | OH | OH |
| Me | OH | OH |
| cyclopropylmethyl | OH | OH |
| H | $OCH_3$ | OH |
| Me | $OCH_3$ | OH |
| cyclopropylmethyl | $OCH_3$ | OH |
| H | OH | $CO_2H$ |
| Me | OH | $CO_2H$ |
| cyclopropylmethyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| H | OH | $CO_2Me$ |
| Me | OH | $CO_2Me$ |
| cyclopropylmethyl | OH | $CO_2Me$ |
| H | $OCH_3$ | $CO_2Me$ |

-continued

| | | |
|---|---|---|
| Me | $OCH_3$ | $CO_2Me$ |
| cyclopropylmethyl | $OCH_3$ | $CO_2Me$ |

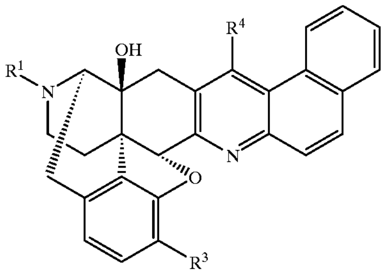

| $R^1$ | $R^3$ | $R^4$ |
|---|---|---|
| H | OH | H |
| Me | OH | H |
| cyclopropylmethyl | OH | H |
| H | $OCH_3$ | H |
| Me | $OCH_3$ | H |
| cyclopropylmethyl | $OCH_3$ | H |
| H | OH | Me |
| Me | OH | Me |
| cyclopropylmethyl | OH | Me |
| H | $OCH_3$ | Me |
| Me | $OCH_3$ | Me |
| cyclopropylmethyl | $OCH_3$ | Me |
| H | OH | $NH_2$ |
| Me | OH | $NH_2$ |
| cyclopropylmethyl | OH | $NH_2$ |
| H | $OCH_3$ | $NH_2$ |
| Me | $OCH_3$ | $NH_2$ |
| cyclopropylmethyl | $OCH_3$ | $NH_2$ |
| H | OH | NHMe |
| Me | OH | NHMe |
| cyclopropylmethyl | OH | NHMe |
| H | $OCH_3$ | NHMe |
| Me | $OCH_3$ | NHMe |
| cyclopropylmethyl | $OCH_3$ | NHMe |
| H | OH | NHCOMe |
| Me | OH | NHCOMe |
| cyclopropylmethyl | OH | NHCOMe |
| H | $OCH_3$ | NHCOMe |
| Me | $OCH_3$ | NHCOMe |
| cyclopropylmethyl | $OCH_3$ | NHCOMe |
| H | OH | OH |
| Me | OH | OH |
| cyclopropylmethyl | OH | OH |
| H | $OCH_3$ | OH |
| Me | $OCH_3$ | OH |
| cyclopropylmethyl | $OCH_3$ | OH |
| H | OH | $CO_2H$ |
| Me | OH | $CO_2H$ |
| cyclopropylmethyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| H | OH | $CO_2Me$ |
| Me | OH | $CO_2Me$ |
| cyclopropylmethyl | OH | $CO_2Me$ |
| H | $OCH_3$ | $CO_2Me$ |

-continued

| | | |
|---|---|---|
| Me | $OCH_3$ | $CO_2Me$ |
| cyclopropylmethyl | $OCH_3$ | $CO_2Me$ |

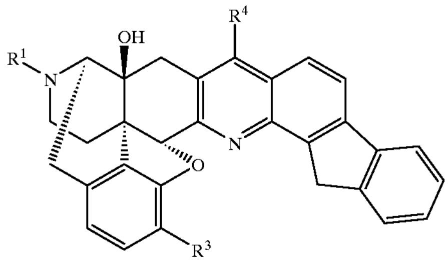

| $R^1$ | $R^3$ | $R^4$ |
|---|---|---|
| H | OH | H |
| Me | OH | H |
| cyclopropylmethyl | OH | H |
| H | $OCH_3$ | H |
| Me | $OCH_3$ | H |
| cyclopropylmethyl | $OCH_3$ | H |
| H | OH | Me |
| Me | OH | Me |
| cyclopropylmethyl | OH | Me |
| H | $OCH_3$ | Me |
| Me | $OCH_3$ | Me |
| cyclopropylmethyl | $OCH_3$ | Me |
| H | OH | $NH_2$ |
| Me | OH | $NH_2$ |
| cyclopropylmethyl | OH | $NH_2$ |
| H | $OCH_3$ | $NH_2$ |
| Me | $OCH_3$ | $NH_2$ |
| cyclopropylmethyl | $OCH_3$ | $NH_2$ |
| H | OH | NHMe |
| Me | OH | NHMe |
| cyclopropylmethyl | OH | NHMe |
| H | $OCH_3$ | NHMe |
| Me | $OCH_3$ | NHMe |
| cyclopropylmethyl | $OCH_3$ | NHMe |
| H | OH | NHCOMe |
| Me | OH | NHCOMe |
| cyclopropylmethyl | OH | NHCOMe |
| H | $OCH_3$ | NHCOMe |
| Me | $OCH_3$ | NHCOMe |
| cyclopropylmethyl | $OCH_3$ | NHCOMe |
| H | OH | OH |
| Me | OH | OH |
| cyclopropylmethyl | OH | OH |
| H | $OCH_3$ | OH |
| Me | $OCH_3$ | OH |
| cyclopropylmethyl | $OCH_3$ | OH |
| H | OH | $CO_2H$ |
| Me | OH | $CO_2H$ |
| cyclopropylmethyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| H | OH | $CO_2Me$ |
| Me | OH | $CO_2Me$ |
| cyclopropylmethyl | OH | $CO_2Me$ |
| H | $OCH_3$ | $CO_2Me$ |

-continued

| | | |
|---|---|---|
| Me | $OCH_3$ | $CO_2Me$ |
| cyclopropylmethyl | $OCH_3$ | $CO_2Me$ |

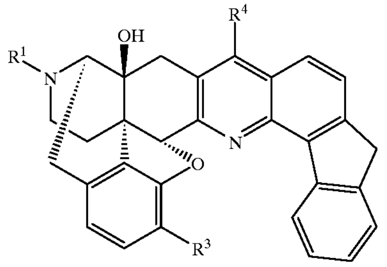

| $R^1$ | $R^3$ | $R^4$ |
|---|---|---|
| H | OH | H |
| Me | OH | H |
| cyclopropylmethyl | OH | H |
| H | $OCH_3$ | H |
| Me | $OCH_3$ | H |
| cyclopropylmethyl | $OCH_3$ | H |
| H | OH | Me |
| Me | OH | Me |
| cyclopropylmethyl | OH | Me |
| H | $OCH_3$ | Me |
| Me | $OCH_3$ | Me |
| cyclopropylmethyl | $OCH_3$ | Me |
| H | OH | $NH_2$ |
| Me | OH | $NH_2$ |
| cyclopropylmethyl | OH | $NH_2$ |
| H | $OCH_3$ | $NH_2$ |
| Me | $OCH_3$ | $NH_2$ |
| cyclopropylmethyl | $OCH_3$ | $NH_2$ |
| H | OH | NHMe |
| Me | OH | NHMe |
| cyclopropylmethyl | OH | NHMe |
| H | $OCH_3$ | NHMe |
| Me | $OCH_3$ | NHMe |
| cyclopropylmethyl | $OCH_3$ | NHMe |
| H | OH | NHCOMe |
| Me | OH | NHCOMe |
| cyclopropylmethyl | OH | NHCOMe |
| H | $OCH_3$ | NHCOMe |
| Me | $OCH_3$ | NHCOMe |
| cyclopropylmethyl | $OCH_3$ | NHCOMe |
| H | OH | OH |
| Me | OH | OH |
| cyclopropylmethyl | OH | OH |
| H | $OCH_3$ | OH |
| Me | $OCH_3$ | OH |
| cyclopropylmethyl | $OCH_3$ | OH |
| H | OH | $CO_2H$ |
| Me | OH | $CO_2H$ |
| cyclopropylmethyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| H | OH | $CO_2Me$ |
| Me | OH | $CO_2Me$ |
| cyclopropylmethyl | OH | $CO_2Me$ |
| H | $OCH_3$ | $CO_2Me$ |

-continued

| | | |
|---|---|---|
| Me | $OCH_3$ | $CO_2Me$ |
| cyclopropylmethyl | $OCH_3$ | $CO_2Me$ |

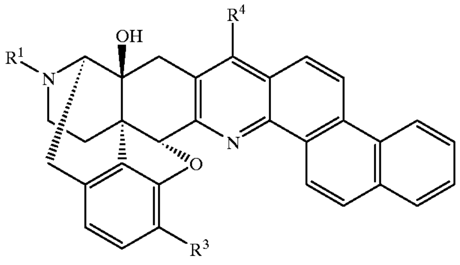

| $R^1$ | $R^3$ | $R^4$ |
|---|---|---|
| H | OH | H |
| Me | OH | H |
| cyclopropylmethyl | OH | H |
| H | $OCH_3$ | H |
| Me | $OCH_3$ | H |
| cyclopropylmethyl | $OCH_3$ | H |
| H | OH | Me |
| Me | OH | Me |
| cyclopropylmethyl | OH | Me |
| H | $OCH_3$ | Me |
| Me | $OCH_3$ | Me |
| cyclopropylmethyl | $OCH_3$ | Me |
| H | OH | $NH_2$ |
| Me | OH | $NH_2$ |
| cyclopropylmethyl | OH | $NH_2$ |
| H | $OCH_3$ | $NH_2$ |
| Me | $OCH_3$ | $NH_2$ |
| cyclopropylmethyl | $OCH_3$ | $NH_2$ |
| H | OH | NHMe |
| Me | OH | NHMe |
| cyclopropylmethyl | OH | NHMe |
| H | $OCH_3$ | NHMe |
| Me | $OCH_3$ | NHMe |
| cyclopropylmethyl | $OCH_3$ | NHMe |
| H | OH | NHCOMe |
| Me | OH | NHCOMe |
| cyclopropylmethyl | OH | NHCOMe |
| H | $OCH_3$ | NHCOMe |
| Me | $OCH_3$ | NHCOMe |
| cyclopropylmethyl | $OCH_3$ | NHCOMe |
| H | OH | OH |
| Me | OH | OH |
| cyclopropylmethyl | OH | OH |
| H | $OCH_3$ | OH |
| Me | $OCH_3$ | OH |
| cyclopropylmethyl | $OCH_3$ | OH |
| H | OH | $CO_2H$ |
| Me | OH | $CO_2H$ |
| cyclopropylmethyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| H | OH | $CO_2Me$ |
| Me | OH | $CO_2Me$ |
| cyclopropylmethyl | OH | $CO_2Me$ |
| H | $OCH_3$ | $CO_2Me$ |

-continued

| | | |
|---|---|---|
| Me | $OCH_3$ | $CO_2Me$ |
| cyclopropylmethyl | $OCH_3$ | $CO_2Me$ |

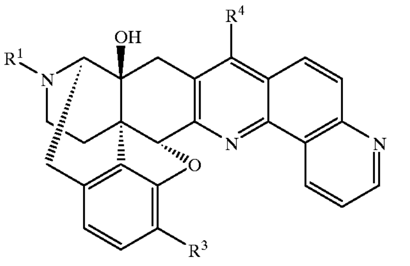

| $R^1$ | $R^3$ | $R^4$ |
|---|---|---|
| H | OH | H |
| Me | OH | H |
| cyclopropylmethyl | OH | H |
| H | $OCH_3$ | H |
| Me | $OCH_3$ | H |
| cyclopropylmethyl | $OCH_3$ | H |
| H | OH | Me |
| Me | OH | Me |
| cyclopropylmethyl | OH | Me |
| H | $OCH_3$ | Me |
| Me | $OCH_3$ | Me |
| cyclopropylmethyl | $OCH_3$ | Me |
| H | OH | $NH_2$ |
| Me | OH | $NH_2$ |
| cyclopropylmethyl | OH | $NH_2$ |
| H | $OCH_3$ | $NH_2$ |
| Me | $OCH_3$ | $NH_2$ |
| cyclopropylmethyl | $OCH_3$ | $NH_2$ |
| H | OH | NHMe |
| Me | OH | NHMe |
| cyclopropylmethyl | OH | NHMe |
| H | $OCH_3$ | NHMe |
| Me | $OCH_3$ | NHMe |
| cyclopropylmethyl | $OCH_3$ | NHMe |
| H | OH | NHCOMe |
| Me | OH | NHCOMe |
| cyclopropylmethyl | OH | NHCOMe |
| H | $OCH_3$ | NHCOMe |
| Me | $OCH_3$ | NHCOMe |
| cyclopropylmethyl | $OCH_3$ | NHCOMe |
| H | OH | OH |
| Me | OH | OH |
| cyclopropylmethyl | OH | OH |
| H | $OCH_3$ | OH |
| Me | $OCH_3$ | OH |
| cyclopropylmethyl | $OCH_3$ | OH |
| H | OH | $CO_2H$ |
| Me | OH | $CO_2H$ |
| cyclopropylmethyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| H | OH | $CO_2Me$ |
| Me | OH | $CO_2Me$ |
| cyclopropylmethyl | OH | $CO_2Me$ |
| H | $OCH_3$ | $CO_2Me$ |

-continued

| | | |
|---|---|---|
| Me | $OCH_3$ | $CO_2Me$ |
| cyclopropylmethyl | $OCH_3$ | $CO_2Me$ |

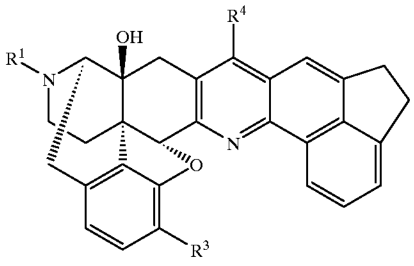

| $R^1$ | $R^3$ | $R^4$ |
|---|---|---|
| H | OH | H |
| Me | OH | H |
| cyclopropylmethyl | OH | H |
| H | $OCH_3$ | H |
| Me | $OCH_3$ | H |
| cyclopropylmethyl | $OCH_3$ | H |
| H | OH | Me |
| Me | OH | Me |
| cyclopropylmethyl | OH | Me |
| H | $OCH_3$ | Me |
| Me | $OCH_3$ | Me |
| cyclopropylmethyl | $OCH_3$ | Me |
| H | OH | $NH_2$ |
| Me | OH | $NH_2$ |
| cyclopropylmethyl | OH | $NH_2$ |
| H | $OCH_3$ | $NH_2$ |
| Me | $OCH_3$ | $NH_2$ |
| cyclopropylmethyl | $OCH_3$ | $NH_2$ |
| H | OH | NHMe |
| Me | OH | NHMe |
| cyclopropylmethyl | OH | NHMe |
| H | $OCH_3$ | NHMe |
| Me | $OCH_3$ | NHMe |
| cyclopropylmethyl | $OCH_3$ | NHMe |
| H | OH | NHCOMe |
| Me | OH | NHCOMe |
| cyclopropylmethyl | OH | NHCOMe |
| H | $OCH_3$ | NHCOMe |
| Me | $OCH_3$ | NHCOMe |
| cyclopropylmethyl | $OCH_3$ | NHCOMe |
| H | OH | OH |
| Me | OH | OH |
| cyclopropylmethyl | OH | OH |
| H | $OCH_3$ | OH |
| Me | $OCH_3$ | OH |
| cyclopropylmethyl | $OCH_3$ | OH |
| H | OH | $CO_2H$ |
| Me | OH | $CO_2H$ |
| cyclopropylmethyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| H | OH | $CO_2Me$ |
| Me | OH | $CO_2Me$ |
| cyclopropylmethyl | OH | $CO_2Me$ |
| H | $OCH_3$ | $CO_2Me$ |

-continued

| | | |
|---|---|---|
| Me | $OCH_3$ | $CO_2Me$ |
| cyclopropylmethyl | $OCH_3$ | $CO_2Me$ |

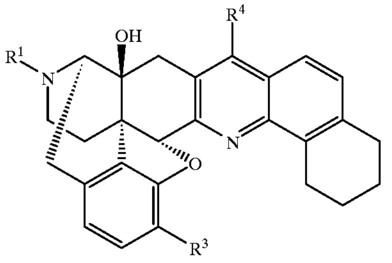

| $R^1$ | $R^3$ | $R^4$ |
|---|---|---|
| H | OH | H |
| Me | OH | H |
| cyclopropylmethyl | OH | H |
| H | $OCH_3$ | H |
| Me | $OCH_3$ | H |
| cyclopropylmethyl | $OCH_3$ | H |
| H | OH | Me |
| Me | OH | Me |
| cyclopropylmethyl | OH | Me |
| H | $OCH_3$ | Me |
| Me | $OCH_3$ | Me |
| cyclopropylmethyl | $OCH_3$ | Me |
| H | OH | $NH_2$ |
| Me | OH | $NH_2$ |
| cyclopropylmethyl | OH | $NH_2$ |
| H | $OCH_3$ | $NH_2$ |
| Me | $OCH_3$ | $NH_2$ |
| cyclopropylmethyl | $OCH_3$ | $NH_2$ |
| H | OH | NHMe |
| Me | OH | NHMe |
| cyclopropylmethyl | OH | NHMe |
| H | $OCH_3$ | NHMe |
| Me | $OCH_3$ | NHMe |
| cyclopropylmethyl | $OCH_3$ | NHMe |
| H | OH | NHCOMe |
| Me | OH | NHCOMe |
| cyclopropylmethyl | OH | NHCOMe |
| H | $OCH_3$ | NHCOMe |
| Me | $OCH_3$ | NHCOMe |
| cyclopropylmethyl | $OCH_3$ | NHCOMe |
| H | OH | OH |
| Me | OH | OH |
| cyclopropylmethyl | OH | OH |
| H | $OCH_3$ | OH |
| Me | $OCH_3$ | OH |
| cyclopropylmethyl | $OCH_3$ | OH |
| H | OH | $CO_2H$ |
| Me | OH | $CO_2H$ |
| cyclopropylmethyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| H | OH | $CO_2Me$ |
| Me | OH | $CO_2Me$ |
| cyclopropylmethyl | OH | $CO_2Me$ |
| H | $OCH_3$ | $CO_2Me$ |
| Me | $OCH_3$ | $CO_2Me$ |
| cyclopropylmethyl | $OCH_3$ | $CO_2Me$ |

-continued

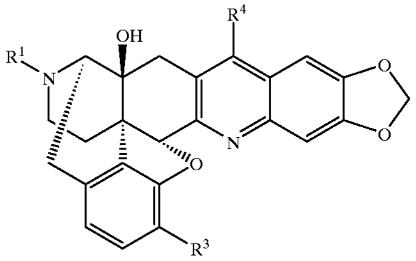

| $R^1$ | $R^3$ | $R^4$ |
|---|---|---|
| H | OH | H |
| Me | OH | H |
| cyclopropylmethyl | OH | H |
| H | $OCH_3$ | H |
| Me | $OCH_3$ | H |
| cyclopropylmethyl | $OCH_3$ | H |
| H | OH | Me |
| Me | OH | Me |
| cyclopropylmethyl | OH | Me |
| H | $OCH_3$ | Me |
| Me | $OCH_3$ | Me |
| cyclopropylmethyl | $OCH_3$ | Me |
| H | OH | $NH_2$ |
| Me | OH | $NH_2$ |
| cyclopropylmethyl | OH | $NH_2$ |
| H | $OCH_3$ | $NH_2$ |
| Me | $OCH_3$ | $NH_2$ |
| cyclopropylmethyl | $OCH_3$ | $NH_2$ |
| H | OH | NHMe |
| Me | OH | NHMe |
| cyclopropylmethyl | OH | NHMe |
| H | $OCH_3$ | NHMe |
| Me | $OCH_3$ | NHMe |
| cyclopropylmethyl | $OCH_3$ | NHMe |
| H | OH | NHCOMe |
| Me | OH | NHCOMe |
| cyclopropylmethyl | OH | NHCOMe |
| H | $OCH_3$ | NHCOMe |
| Me | $OCH_3$ | NHCOMe |
| cyclopropylmethyl | $OCH_3$ | NHCOMe |
| H | OH | OH |
| Me | OH | OH |
| cyclopropylmethyl | OH | OH |
| H | $OCH_3$ | OH |
| Me | $OCH_3$ | OH |
| cyclopropylmethyl | $OCH_3$ | OH |
| H | OH | $CO_2H$ |
| Me | OH | $CO_2H$ |
| cyclopropylmethyl | OH | $CO_2H$ |
| H | $OCH_3$ | $CO_2H$ |
| Me | $OCH_3$ | $CO_2H$ |
| cyclopropylmethyl | $OCH_3$ | $CO_2H$ |
| H | OH | $CO_2Me$ |
| Me | OH | $CO_2Me$ |
| cyclopropylmethyl | OH | $CO_2Me$ |
| H | $OCH_3$ | $CO_2Me$ |
| Me | $OCH_3$ | $CO_2Me$ |
| cyclopropylmethyl | $OCH_3$ | $CO_2Me$ |

The compounds represented by formula (I) of the present invention ($R^1$, $R^2$, $R^3$, $R^4$, $R^5$ and m are defined as the same as the above) can be generally produced by quinoline synthesis reaction using ketone compounds represented by formula (VII) ($R^1$, $R^2$ and $R^3$ are defined as the same as the above) as raw materials, and aminocarbonyl derivatives presented by formula (VIII) ($R^4$, $R^5$ and m are defined as the same as the above) or aminobenzonitrile derivatives represented by formula (IX) ($R^5$ and m are defined as the same as the above), as shown in Scheme 1. Of the compounds represented by formula (I), compounds wherein $R^4$ is $NR^{10}R^{11}$, and $R^{10}$ and $R^{11}$ are each hydrogen can simply be produced by using aminobenzonitrile derivatives represented by formula (IX).

halide $R^1$—$X^1$ (wherein $X^1$ represents chloro, bromo, iodo, or p-toluenesulfonyloxy) in the presence of an appropriate base, or (2) acylation reaction using an appropriate acid chloride $R^{1a}$—CO—Cl (wherein $R^{1a}$ represents a group in which one terminal carbonyl is removed from $R^1$) according to a general method, as shown by the formula on the upper right of Scheme 2. The compounds of formula (I) can be produced by quinoline synthesis reaction using the thus-obtained ketone compounds represented by formula (VII) as raw materials.

Scheme 1

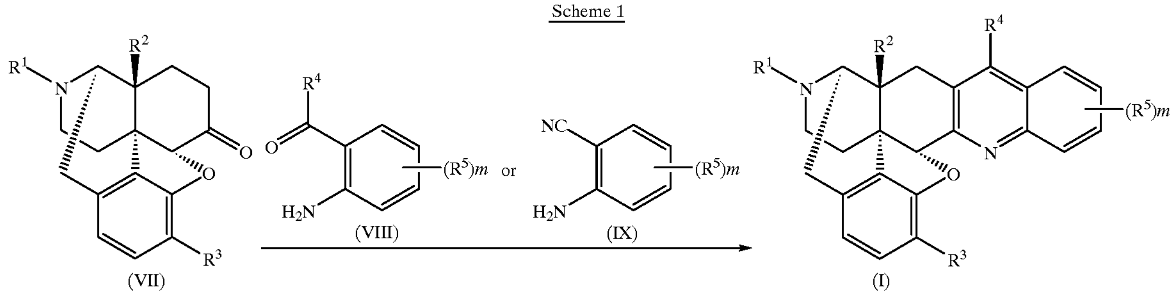

(VII) (VIII) or (IX) (I)

In the present invention, quinoline synthesis reaction can generally be effected in the presence of an appropriate acid according to demand in an appropriate solvent. Examples of the solvent include alcoholic solvents such as methanol, ethanol, and the like; organic carboxylic acid solvents such as formic acid, acetic acid, propionic acid, and the like; hydrocarbon solvents such as benzene, toluene, and the like; ether solvents such as diethyl ether, THF, and the like; halogenated hydrocarbon solvents such as chloroform, dichloromethane, dichloroethane, and the like; ester solvents such as ethyl acetate, and the like; aprotic polar solvents such as DMF, DMSO, and the like; water; and solvent mixtures thereof. Particularly, alcoholic solvents, organic acid solvents, and solvent mixtures of hydrocarbon solvents-aprotic polar solvents are preferably used. As reaction conditions, normal hearing conditions, azeotropic conditions or heating concentration conditions are preferably used. Examples of acids include any general acids such as inorganic acids such as hydrochloric acid, sulfuric acid, nitric acid, phosphoric acid, and the like; organic carboxylic acids such as formic acid, acetic acid, propionic acid, and the like; organic sulfonic acids such as methanesulfonic acid, p-toluenesulfonic acid, camphorsulfonic acid, and the like; Lewis acids such as zinc chloride, phosphorus trichloride, scandium triflate, and the like. Of these acids, hydrochloric acid, sulfuric acid, phosphoric acid, formic acid, acetic acid, propionic acid, methanesulfonic acid, p-toluenesulfonic acid, and scandium triflate are preferably used.

Of ketone compounds represented by formula (VII) and used as raw materials for quinoline synthesis reaction, compounds in which both of $R^2$ and $R^3$ are hydroxy, and $R^1$ is hydrogen, methyl, allyl and cyclopropylmethyl are generally known as noroxymorphone, oxymorphone, naloxone, and nartrexone, respectively, and a compound in which $R^2$ is hydroxy, $R^3$ is methoxy, and $R^1$ is hydrogen is generally known as noroxycodone. These compounds can be used without any change. Ketone compounds (VII) in which $R^1$ is a group other than the above can be prepared from noroxymorphone or noroxycodone in which $R^1$ is hydrogen by using the method disclosed in the document [J. Med. Chem., Vol. 35, 4329 (1992).] or the like. Specifically, by using ketone compounds ($R^2$ and $R^3$ are defined as the same as the above) represented by formula (VII') in which $R^1$ is hydrogen, ketone compounds represented by formula (VII) can be prepared by (1) alkylation reaction using an alkyl Of compounds (I) of the present invention, compounds in which $R^4$ is hydrogen, alkyl having 1 to 5 carbon atoms, aryl having 6 to 12 carbon atoms, $NR^{10}R^{11}$, $OR^{12}$, $COOR^{13}$, or $CONR^{14}R^{15}$ (wherein $R^{10}$, $R^{11}$ and $R^{12}$ independently represent alkyl having 1 to 5 carbon atoms, aralkyl having 7 to 13 carbon atoms, or alkanoyl having 1 to 5 carbon atoms; and $R^{13}$, $R^{14}$ and $R^{15}$ independently represent alkyl having 1 to 5 carbon atoms, aryl having 6 to 12 carbon atoms, or aralkyl having 7 to 13 carbon atoms) can also be produced by the method shown by the formula on the under left of Scheme 2. In other words, such compounds can be produced by general alkylation or acylation reaction of an amino group by using compounds (I') ($R^2$, $R^3$, $R^4$, $R^5$ and m are defined as the same as the above) produced by quinoline synthesis reaction using the ketone compounds (VII') ($R^2$ and $R^3$ are defined as the same as the above) as raw materials. As a method for alkylation or acylation reaction of the amino group, any one of the methods (1), (2), (3) and (4) below can be used. Namely, by using the compounds (I') of the present invention, the compounds (I) can be produced by (1) alkylation reaction using an alkyl halide $R^1$—$X^1$ (wherein $X^1$ is defined as the same as the above) in the presence of an appropriate base, (2) reducrive amination reaction using an appropriate aldehyde $R^{1b}$—CHO (wherein $R^{1b}$ represents a group obtained by removing a methylene terminal from $R^1$) and a reducing agent such as sodium cyanoborohydride, sodium triacetoxyborohydride, or the like, or hydrogenation reaction, (3) acylation reaction using an appropriate acid chloride $R^{1a}$—CO—Cl ($R^{1a}$ is defined as the same as the above) according to a general method, or (4) a method comprising acylation using an appropriate acid chloride $R^{1b}$—CO—Cl ($R^{1b}$ is defined as the same as the above) and then reduction of amide by using a reducing agent such as lithium aluminum hydride, borane, or the like.

Scheme 2

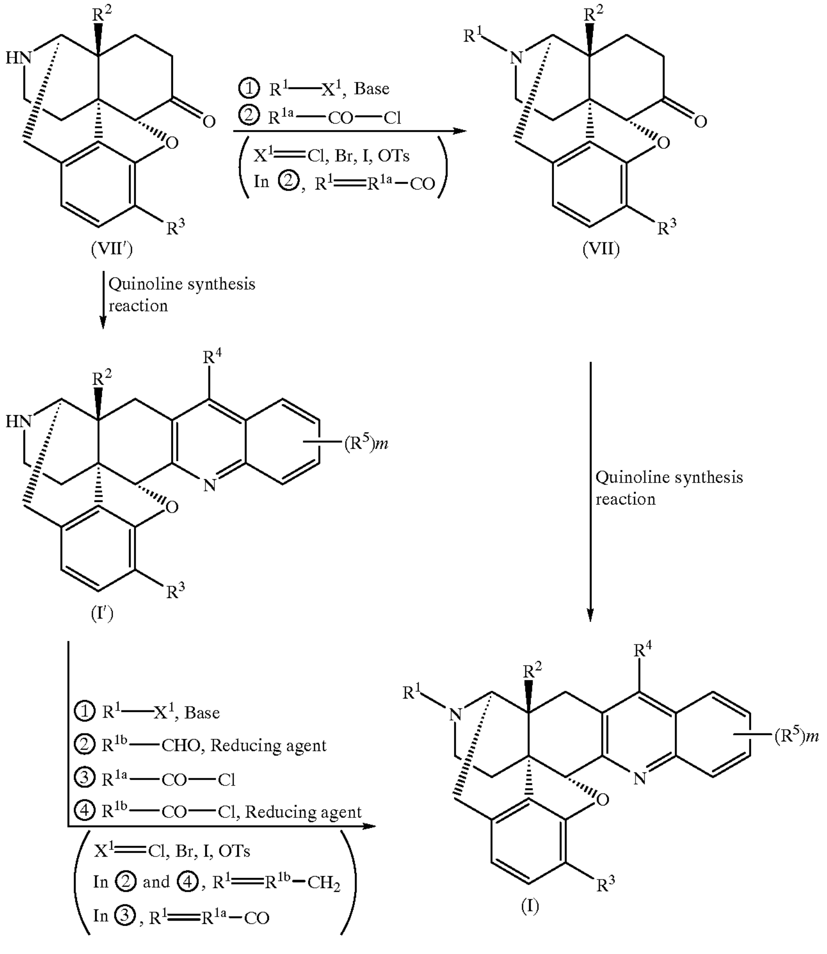

(VII') (VII) (I') (I)

When an organic carboxylic acid solvent is used as a reaction solvent for quinoline synthesis reaction using the ketone compounds (VII') (wherein $R^2$ and $R^3$ are defined as the same as the above) as raw materials, in some cases, compounds in which nitrogen at the 17-position is acylated are obtained. For example, the use of acetic acid sometimes produces compounds (I"), as shown in Scheme 2a. In this case, compounds (I") can be converted into compounds (I') in which $R^1$ is hydrogen, by hydrolysis reaction.

Scheme 2a

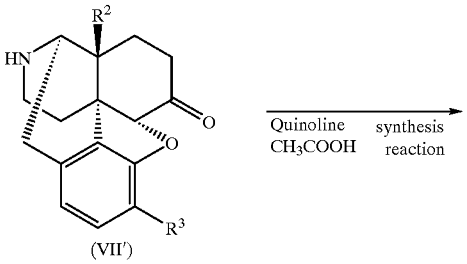

(VII')

-continued

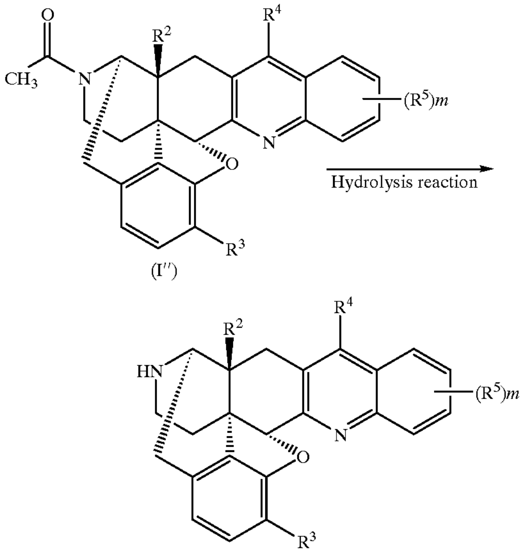

(I'') (I')

By applying the production method disclosed in U.S. Pat. No. 4,816,586, of the compounds represented by formula (I) of the present invention, compounds represented by formula (Ia) in which $R^4$ is hydrogen ($R^1$, $R^2$, $R^3$, $R^5$ and m are defined as the same as the above) can be produced by reacting the ketone compounds represented by formula (VII) and aminobenzaldehyde derivatives (VIIIa) ($R^5$ is defined as the same as the above) in which $R^4$ of aminocarbonyl derivatives of the formula (VIII) shown in Scheme 1 is hydrogen, as shown in Scheme 3.

Examples of the solvent used include alcoholic solvents such as methanol, ethanol, and the like; organic carboxylic acid solvents such as formic acid, acetic acid, propionic acid, and the like; hydrocarbon solvents such as benzene, toluene, and the like; and solvent mixtures thereof; particularly, ethanol, acetic acid, and toluene are preferable. Examples of the acid include inorganic acids such as hydrochloric acid, sulfuric acid, nitric acid, phosphoric acid, and the like; organic carboxylic acids such as formic acid, acetic acid, propionic acid, and the like; organic sulfonic acids such as methanesulfonic acid, p-toluenesulfonic acid, camphorsulfonic acid, and the like; Lewis acids such as zinc chloride, phosphorus trichloride, scandium triflate, and the like; particularly, hydrochloric acid and methanesulfonic acid are preferable.

Scheme 3

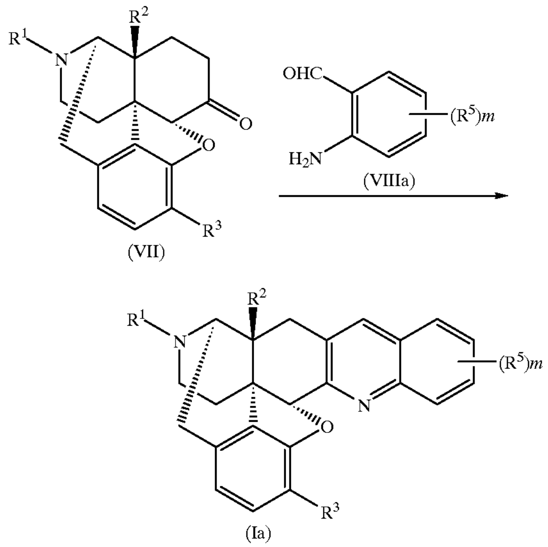

Compounds represented by the formula (Ia) can also be produced by reacting compounds represented by formula (X) ($R^1$, $R^2$ and $R^3$ are defined as the same as the above) and acid addition salts or free compounds of aniline derivatives represented by formula (XI) ($R^5$ is defined as the same as the above) in coexistence with an appropriate acid according to demand, as shown in Scheme 4.

Scheme 4

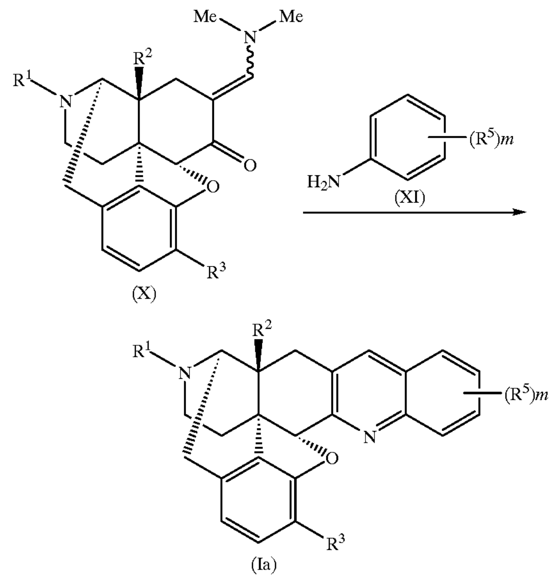

The compounds represented by formula (X) used as raw materials can be produced by reacting ketone compounds represented by formula (VII) and dimethylformamide dimethylacetal in a hydrocarbon solvent such as benzene, toluene, or the like, according to the method disclosed in the document [J. Med. Chem., 24, 1445 (1981)], as shown in Scheme 5. However, in the use of ketone compounds in which $R^3$ of ketone compounds represented by formula (VII) is hydroxy, in some cases, the hydroxy group is methylated to compounds represented by formula (X) in which $R^3$ is methoxy.

Scheme 5

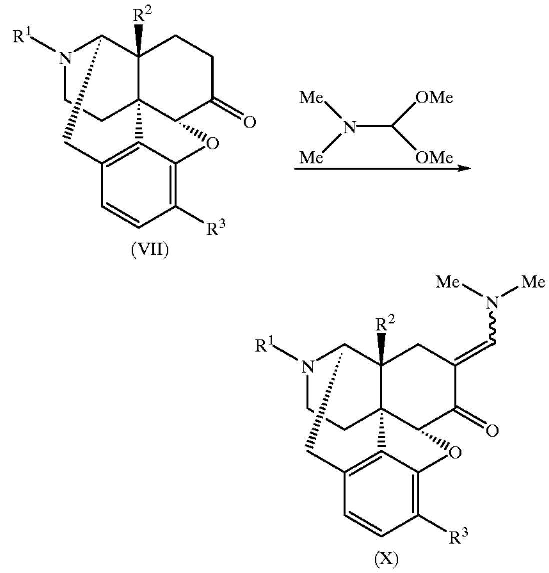

Examples of the solvent used in reaction of compounds represented by the formula (X) and compounds represented by the formula (XI) shown in Scheme 4 include alcoholic solvents such as methanol, ethanol, and the like; organic carboxylic acid solvents such as formic acid, acetic acid, propionic acid, lactic acid, and the like; hydrocarbon solvents such as benzene, toluene, and the like; and solvent mixtures thereof; particularly, acetic acid and lactic acid are preferable. Examples of the acid include inorganic acids such as hydrochloric acid, sulfuric acid, nitric acid, phosphoric acid, and the like; organic carboxylic acids such as formic acid, acetic acid, propionic acid, lactic acid, and the like; organic sulfonic acids such as methanesulfonic acid, p-toluenesulfonic acid, camphorsulfonic acid, and the like; Lewis acids such as zinc chloride, phosphorus trichloride, scandium triflate, and the like; generally, the use of acetic acid also used as the solvent produces sufficient effects. In some cases in which an intermediate is precipitated during reaction, the intermediate is filtered off, and dissolved in an appropriate solvent to effect reaction again. In purification of the compounds (Ia) of the present invention, the residual intermediate can easily be sometimes removed by hydrolysis reaction.

Of the compounds of formula (I) of the present invention, compounds represented by formula (Ib) ($R^1$, $R^2$, $R^3$, $R^5$ and m are defined as the same as the above) in which $R^4$ is $NR^{10}R^{11}$, and $R^{10}$ and $R^{11}$ are each hydrogen can be produced by reacting ketone compounds represented by formula (VII) and aminobenzonitrile derivatives represented by formula (IX) ($R^5$ and m are defined as the same as the above) in coexistence with an appropriate acid according to demand, as shown in Scheme 6.

Scheme 6

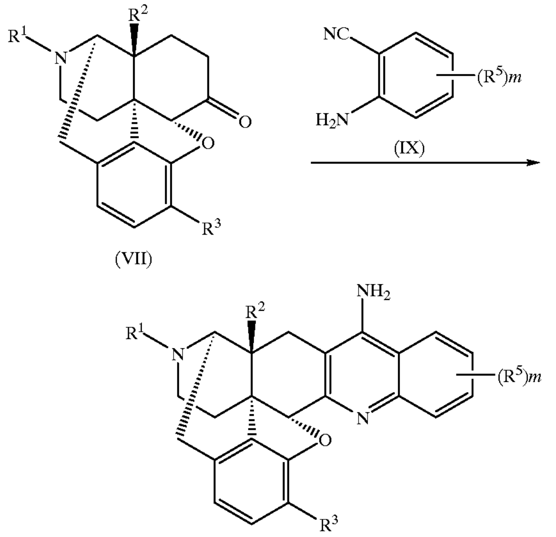

(VII) (IX) (Ib)

Examples of the solvent include alcoholic solvents such as methanol, ethanol, and the like; organic carboxylic acid solvents such as formic acid, acetic acid, propionic acid, and the like; hydrocarbon solvents such as benzene, toluene, and the like; water; and solvent mixtures thereof; particularly, hydrocarbon solvents such as benzene, toluene, and the like; organic carboxylic acid solvents such as acetic acid and propionic acid, and the like; water; and solvent mixtures thereof are preferable. Particularly, the use of toluene or acetic acid produces good results. Examples of the acid include inorganic acids such as hydrochloric acid, sulfuric acid, nitric acid, phosphoric acid, and the like; organic carboxylic acids such as formic acid, acetic acid, propionic acid, and the like; organic sulfonic acids such as methanesulfonic acid, p-toluenesulfonic acid, camphorsulfonic acid, and the like; Lewis acids such as zinc chloride, zinc trichloride, cuprous chloride, phosphorus trichloride, scandium triflate, and the like. Particularly, hydrochloric acid, sulfuric acid, acetic acid, propionic acid, methanesulfonic acid, zinc chloride, cuprous chloride, scandium triflate are preferable; the use of acetic acid, propionic acid or scandium triflate produces good results.

The aminobenzonitrile derivatives (IX) used in the reaction shown in Scheme 6 may be commercially available compounds or prepared from corresponding aniline derivatives (XI) ($R^5$ and m are defined as the same as the above) by using the method disclosed in the document [Synth. Comm., 20(1), 71 (1990)], as shown in Scheme 7. The aminobenzonitrile derivatives (IX) used can also be prepared from corresponding nitrobenzonitrile derivatives (XII) ($R^5$ and m are defined as the same as the above) by reduction of a nitro group using the method disclosed in the document [J. Med. Chem., 24, 742 (1981)], as shown in Scheme 8.

Scheme 7

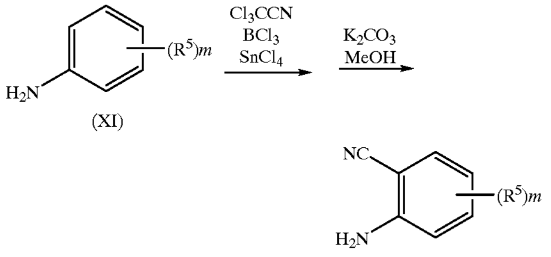

(XI) (IX)

Scheme 8

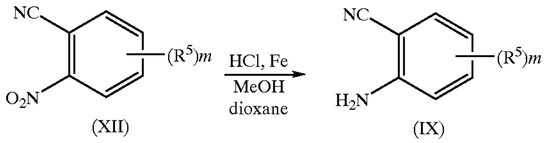

(XII) (IX)

Of the compounds of formula (I) of the present invention, compounds represented by formula (Id) ($R^1$, $R^2$, $R^3$, $R^5$ and m are defined as the same as the above) in which $R^4$ is $NR^{10}R^{11}$, $R^{10}$ is hydrogen, alkyl having 1 to 5 carbon atoms, aralkyl having 7 to 13 carbon atoms, or alkanoyl having 1 to 5 carbon atoms, and $R^{11}$ is independently alkyl having 1 to 5 carbon atoms, aralkyl having 7 to 13 carbon atoms, or alkanoyl having 1 to 5 carbon atoms can be produced by alkylation or acylation of amino groups in compounds represented by formula (Ic) ($R^1$, $R^2$, $R^3$, $R^5$, m and $R^{10}$ are defined as the same as the above) according to a general method, as shown in Scheme 9.

Scheme 9

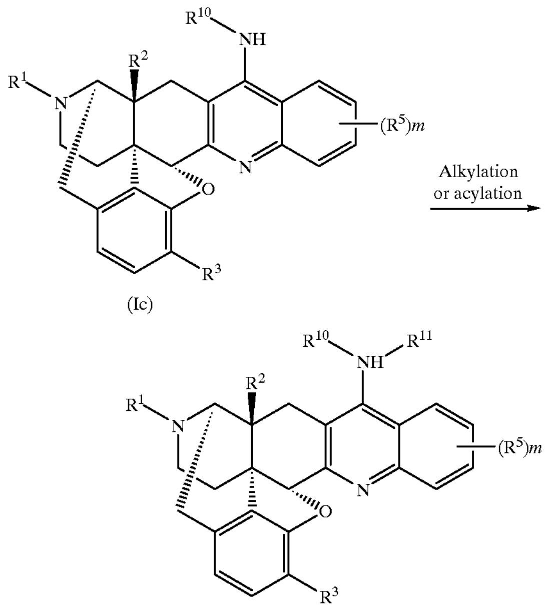

(Ic)

(Id)

In the scheme 9, of compounds represented by formula (Ic) and used as raw materials, compounds represented by formula (Ic') ($R^1$, $R^2$, $R^3$, $R^5$ and m are defined as the same as the above) in which $R^{10}$ is $R^{10a}$ which is alkyl having 1 to 5 carbon atoms, aralkyl having 7 to 13 carbon atoms, or alkanoyl having 1 to 5 carbon atoms, can be produced by alkylation or acylation of the amino groups by a general method of converting the amino groups using compounds represented by formula (Ib) as raw materials, as shown in Scheme 10.

Scheme 10

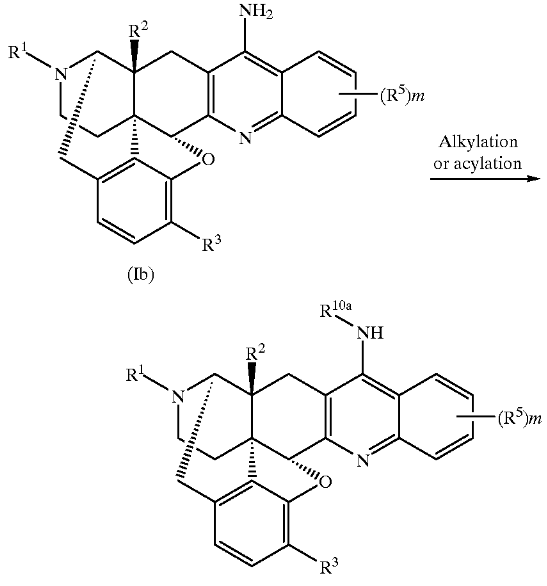

(Ib)

(Ic')

As described above, examples of the general method of converting the amino groups include (1) a method using a halide $R^{11}$—$X^1$ (wherein $X^1$ is defined as the same as the above) in the presence of an appropriate base, (2) reductive amination reaction using an appropriate aldehyde $R^{11a}$—CHO (wherein $R^{11a}$ represents a group obtained by removing a methylene terminal from $R^{11}$) and a reducing agent such as sodium cyanoborohydride, sodium triacetoxyborohydride, or the like, or hydrogenation reaction, (3) acylation reaction using an appropriate acid chloride $R^{11b}$—CO—Cl ($R^{11b}$ represents a group obtained by removing a carbonyl terminal from $R^{11}$) according to a normal method, and (4) an alkylation method comprising acylation using an appropriate acid chloride $R^{11b}$—CO—Cl ($R^{11b}$ is defined as the same as the above) and then reduction of amide by using a reducing agent such as lithium aluminum hydride, borane, or the like. However, of compounds represented by formula (Id), in some cases, compounds (Id) in which $R^2$ and/or $R^3$ is hydroxy are preferably produced by protecting the corresponding hydroxy groups of the compounds (Ic) as raw materials by appropriate protective groups, and then removing the protective groups by the above alkylation or acylation method.

The method shown in Scheme 9 is described in further detail below. Of the compounds of formula (Id) of the present invention, compounds in which $R^{10}$ is hydrogen, alkyl having 1 to 5 carbon atoms, or aralkyl having 7 to 13 carbon atoms, and $R^{11}$ is alkyl having 1 to 5 carbon atoms, or aralkyl having 7 to 13 carbon atoms, can simply be produced by reacting compounds represented by formula (Ic) of the present invention and aldehyde represented by $R^{11a}$—CHO ($R^{11a}$ represents a group obtained by removing terminal methylene from $R^{11}$) under acidic or basic conditions, and then reducing the resultant imine or iminium compounds. The reaction of converting to the imine or iminium compounds is generally effected by using an alcoholic solvent such as methanol, ethanol, or the like, an ether solvent such as THF or the like, or a hydrocarbon solvent such as benzene, toluene, or the like as a solvent, hydrochloric acid, sulfuric acid, acetic acid, p-toluenesulfonic acid, camphorsulfonic acid, or titanium tetrachloride as an acid, and piperidine or the like as a base; the solvent, the acid and the base are not limited to these compounds. General methods of reduction reaction include methods using sodium borohydride, sodium cyanoborohydride, sodium triacetoxyborohydride, lithium borohydride, or the like as a reducing agent in an alcoholic solvent such as methanol, ethanol, or the like; the reduction methods are not limited to these methods.

For example, of the compounds of formula (Id) of the present invention, compounds in which $R^{10}$ is hydrogen, alkyl having 1 to 5 carbon atoms, or aralkyl having 7 to 13 carbon atoms, and $R^{11}$ is alkanoyl having 1 to 5 carbon atoms, can be produced by condensation of compounds represented by formula (Ic) of the present invention with a carboxylic acid chloride $R^{11a}$—CO—Cl, a carboxylic acid anhydride $(R^{11a}CO)_2O$ or a carboxylic acid $R^{11a}$—COOH ($R^{11a}$ is defined as the same as the above). Condensation with a carboxylic acid chloride $R^{11a}$—CO—Cl or a carboxylic acid anhydride $(R^{11a}CO)_2O$ can be effected by using, as a base, a tertiary amine such as triethylamine, diisopropylethylamine, proton sponge, or the like, an organic base such as pyridine, dimethylaminopyridine, imidazole, or the like, or an inorganic base such as potassium carbonate, sodium carbonate, sodium hydrogencarbonate, sodium hydroxide, potassium hydroxide, or the like; as a solvent, a halogenated hydrocarbon solvent such as dichloromethane, chloroform, carbon tetrachloride, 1,2-dichloroethane, or the like, an ether solvent such as diethyl ether, THF, dioxane, or the like, pyridine, water or a solvent mixture thereof. Condensation with a carboxylic acid $R^{11a}$—COOH can be effected by using any one of generally known condensation agents. In condensation reaction with a carboxylic acid chloride, a carboxylic acid anhydride or a carboxylic acid, particularly in the case of compounds represented by formula (Ic) in which $R^2$ or $R^3$ is hydroxy, the hydroxyl groups also react at the same time to obtain products. In this case, the products are hydrolyzed under basic conditions after the condensation reaction to obtain compounds represented by formula (Id) in which $R^2$ and $R^3$ are hydroxy. The hydrolysis reaction can be effected by using an inorganic base such as potassium carbonate, sodium carbonate, sodium hydrogencarbonate, sodium hydroxide, potassium hydroxide, or the like, particularly potassium carbonate or sodium hydroxide, as a base in a solvent such as water, an alcoholic solvent such as methanol, ethanol, or the like, an ether solvent such as diethyl ether, DME, dioxane, or the like, a mixture thereof, or a solvent to which a halogenated hydrocarbon solvent such as dichloromethane, chloroform or the like is appropriately added in the case of low solubility. For example, of the compounds (Id) of the present invention, particularly compounds in which both $R^{10}$ and $R^{11}$ are methyl can simply be produced by general methylation reaction using compounds represented by formula (Ib) as raw materials, and formaldehyde and formic acid.

Of the compounds represented by formula (I) of the present invention, compounds represented by formula (Ie) ($R^1$, $R^2$, $R^3$, $R^5$, m and $R^{12}$ are defined as the same as the above) in which $R^4$ is $OR^{12}$ can be produced by diazotization of compounds represented by formula (Ib) of the present invention, and then solvolysis by reacting with water or an alcohol represented by $R^{12}OH$ ($R^{12}$ is defined as the same as the above), as shown in Scheme 11.

The diazotization reaction can generally be effected by using sodium nitrite in coexistence with an acid such as hydrochloric acid, sulfuric acid, phosphoric acid, or the like in a solvent such as water, acetic acid or a solvent mixture thereof, or using alkyl nitrite such as isoamyl nitrite in a solvent such as methanol, ethanol, or the like. The subsequent solvolysis can generally be carried out by heating in water or an alcoholic solvent represented by $R^{12}OH$ ($R^{12}$ is defined as the same as the above).

Scheme 11

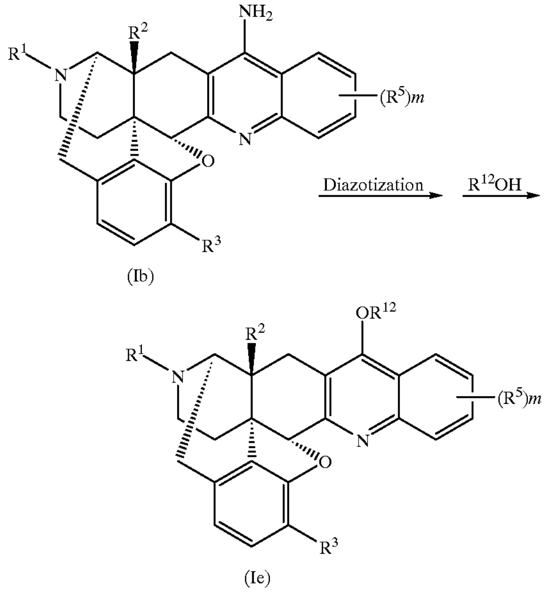

(Ib)

(Ie)

Of the compounds represented by formula (I) of the present invention, compounds represented by formula (If) ($R^1$, $R^2$, $R^3$, $R^5$, m and $R^{17}$ are defined as the same as the above) in which $R^4$ is substituent $R^{4a}$ comprising alkyl having 1 to 5 carbon atoms, hydroxyalkyl having 1 to 5 carbon atoms, or aryl having 6 to 12 carbon atoms (which may be substituted by at least one substituent $R^{17}$) can be produced by reacting ketone compounds represented by formula (VII) and compounds represented by the formula (VIIIb) ($R^5$, m and $R^{4a}$ are defined as the same as the above) in which of the aminocarbonyl derivatives represented by the formula (VIII) shown in Scheme 1, $R^4$ is $R^{4a}$, under acidic conditions, as shown in Scheme 12.

Examples of the solvent include alcoholic solvents such as methanol, ethanol, and the like; organic carboxylic acid solvents such as formic acid, acetic acid, propionic acid, and the like; aprotic polar solvents such as DMF, DMSO, or the like, hydrocarbon solvents such as benzene, toluene, and the like; the use of ethanol or acetic acid generally produces sufficiently satisfactory effects. Examples of the acid include a wide range of acids such as inorganic acids such as hydrochloric acid, sulfuric acid, nitric acid, phosphoric acid, and the like; organic carboxylic acids such as formic acid, acetic acid, propionic acid, and the like; organic sulfonic acids such as methanesulfonic acid, p-toluenesulfonic acid, camphorsulfonic acid, and the like, Lewis acids such as zinc chloride, phosphorus trichloride, scandium triflate, and the like. Particularly, hydrochloric acid, sulfuric acid, acetic acid, methanesulfonic acid, and scandium triflate are preferable; particularly, the use of acetic acid or methanesulfonic acid produces good results.

Scheme 12

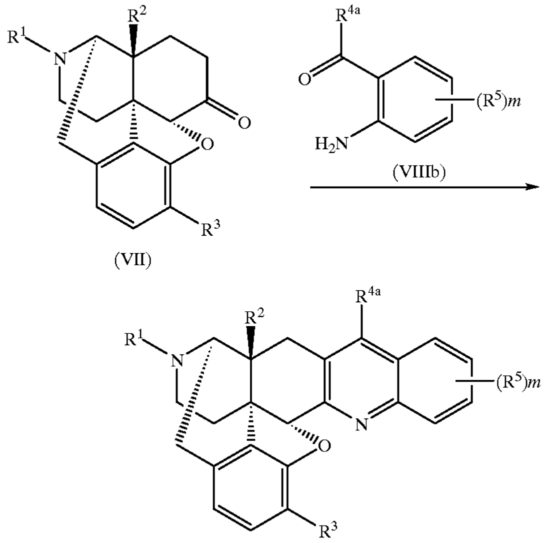

(VII)

(VIIIb)

(If)

Of the compounds represented by formula (I) of the present invention, compounds represented by formula (Ig) ($R^1$, $R^2$, $R^3$, $R^5$, m and $R^{13}$ are defined as the same as the above) in which $R^4$ is $COOR^{13}$ can be produced by quinoline synthesis reaction using ketone compounds represented by formula (VII) and aminoketo acid derivatives represented by formula (VIIIc) ($R^5$, m and $R^{13}$ are defined as the same as the above) in which in the aminocarbonyl derivatives represented by formula (VIII) shown in Scheme 1, $R^4$ is $COOR^{13}$, as shown in Scheme 13.

Of the compounds represented by formula (Ig), compounds represented by formula (Ih) ($R^1$, $R^2$, $R^3$, $R^5$ and m are defined as the same as the above) in which $R^{13}$ is hydrogen can also be produced by quinoline synthesis reaction using ketone compounds represented by formula (VII) and isatin derivatives represented by formula (VIIId)

($R^5$ and m are defined as the same as the above), which are cyclic anhydrides of aminoketo acid derivatives (VIIIc), as shown in Scheme 14.

Scheme 13

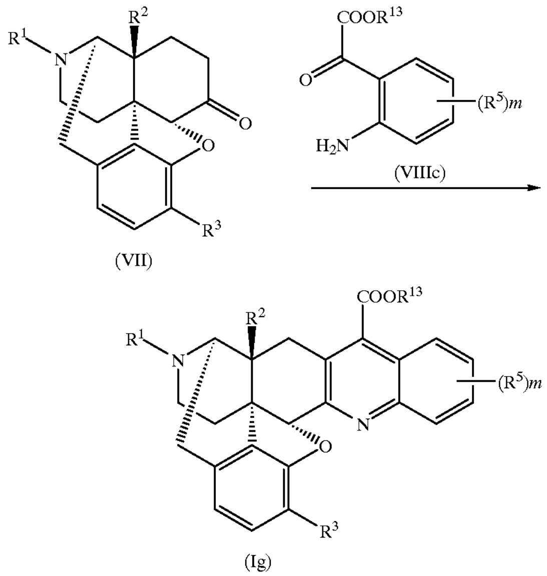

(VII) (VIIIc) (Ig)

Scheme 14

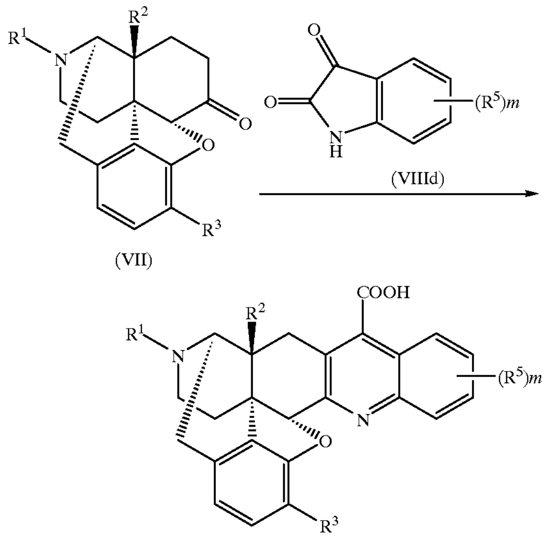

(VII) (VIIId) (Ih)

In Scheme 14, quinoline synthesis reaction can be effected in the presence of an appropriate acid or base according to demand. Examples of the base used include sodium hydroxide, potassium hydroxide, sodium alkoxide, and the like; and preferable examples of the solvent used in this case include alcoholic solvents such as methanol, ethanol, and the like; ether solvents such as diethyl ether, THF, and the like; water: and solvent mixtures thereof. Examples of the acid include inorganic acids such as hydrochloric acid, sulfuric acid, nitric acid, phosphoric acid, and the like; organic carboxylic acids such as formic acid, acetic acid, propionic acid, and the like; organic sulfonic acids such as methanesulfonic acid, p-toluenesulfonic acid, camphorsulfonic acid, and the like; Lewis acids such as zinc chloride, phosphorus trichloride, scandium triflate, and the like; particularly hydrochloric acid, sulfuric acid acetic acid are preferred. In this case, examples of the solvent used include alcoholic solvents such as methanol, ethanol, and the like; organic carboxylic acids such as formic acid, acetic acid, propionic acid, and the like; aprotic solvents such as DME and the like; water; and solvent mixtures thereof.

Of the compounds represented by formula (If) shown in Scheme 12, compounds in which $R^4$ is hydroxyalkyl having 1 to 5 carbon atoms can be produced as described above; particularly, compounds represented by formula (Ii) ($R^1$, $R^2$, $R^3$, $R^5$ and m are defined as the same as the above) in which $R^4$ is hydroxymethyl can also be produced by reduction of compounds of the present invention represented by formula (Ig), as shown in Scheme 15.

Scheme 15

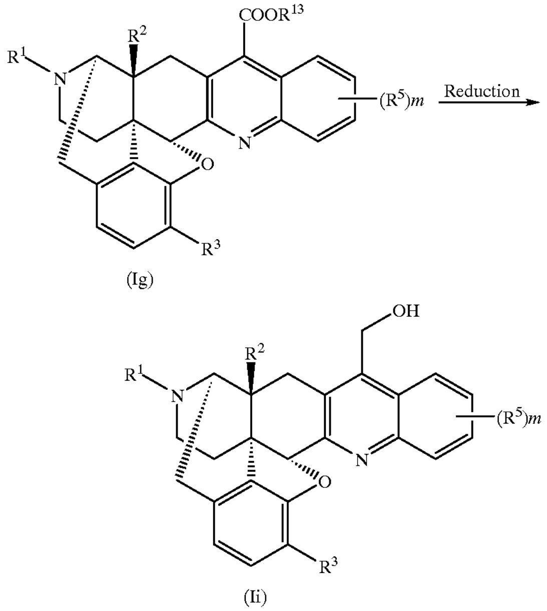

(Ig) (Ii)

Examples of reducing agents include metal halide compounds having strong reducing power, such as lithium aluminum hydride, diisobutylaluminum hydride, lithium borohydride, diborane, a combination of an appropriate Lewis acid and sodium borohydride, and the like; particularly aluminum lithium hydride, lithium borohydride, and diborane are preferable. In the use of lithium aluminum hydride, lithium borohydride, or diborane, ether solvents such as THF, diethyl ether, DME, dioxane, and the like are preferably used as the solvent; particularly THF is preferably used. In the case of diisobutylaluminum hydride, hydrocarbon solvents such as benzene, toluene, and the like are preferably used. In the case of sodium borohydride, alcohollic solvents such as methanol, ethanol, and the like are preferably used.

Of the compounds represented by formula (Ig) of the present invention shown in Scheme 13, compounds represented by formula (Ig') ($R^1$, $R^2$, $R^4$, $R^5$ and m are defined as the same as the above) in which $R^{13}$ is $R^{13a}$ which is alkyl having 1 to 5 carbon atoms, or aralkyl having 7 to 13 carbon atoms can be produced by the method shown in Scheme 13; such compounds can also be produced by another method comprising esterifying the compounds represented by formula (Ih) of the present invention, as shown in Scheme 16.

Examples of the esterification method using compounds represented by formula (Ih) of the present invention include (1) a method of reacting with an alcohol represented by $R^{13a}OH$ ($R^{13a}$ is defined as the same as the above) in the presence of an appropriate acid, (2) a method of reacting with thionyl chloride or oxalyl chloride to convert the compounds to acid chlorides represented by formula (XIII) ($R^1$, $R^2$, $R^3$, $R^5$ and m are defined as the same as the above), and then reacting with an alcohol represented by $R^{13a}OH$ ($R^{13a}$ is defined as the same as the above) in the presence of an appropriate base according to demand, and a method of reacting with diazomethane or trimethylsilyldiazomethane to obtain methyl esters, particularly when $R^{13a}$ is methyl; the esterification methods are not limited to these methods.

amidation of compounds represented by formula (Ih) of the present invention, as shown in Scheme 17.

Examples of the amidation method using the compounds represented by formula (Ih) include (1) a method of condensation using an amine represented by $R^{14}R^{15}NH$ ($R^{14}$ and $R^{15}$ are defined as the same as the above) and an appropriate condensation agent according to demand, and (2) a method of reacting with thionyl chloride or oxalyl chloride to convert to acid chlorides represented by formula (XIII), and then condensation with an amine represented by Scheme 16

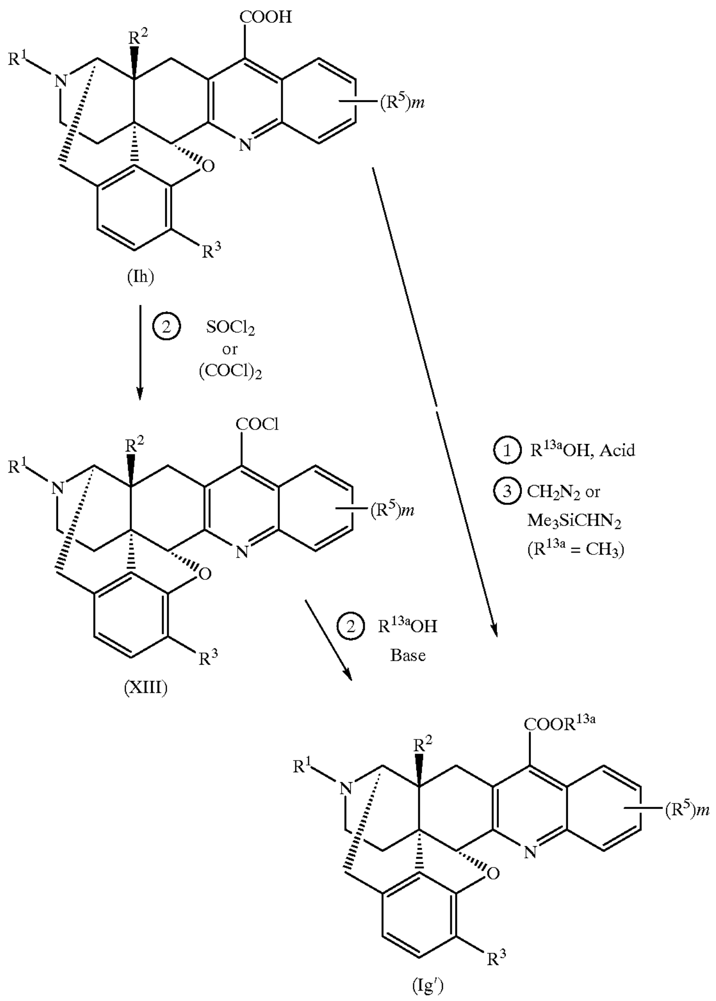

Of the compounds represented by formula (I) of the present invention, compounds represented by formula (Ii) ($R^1$, $R^2$, $R^3$, $R^5$, m $R^{14}$ and $R^{15}$ are defined as the same as the above) in which $R^4$ is $CONR^{14}R^{15}$ can be produced by $R^{14}R^{15}NH$ ($R^{14}$ and $R^{15}$ are defined as the same as the above) in the presence of an appropriate base according to demand; the amidation method is not limited to these methods.

Scheme 17

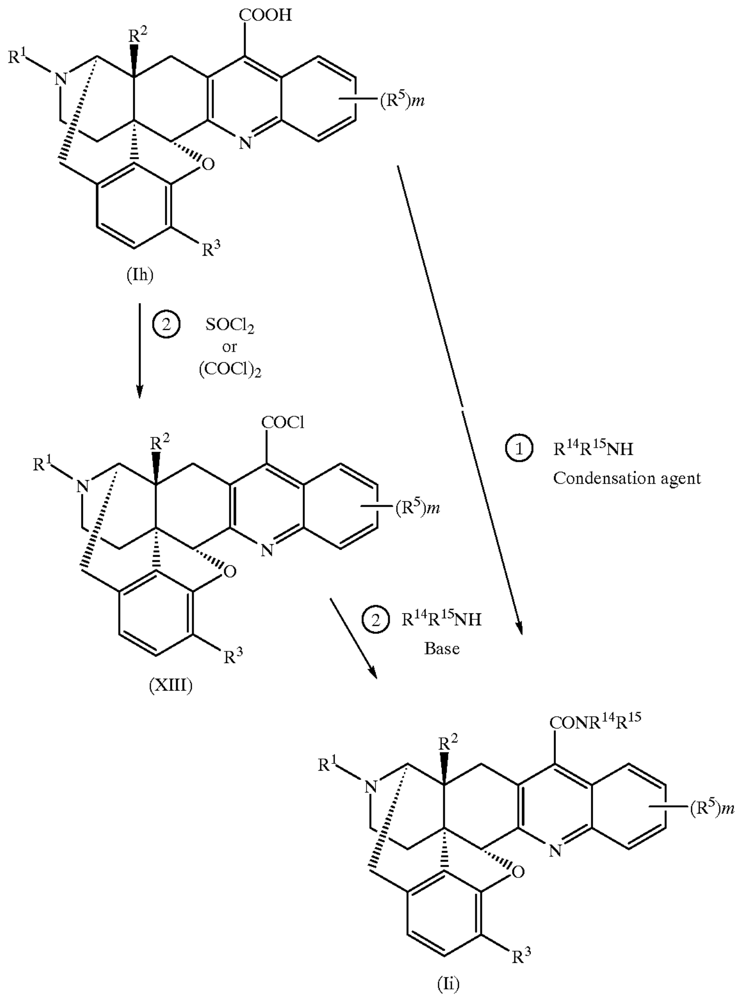

(Ih)

(XIII)

(Ii)

Of the compounds represented by formula (I) of the present invention, compounds represented by formula (Ij) ($R^1$, $R^2$, $R^3$ and $R^5$ are defined as the same as the above) in which $R^4$ and $R^5$ substituted at the peri-position form together $R^4$—$R^5$, $NR^{16}CO$, wherein $R^{16}$ is hydrogen, can be produced by quinoline synthesis reaction using ketone compounds represented by formula (VII) and aminophthalonitrile derivatives represented by formula (IXa) ($R^5$ is defined as the same as the above) in the presence of an appropriate acid according to demand, as shown in Scheme 18.

Scheme 18

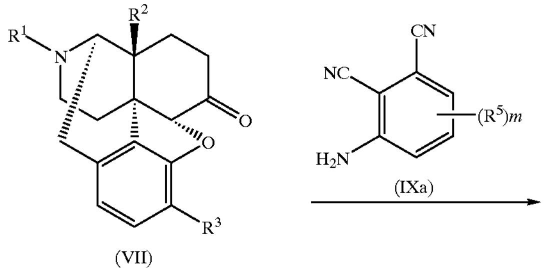

(VII)

(IXa)

-continued

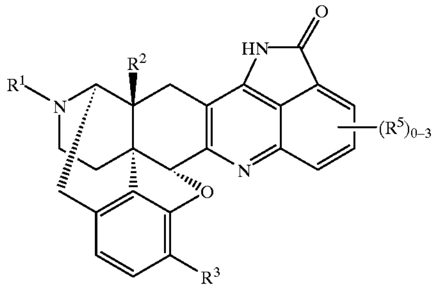

(Ij)

Examples of the solvent include alcoholic solvents such as methanol, ethanol, and the like; organic carboxylic acid solvents such as formic acid, acetic acid, propionic acid, and the like; hydrocarbon solvents such as benzene, toluene, and the like; aprotic polar solvents such as DMF, DMSO, and the like; and solvent mixtures thereof; particularly ethanol, acetic acid, toluene, and a DMF-benzene mixed solvent are preferable. As reaction conditions, normal heating conditions, azeotropic conditions, heating concentration conditions, and the like are preferably used. Examples of the acid include inorganic acids such as hydrochloric acid, sulfuric acid, nitric acid, phosphoric acid, and the like; organic carboxylic acids such as formic acid, acetic acid, propionic acid, and the like; organic sulfonic acids such as methanesulfonic acid, p-toluenesulfonic acid, camphorsulfonic acid, and the like; Lewis acids such as zinc chloride, zinc trichloride, phosphorus trichloride, scandium triflate, and the like. Particularly, acetic acid which is also used as a solvent, methanesulfonic acid, and scandium triflate are preferable.

At the same time, compounds represented by formula (Io) below are sometimes obtained. Particularly, when a DMF-benzene mixed solvent is used as the solvent, and methanesulfonic acid is used as the acid, the compounds represented by formula (Io) can be produced in high yield.

(Io)

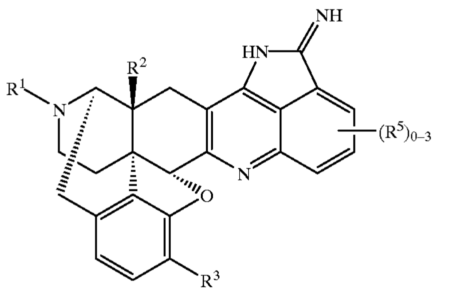

Of the compounds represented by formula (I) of the present invention, compounds represented by formula (Ip) ($R^1$, $R^2$, $R^3$ and $R^5$ are defined as the same as the above) in which $R^4$ and $R^5$ substituted at the peri-position form together $R^4$—$R^5$, $NR^{16}CO$, wherein $R^{16}$ is alkyl having 1 to 5 carbon atoms, cycloalkylalkyl having 4 to 7 carbon atoms, aralkyl having 7 to 13 carbon atoms, or alkanoyl having 1 to 5 carbon atoms, can be produced by alkylation or acylation of compounds represented by formula (Ij) according to a general method, as shown in Scheme 18-2.

Scheme 18-2

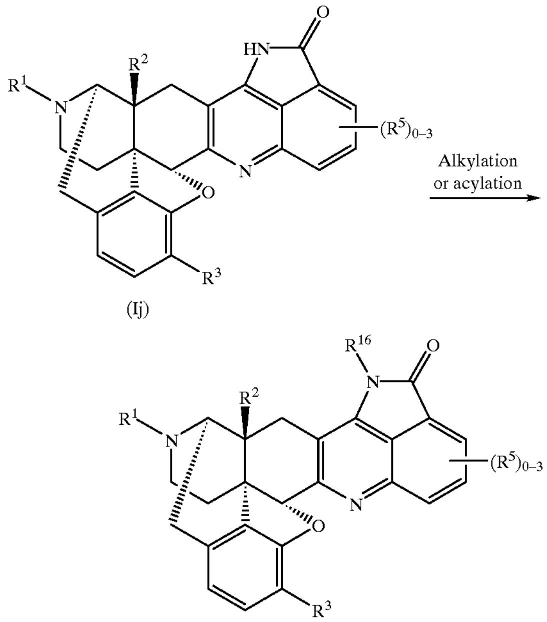

(Ij)

(Ip)

As described above, general methods of converting amino groups include (1) a method of alkylation using a halide $R^{16}$—$X^1$ ($X^1$ is defined as the same as the above) in the presence of an appropriate base, and (2) a method of acylation using an appropriate acid chloride $R^{16b}$—CO—Cl ($R^{16b}$ represents a group obtained by removing one terminal carbonyl from $R^{16}$) according to a general method.

Of the compounds represented by formula (I) of the present invention, compounds represented by formula (Ik) ($R^1$, $R^2$, $R^3$, $R^5$ and $R^7$ are defined as the same as the above) in which $R^4$ is $NR^{10}R^{11}$, both $R^{10}$ and $R^{11}$ are hydrogen, $R^5$ is substituted at the peri-position of $R^4$ and is $COOR^7$, can be produced by solvolysis of the compounds represented by formula (Ij) of the present invention under generally used conditions such as acidic or basic conditions in water or an alcohol represented by $R^7OH$ ($R^7$ is defined as the same as the above), as shown in Scheme 19.

Scheme 19

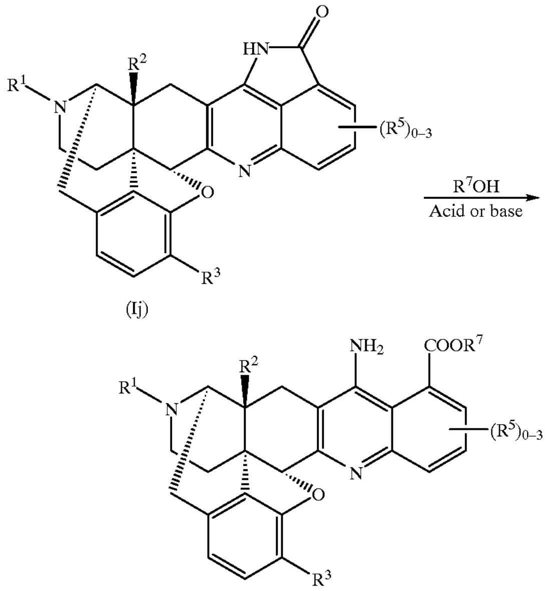

(Ij)

(Ik)

Examples of the acid include inorganic acids such as hydrochloric acid, sulfuric acid, nitric acid, phosphoric acid, and the like; the use of hydrochloric acid generally produces good results. Examples of the base include inorganic bases such as potassium carbonate, sodium carbonate, sodium hydrogencarbonate, sodium hydroxide, potassium hydroxide, and the like; the use of sodium hydroxide generally produces good results.

Of the compounds represented by formula (I) of the present invention, compounds represented by formula (Im) ($R^1$, $R^2$, $R^4$, $R^5$ and m are defined as the same as the above) in which $R^3$ is methoxy can be converted to compounds represented by formula (In) ($R^1$, $R^2$, $R^4$, $R^5$ and m are defined as the same as the above) in which $R^3$ is hydroxy, by general demethylation reaction of phenolic methyl ether, as shown in Scheme 20.

Scheme 20

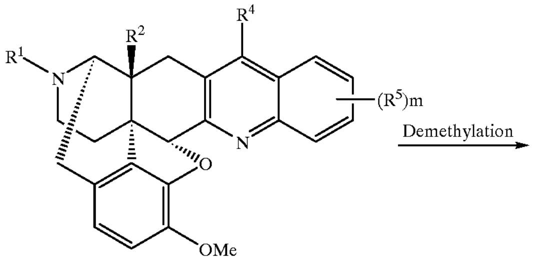

(Im)

-continued

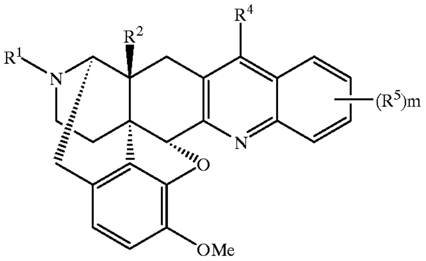

(Im)

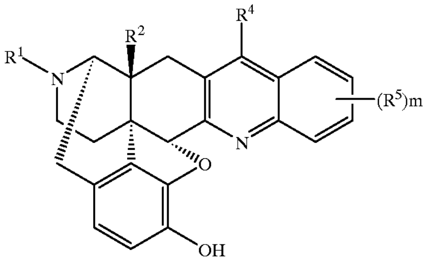

(In)

The demethylation reaction can be effected under generally known conditions; particularly the reaction can be effected by a method using dichloromethane, chloroform or 1,2-dichloroethane as a solvent, and boron tribromide [Document: Tetrahedron Vol. 24, 2289 (1968)] or boron trichloride, or a method using a thioalkoxide, particularly sodium thioethoxide [Document: Tetrahedron Lett., 1327 (1970)] in DMF generally. The demethylation reaction also permits demethylation of a methoxy group which is present as a substituent other than $R^3$ in the compounds represented by formula (I) of the present invention.

Conversely, of the compounds represented by formula (I) of the present invention, compounds represented by formula (Im) ($R^1$, $R^2$, $R^4$, $R^5$ and m are defined as the same as the above) in which $R^3$ is methoxy can also be produced by methylation of the phenolic hydroxyl group in compounds represented by formula (In) ($R^1$, $R^2$, $R^4$, $R^5$ and m are defined as the same as the above) in which $R^3$ is hydroxy, according to a general method, as shown in Scheme 21.

Scheme 21

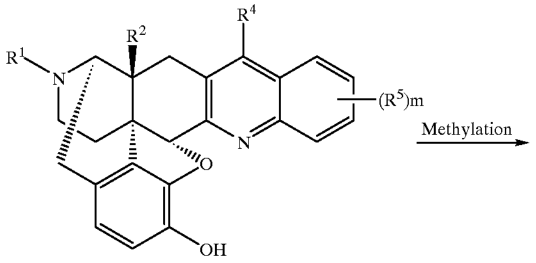

(In)

The methylation reaction can be effected under generally known conditions; particularly the reaction can preferably be effected by a method using methyl iodide in coexistence with an inorganic base such as sodium carbonate, potassium carbonate, lithium carbonate, sodium hydroxide, potassium hydroxide, or the like, in a solvent such as DMF, acetone, or the like, or in the presence of sodium hydride in an ether solvent such as THF or the like, or a method using diazomethane in coexistence with silica gel in a solvent such as diethyl ether or the like.

As a result of in vivo pharmacological evaluation, the quinolinomorphinan derivatives of the present invention represented by formula (I) exhibit excellent effects on disorders of the cerebral nerve cells, as described in the examples below. Therefore, the compounds of the present invention can be used as agents for curing or preventing worsening of cerebral disorders, i.e., medicines useful for ameliorating various cerebral diseases and aftereffects thereof, and preventing the recurrence thereof. Specifically, it was made apparent that the compounds of the present invention can be used as therapeutic agents for cerebral stroke, therapeutic agents for traumatic cerebral diseases, therapeutic agents for cerebral edema, therapeutic agents for ischemic diseases, therapeutic agents for cerebral neurodegenerative diseases, and therapeutic agents for aftereffects of cerebral diseases. The compounds of the present invention exhibited the excellent neuroprotective action on damages of the cerebral nerve cells, and it was thus found that the compounds of the present invention are useful as cerebral neuroprotective agents which inhibit ischemic or hemorrhagic cerebrovascular diseases, traumatic cerebral diseases and various cerebral neurodegenerative diseases by the protecting action on the cerebral nerve cells.

The therapeutic agents for cerebral stroke are medicines used for curing, ameliorating or preventing ischemic or hemorrhagic cerebral stroke, specifically, cerebral infarction (cerebral embolism, cerebral thrombosis), cerebral hemorrhage, subarachnoid hemorrhage, transient ischemic attack (TIA), hypertensive encephalophathy, etc. The therapeutic agents for traumatic cerebral diseases are medicines used for ameliorating cerebral disorder caused by trauma and functional disorder of the brain accompanied thereby, and ameliorating aftereffects. The therapeutic agents for cerebral edema are medicines used for ameliorating, curing or preventing cerebral edema caused by a lesion of hemorrhage, infarction, tumor, trauma, or the like which occurs in the brain, or an increase in intracranial pressure to ameliorate disorders of the cerebral nerve cells due to cerebral edema. The therapeutic agents for ischemic diseases are medicines used for curing, ameliorating or preventing the cerebral disorders caused by insufficient supply of oxygen and glucose to the cerebral nerve cells on the basis of ischemia due to hypoxia, hypoglycemia, drug poisoning, or the like. The therapeutic agents for cerebral neurodegenerative diseases are medicines used for curing, ameliorating or preventing cerebral diseases such as Alzheimer's disease, Parkinson's disease, Huntington's chorea, diffuse Lewy's bodies, Creutzfeldt-Jakob's disease, and the like, which cause disorders of the cerebral nerve cells accompanied with degeneration of the nerve cells. The therapeutic agents for aftereffects of cerebral diseases are medicines used for curing, ameliorating or preventing aftereffects caused by the above cerebral disorders, such as cerebrovascular dementia, amnesia, disorder of consciousness, motor paralysis, allophasis, sensory disorder, mental disorder, memory disorder, and the like.

In the clinical use of the agent for curing or preventing worsening of cerebral disorder of the present invention, a free base or salt thereof may be used, and additives such as an excipient, a stabilizer, a preservative, a buffer, a solubilizer, an emulsifier, a diluent, an isotonizing agent, etc. may be appropriately mixed. As an administration form, either parenteral administration or oral administration produces sufficient effects. Administration formulations include an injection, a tablet, a liquid, a capsule, granules, a powder, and the like, and these formulations can be produced by known formulation techniques. Although the dosage is appropriately selected in accordance with the symptoms, age and body weight of a patient, the administration method, etc., the amount of the effective component per adult is 0.0001 mg to 10 g per day, preferably 0.001 mg to 1 g per day, and the agent can be administered once or divided into several doses.

EXAMPLES

Although the present invention is described in detail below with reference to reference examples and examples, the present invention is not limited to these example.

Reference Example 1

17-cyclopropylmethyl-6,7-dehydro-4,5α-epoxy-3,14β-dihydroxy-6,7,2',3'-quinolinomorphinan 1.methanesulfonate This compound was synthesized in accordance with the method disclosed in U.S. Pat. No. 4,816,586. 4.69 g (12.4 mmol) of 17-cyclopropylmethyl-6-oxo-4,5α-epoxy-3,14β-dihydroxymorphinan hydrochloride, and 3.0 g of o-aminobenzaldehyde were added to 100 ml of ethanol, and 0.81 ml (12.4 mmol) of methanesulfonic acid was added to the resultant mixture, followed by heating under reflux for 2.5 hours. The reaction solution was concentrated under reduced pressure, and an aqueous saturated sodium hydrogencarbonate solution to the resultant residue, followed by extraction with ethyl acetate. The organic layers were together dried over anhydrous sodium sulfate, and then concentrated. Methanol was added to the residue to obtain 4.12 g (yield 78%) of free title compound as crystals. The thus-obtained compound was dissolved in methanol, and methanesulfonic acid was added to the resultant solution to isolate a salt of the compound.

Reference Example 2

17-cyclopropylmethyl-6,7-dehydro-4,5α-epoxy-14β-hydroxy-3-methoxy-6,7,2',3'-(7',8'-benzoquinolino) morphinan 2.methanesulfonate 3.18 g (7.75 mmol) of 17-cyclopropylmethyl-6-oxo-4,5α-epoxy-14β-hydroxy-3-methoxy-7-[(dimethylamino) methylene] morphinan produced in accordance with the method disclosed in the document [J. Med. Chem., 24, 1445 (1981)] was dissolved in 15 ml of trifluoroacetic acid, and 5.57 g (31.0 mmol) of α-naphthylamine hydrochloride was added to the resultant solution, followed by stirring under heating at 120° C. After 3 ml of trifluoroacetic acid was distilled off, the residue was heated under reflux at 120° C. for 23 hours. After the reaction solution was concentrated, an aqueous saturated sodium hydrogencarbonate solution was added to the residue, followed by extraction with chloroform. The organic layers were together dried over anhydrous sodium sulfate, and then concentrated. The obtained crude product was purified by medium pressure silica gel column chromatography, and then recrystallized from chloroform-methanol to obtain 3.03 g (80%) of salt-free title compound. The thus-obtained compound was dissolved in methanol-THF, and methanesulfonic acid was added to the resultant solution to isolate a salt of the compound.

Reference Examples 3–7

In accordance with the method of Reference Example 2, 4-methoxyaniline, 2-phenylaniline, 1-amino-5,6,7,8-tetrahydronaphthalene, 4-methylaniline, and 4-(dimethylamino)aniline hydrochloride were used in place of α-naphthylamine hydrochloride to obtain 17-cyclopropylmethyl-6,7-dehydro-4,5α-epoxy-14β-hydroxy-3-methoxy-6,7,2',3'-(6'-methoxyquinolino) morphinan 3, 17-cyclopropylmethyl-6,7-dehydro-4,5α-epoxy-14β-hydroxy-3-methoxy-6,7,2',3'-(8'-phenylquinolino)morphinan 4, 17-cyclopropylmethyl-6,7-dehydro-4,5α-epoxy-14β-hydroxy-3-methoxy-6,7,2',3'-(7',8'-cyclohexenoquinolino)morphinan 5, 17-cyclopropylmethyl-6,7-dehydro-4,5α-epoxy-14β-hydroxy-3-methoxy-6,7,2',3'-(6'-methylquinolino) morphinan 6, and 17-cyclopropylmethyl-6,7-dehydro-4,5α-epoxy-14β-hydroxy-3-methoxy-6,7,2',3'-[6'-(dimethylamino)quinolino]morphinan 7, respectively.

Examples 1–2

In accordance with the method of Reference Example 2, 5-aminoacenaphthene hydrochloride and 1-aminofluorene were used in place of α-naphthylamine hydrochloride to obtain 17-cyclopropylmethyl-6,7-dehydro-4,5α-epoxy-14β-hydroxy- 3-methoxy-6,7,2',3'-(6',6"-ethano-7',8'-benzoquinolino)morphinan 8 and 17-cyclopropylmethyl-6,7-dehydro-4,5α-epoxy-14β-hydroxy-3-methoxy-6,7,2',3'-(7',8',3",2"-indenoquinolino)morphinan 9, respectively.

Example 3

17-cyclopropylmethyl-6,7-dehydro-4,5α-epoxy-3,14β-dihydroxy-6,7,2',3'-(4'-aminoquinolino)morphinan 10.hydrochloride 1.25 g (3.66 mmol) of 17-cyclopropylmethyl-6-oxo-4,5α-epoxy-3,14β-dihydroxymorphinan, and 0.50 g (4.39 mmol) of o-aminobenzonitrile were added to 10 ml of acetic acid, and the resultant mixture was heated under reflux for 25 hours. The reaction solution was concentrated under reduced pressure, and an aqueous saturated sodium hydrogencarbonate solution was added the resultant residue, followed by extraction with ethyl acetate. The organic layers were together dried over anhydrous sodium sulfate and then concentrated, and the resultant crude product was purified by medium pressure silica gel column chromatography (chloroform:methanol=100:1→20:1) to obtain 0.59 g (37%) of free title compound. The thus-obtained compound was suspended in methanol, and hydrochloric acid was added to the suspension to isolate a salt of the compound.

Examples 4–14

In accordance with the method of Example 3, 2-amino-4-chlorobenzonitrile, 2-amino-4-methylbenzonitrile, 2-amino-3-chlorobenzonitrile, 2-amino-4,5-dimethoxybenzonitrile, 2-amino-3-fluorobenzonitrile, 2-amino-5-nitrobenzonitrile, 2-amino-5-chlorobenzonitrile (prepared from 2-nitro-5-chlorobenzonitrile), 2-amino-4-trifluoromethylbenzonitrile (prepared from 2-nitro-4- trifluoromethylbenzonitrile), 1-amino-2-naphthonitrile (prepared from α-naphthylamine), 2-amino-5-methylbenzonitrile (prepared from 4-methylaniline), and 2-amino-5-methoxybenzonitrile (prepared from 4-methoxyaniline) were used in place of o-aminobenzonitrile to obtain 17-cyclopropylmethyl-6,7-dehydro-4,5α-epoxy-3,14β-dihydroxy-6,7,2',3'-(4'-amino-7'-chloroquinolino)morphinan 11, 17-cyclopropylmethyl-6,7-dehydro-4,5α-epoxy-3,14β-dihydroxy-6,7,2',3'-(4'-amino-7'-methylquinolino)morphinan 12, 17-cyclopropylmethyl-6,7-dehydro-4,5α-epoxy-3,14β-dihydroxy-6,7,2',3'-(4'-amino-8'-chloroquinolino) morphinan 13, 17-cyclopropylmethyl-6,7-dehydro-4,5α-epoxy-3,14β-dihydroxy-6,7,2',3'-(4'-amino-6',7'-dimethoxyquinolino)morphinan 14, 17-cyclopropylmethyl-6,7-dehydro-4,5α-epoxy-3,14β-dihydroxy-6,7,2',3'-(4'-amino-8'-fluoroquinolino)morphinan 15, 17-cyclopropylmethyl-6,7-dehydro-4,5α-epoxy-3,14β-dihydroxy-6,7,2',3'-(4'-amino-6'-nitroquinolino)morphinan 16, 17-cyclopropylmethyl-6,7-dehydro-4,5α-epoxy-3,14β-dihydroxy-6,7,2',3'-(4'-amino-6'-chloroquinolino) morphinan 17, 17-cyclopropylmethyl-6,7-dehydro- 4,5α-epoxy-3,14β-dihydroxy-6,7,2',3'-(4'-amino-7'-trifluoromethylquinolino)morphinan 18, 17-cyclopropylmethyl-6,7-dehydro-4,5α-epoxy-3,14β-dihydroxy-6,7,2',3'-(4'-amino-7',8'-benzoquinolino) morphinan 19, 17-cyclopropylmethyl-6,7-dehydro-4,5α-epoxy-3,14β-dihydroxy-6,7,2',3'-(4'-amino-6'-methylquinolino)morphinan 20, and 17-cyclopropylmethyl-6,7-dehydro-4,5α-epoxy-3,14β-dihydroxy-6,7,2',3'-(4'-amino-6'-methoxyquinolino)morphinan 21, respectively.

Examples 15–17

In accordance with the method of Example 3, 17-cyclopropylmethyl-6-oxo-4,5α-epoxy-14β-hydroxy-3-methoxymorphinan, 17-methyl-6-oxo-4,5α-epoxy-14β-hydroxy-3-methoxymorphinan, and 6-oxo-4,5α-epoxy-14β-hydroxy-3-methoxymorphinan were used in place of 17-cyclopropylmethyl-6-oxo-4,5α-epoxy-3,14β-dihydroxymorphinan to obtain 17-cyclopropylmethyl-6,7-dehydro-4,5α-epoxy-14β-hydroxy-3-methoxy-6,7,2',3'-(4'-aminoquinolino)morphinan 22, 17 methyl-6,7-dehydro-4,5α-epoxy-14β-hydroxy-3-methoxy-6,7,2',3'-(4'-aminoquinolino)morphinan 23, and 17-acetyl-6,7-dehydro-4,5α-epoxy-14β-hydroxy-3-methoxy-6,7,2',3'-(4'-aminoquinolino)morphinan 24, respectively.

Example 18

17-cyclopropylmethyl-6,7-dehydro-4,5α-epoxy-3,14β-dihydroxy-6,7,2',3'-[4'-(acetylamino)quinolino]morphinan 25.hydrochloride 232 mg (0.53 mmol) of 17-cyclopropylmethyl-6,7-dehydro-4,5α-epoxy-3,14β-dihydroxy-6,7,2',3'-(4'-aminoquinolino)morphinan 10 was added to 5 ml of acetic anhydride, followed by heating under reflux for 20 hours. The reaction solution was concentrated, and then 5 ml of methanol and 2 ml of 3N aqueous sodium hydroxide solution were added to the residue, followed by stirring for 20 hours. The reaction solution was concentrated, and then 50 ml of aqueous saturated sodium hydrogencarbonate solution was added to the residue, followed by extraction with ethyl acetate (50 ml×3). The organic layers were together dried over anhydrous sodium sulfate, and then concentrated, and the resultant crude product was purified by medium pressure silica gel column chromatography (chloroform→chloroform:methanol=20:1) to obtain 136 mg (54%) of free title compound. The thus-obtained compound was isolated as a hydrochloride.

Example 19

17-cyclopropylmethyl-6,7-dehydro-4,5α-epoxy-3,14β-dihydroxy-6,7,2',3'-(4'-methylquinolino)morphinan 26.methanesulfonate 391 mg (1.04 mmol) of 17-cyclopropylmethyl-6-oxo-4,5α-epoxy-3,14β-dihydroxymorphinan was suspended in 6 ml of acetic acid, and 0.138 ml (1.14 mmol) of 2'-aminoacetophenone was added to the resultant suspension, followed by heating to form a solution. After heating under reflux for 4 hours, the reaction solution was allowed to cool to room temperature, and then concentrated, and 8 ml of a 2N aqueous sodium hydroxide solution was added to the residue to make the solution basic, followed by extraction with chloroform. The organic layers were together dried over anhydrous sodium sulfate, and then concentrated, and the resultant crude product was purified by silica gel column chromatography (chloroform:methanol=50:1→30:1) to obtain 470 mg of free title compound. The thus-obtained compound was dissolved in methanol, and methanesulfonic acid was added to the solution to isolate 499 mg (90%) of title compound as a salt.

Examples 20–22

In accordance with the method of Example 19, 2-aminobenzophenone, 2'-amino-4',5'-dimethoxyacetophenone, and 6'-amino-3',4'-methylenedioxyacetophenone were used in place of 2'-aminoacetophenone to obtain 17-cyclopropylmethyl-6,7-dehydro-4,5α-epoxy-3,14β-dihydroxy-6,7,2',3'-(4'-phenylquinolino)morphinan 27, 17-cyclopropylmethyl-6,7-dehydro-4,5α-epoxy-3,14β-dihydroxy-6,7,2',3'-(4'-methyl-6',7'-dimethoxyquinolino)morphinan 28, and 17-cyclopropylmethyl-6,7-dehydro-4,5α-epoxy-3,14β-dihydroxy-6,7,2',3'-(4'-methy-6',7'-dioxolenoquinolino) morphinan 29, respectively.

Example 23

17-cyclopropylmethyl-6,7-dehydro-4,5α-epoxy-3,14β-dihydroxy-6,7,2',3'-(4'-carboxyquinolino)morphinan 30.hydrochloride 511 mg (1.50 mmol) of 17-cyclopropylmethyl-6-oxo-4,5α-epoxy-3,14β-dihydroxymorphinan and 220 mg (1.50 mmol) of isatin were added to 5 ml of acetic acid, and the resultant mixture was stirred at 80° C. for 1.5 hours. To the mixture was added 1 ml of conc. hydrochloric acid, and the mixture was stirred at 110° C. for hours. To the mixture was further added 1 ml of conc. hydrochloric acid, followed by heating under reflux at 130° C. for 24 hours. The reaction solution was concentrated under reduced pressure, and chloroform was added to the resultant residue, followed by extraction with water. The aqueous layers were combined and then concentrated, and the resultant crude product was purified by a Sephadex column (methanol) to obtain 494 mg (65%) of title compound.

Example 24

In accordance with the method of Example 23, 17-cyclopropylmethyl-6-oxo-4,5α-epoxy-14β-hydroxy-3-methoxymorphinan was used in place of 17-cyclopropylmethyl-6-oxo-4,5α-epoxy-3,14β-dihydroxymorphinan to obtain 17-cyclopropylmethyl-6,7-dehydro-4,5α-epoxy-14β-hydroxy-3-methoxy-6,7,2',3'-(4'-carboxyquinolino)morphinan 31.

Example 25

17-cyclopropylmethyl-6,7-dehydro-4,5α-epoxy-3,14β-dihydroxy-6,7,2',3'-(4'-methoxycarbonylquinolino) morphinan 32.methanesulfonate 203 mg (0.43 mmol) of 17-cyclopropylmethyl-6,7-dehydro-4,5α-epoxy-3,14β-dihydroxy-6,7,2',3'-(4'-carboxyquinolino)morphinan 30 hydrochloride was dissolved in a mixed solvent containing 1 ml of methanol and 4 ml of benzene, and 2.0 ml (1.4 mmol) of trimethylsilyldiazomethane (10% hexane solution) was added dropwise to the resultant solution, followed by stirring at room temperature for 1 hour. To the reaction solution was added water, and the solution was extracted with chloroform. The organic layers were together dried over anhydrous sodium sulfate, and the concentrated, and the resultant crude product was purified by medium pressure silica gel column chromatography (chloroform→chloroform:methanol=100:1) to obtain 169 mg (81%) of free title compound. The thus-obtained compound was dissolved in methanol, and methanesulfonic acid was added to the solution to isolate a salt of the compound.

Example 26

17-cyclopropylmethyl-6,7-dehydro-4,5α-epoxy-3,14β-dihydroxy-6,7,2',3'-[4'-(hydroxymethyl)quinolino]morphinan 33.methanesulfonate 100 mg (0.21 mmol) of 17-cyclopropylmethyl-6,7-dehydro- 4,5α-epoxy-3,14β-dihydroxy-6,7,2',3'-(4'-methoxycarbonylquinolino)morphinan 32 was suspended in 5 ml of THF, and 28 mg (1.29 mmol) of lithium borohydride was added to the resultant suspension, followed by heating under reflux for 22 hours. To the reaction solution was added 10 ml of a 0.1N aqueous hydrochloric acid solution, and the resultant mixture was stirred for 10 minutes. To the mixture was added an aqueous saturated sodium hydrogencarbonate solution, and the mixture was extracted with chloroform. The organic layers were together dried over anhydrous sodium sulfate, and then concentrated, and the resultant crude product was purified by medium pressure silica gel column chromatography (chloroform→chloroform:methanol=20:1) to obtain 45 mg (48%) of free title compound. The thus-obtained compound was dissolved in methanol, and methanesulfonic acid was added to the resultant solution to isolate a salt of the compound.

Example 27

17-cyclopropylmethyl-6,7-dehydro-4,5α-epoxy-3,14β-dihydroxy-6,7,2',3'-[4',5'-[imino(oxomethano)quinolino]morphinan 34.hydrochloride 2.4 g of 17-cyclopropylmethyl-6-oxo-4,5α-epoxy-3,14β-dihydroxymorphinan was dissolved in acetic acid, and 1.2 g of 3-aminophthalonitrile (prepared by 3-nitrophthalonitrile) and 350 mg of scandium triflate were added to the resultant solution, followed by heating under reflux for 90 hours. After the reaction solution was cooled, the solvent was distilled off under reduced pressure, and 150 ml of an aqueous saturated sodium hydrogencarbonate solution was added to the residue, followed by extraction with ethyl acetate. The organic layers were together dried over anhydrous sodium sulfate and then concentrated, and the resultant crude product was purified by medium pressure silica gel column chromatography (chloroform:methanol=50:1→20:1) to obtain 650 mg (20%) of free title compound. The thus-obtained compound was isolated as a hydrochloride.

Example 28

17-cyclopropylmethyl-6,7-dehydro-4,5α-epoxy-3,14β-dihydroxy-6,7,2',3'-(4'-amino-5'-carboxyquinolino)morphinan 35.hydrochloride 240 mg (0.48 mmol) of 17-cyclopropylmethyl-6,7-dehydro-4,5α-epoxy-3,14β-dihydroxy-6,7,2',3'-[4',5'-[imino(oxomethano)]quinolino]morphinan 34 hydrochloride was dissolved in 60 ml of water, and the resultant solution was sealed in an ampoule and then allowed to stand in a constant-temperature bath at 60° C. for 5 days. After the ampoule was cooled, the reaction solution was taken out, and washed with 50 ml of ammonia-saturated chloroform and then with chloroform (50 ml×2), followed by freeze drying to obtain 220 mg of crude product. The thus-obtained crude product was purified by a Sephadex column (methanol), freeze-dried to obtain 53 mg (21%) of title compound.

Reference Example 8

17-cyclopropylmethyl-6,7-dehydro-4,5α-epoxy-3,14β-dihydroxy-6,7,2',3'-(7',8'-benzoquinolino)morphinan 36.methanesulfonate 3.03 g (6.18 mmol) of 17-cyclopropylmethyl-6,7-dehydro-4,5α-epoxy-14β-hydroxy-3-methoxy-6,7,2',3'-(7',8'-benzoquinolino)morphinan 2 was dissolved in 60 ml of anhydrous methylene chloride, and the resultant solution was cooled to 0° C. To the solution was added dropwise 18.5 ml (18.5 mmol) of a 1.0M solution of boron tribromide in methylene chloride, followed by stirring at 0° C. for 0.5 hour. To the reaction solution were added 60 ml of water and 40 ml of aqueous ammonia solution, and the resultant mixture was stirred at room temperature for 1 hour and then extracted with chloroform (100 ml×2). The organic layers were together dried over anhydrous sodium sulfate and then concentrated, and the resultant crude product was purified by medium silica gel column chromatography (chloroform) and then recrystallized from chloroform (2 ml)-methanol (10 ml) to obtain 2.04 g (69%) of free title compound. The thus-obtained compound was isolated as a methanesulfonate.

Reference Examples 9–13

In accordance with the method of Reference Example 8, 17-cyclopropylmethyl-6,7-dehydro-4,5α-epoxy-14β-hydroxy-3-methoxy-6,7,2',3'-(6'-methoxyquinolino)morphinan 3, 17-cyclopropylmethyl-6,7-dehydro-4,5α-epoxy-14β-hydroxy-3-methoxy-6,7,2',3'-(8'-phenylquinolino)morphinan 4, 17-cyclopropylmethyl-6,7-dehydro-4,5α-epoxy-14β-hydroxy-3-methoxy-6,7,2',3'-(7',8'-cyclohexenoquinolino)morphinan 5, 17-cyclopropylmethyl-6,7-dehydro-4,5α-epoxy-14β-hydroxy-3-methoxy-6,7,2',3'-(6'-methylquinolino)morphinan 6, and 17-cyclopropylmethyl-6,7-dehydro-4,5α-epoxy-14β-hydroxy-3-methoxy-6,7,2',3'-[6'-(dimethylamino)quinolino]morphinan 7 were used in place of 17-cyclopropylmethyl-6,7-dehydro-4,5α-epoxy-14β-hydroxy-3-methoxy-6,7,2',3'-(7',8'-benzoquinolino)morphinan 2 to obtain 17-cyclopropylmethyl-6,7-dehydro-4,5α-epoxy-3,14β-dihydroxy-6,7,2',3'-(6'-methoxyquinolino)morphinan 37, 17-cyclopropylmethyl-6,7-dehydro-4,5α-epoxy-3,14β-dihydroxy-6,7,2',3'-(8'-phenylquinolino)morphinan 38, 17-cyclopropylmethyl-6,7-dehydro-4,5α-epoxy-3,14β-dihydroxy-6,7,2',3'-(7',8'-cyclohexenoquinolino)morphinan 39, 17-cyclopropylmethyl-6,7-dehydro-4,5α-epoxy-3,14β-dihydroxy-6,7,2',3'-(6'-methylquinolino)morphinan 40, and 17-cyclopropylmethyl-6,7-dehydro-4,5α-epoxy-3,14β-dihydroxy-6,7,2',3'-[6'-(dimethylamino)quinolino]morphinan 41, respectively.

Examples 29–33

In accordance with the method of Reference Example 8, 17-acetyl-6,7-dehydro-4,5α-epoxy-14β-hydroxy-3-methoxy-6,7,2',3'-(4'-aminoquinolino)morphinan 24, 17-methyl-6,7-dehydro-4,5α-epoxy-14β-hydroxy-3- methoxy-6,7,2',3'-(4'-aminoquinolino)morphinan 23, 17-cyclopropylmethyl-6,7-dehydro-4,5α-epoxy-14β-hydroxy-3-methoxy-6,7,2',3'-(6',6"-ethano-7',8'-benzoquinolino)morphinan 8, 17-cyclopropylmethyl-6,7-dehydro-4,5α-epoxy-14β-hydroxy-3-methoxy-6,7,2',3'-(7',8',3",2"-indenoquinolino)morphinan 9, and 17-cyclopropylmethyl-6,7-dehydro-4,5α-epoxy-14β-hydroxy-3-methoxy-6,7,2',3'-(6'-methoxyquinolino) morphinan 3 were used in place of 17-cyclopropylmethyl-6,7-dehydro-4,5α-epoxy-14β-hydroxy-3-methoxy-6,7,2',3'-(7',8'-benzoquinolino)morphinan 2 to obtain 17-acetyl-6,7-dehydro-4,5α-epoxy-3,14β-dihydroxy-6,7,2',3'-(4'-aminoquinolino)morphinan 42, 17-methyl-6,7-dehydro-4,5α-epoxy-3,14β-dihydroxy-6,7,2',3'-(4'-aminoquinolino) morphinan 43, 17-cyclopropylmethyl-6,7-dehydro-4,5α-epoxy-3,14β-dihydroxy-6,7,2',3'-(6',6"-ethano-7',8'-benzoquinolino)morphinan 44, 17-cyclopropylmethyl-6,7-dehydro-4,5α-epoxy-3,14β-dihydroxy-6,7,2',3'-(7',8',3",2"-indenoquinolino)morphinan 45, and 17-cyclopropylmethyl-6,7-dehydro-4,5α-epoxy-3,14β-dihydroxy-6,7,2',3'-(6'-hydroxyquinolino)morphinan 46, respectively.

Example 34

17-cyclopropylmethyl-6,7-dehydro-4,5α-epoxy-3,14β-dihydroxy- 6,7,2',3'-[4',5'-[N-methylimino(oxomethano)] quinolino]morphinan 47.methanesulfonate 400 mg of 17-cyclopropylmethyl-6,7-dehydro-4,5α-epoxy-3,14β-dihydroxy-6,7,2',3'-[4',5'-[imino (oxomethano)]quinolino]morphinan 34.hydrochloride was dissolved in 10 ml of DMF, and 255 mg (3.75 mmol) of imidazole and 346 mg (2.25 mmol) of t-butyltrimethylsilyl chloride were added to the resultant solution, followed by reaction at room temperature for 2 hours. After the solvent was distilled off under reduced pressure, water was added to the residue, followed by extraction with ether. The organic layers were washed with saturated salt water, dried over anhydrous sodium sulfate, and then concentrated to obtain 427 mg of 3-t-butyltrimethylsiloxy-17-cyclopropylmethyl-6,7-dehydro-4,5α-epoxy-14β-hydroxy-6,7,2',3'-[4',5'-[imino(oxomethano)]quinolino]morphinan.

427 mg of 3-t-butyltrimethylsiloxy-17-cyclopropylmethyl-6,7-dehydro-4,5α-epoxy-14β-hydroxy-6,7,2',3'-[4',5'-[imino(oxomethano)]quinolino]morphinan was dissolved in 15 ml of DMF, and 400 mg (2.9 mmol) of potassium carbonate and 180 μl (2.9 mmol) of methyl iodide were added to the resultant solution, followed by reaction at room temperature for 15 hours. Potassium carbonate was filtered off, and the filtrate was concentrated under reduced pressure. To the residue was added water, and the mixture was extracted with ethyl acetate. The organic layers were washed with saturated brine, dried over anhydrous sodium sulfate, and then concentrated. The thus-obtained crude product was purified by silica gel column chromatography (chloroform:methanol=45:1→30:1) to obtain 348 mg (80% total yield of two steps) of 3-t-butyltrimethylsiloxy-17-cyclopropylmethyl-6,7-dehydro-4,5α-epoxy-14β-hydroxy-6,7,2',3'-[4',5'-[N-methylimino(oxomethano)]quinolino] morphinan.

348 mg (0.57 mmol) of 3-t-butyltrimethylsiloxy-17-cyclopropylmethyl-6,7-dehydro-4,5α-epoxy-14β-hydroxy-6,7,2',3'-[4',5'-[N-methylimino(oxomethano)]quinolino] morphinan was dissolved in 10 ml of THF, and 0.7 ml (0.7 mmol) of tetrabutylammonium fluoride (1M in THF) was added to the resultant solution, followed by reaction at room temperature for 5 minutes. The reaction solution was purified by silica gel column chromatography (chloroform:methanol=200:1→100:1) to obtain 266 mg (yield 96%) of title compound. The thus-obtained compound was isolated as a methanesulfonate.

Example 35

17-cyclopropylmethyl-6,7-dehydro-4,5α-epoxy-14β-hydroxy-3-methoxy-6,7,2',3'-(4'-hydroxyquinolino) morphinan 48

710.8 mg (1.56 mmol) of 17-cyclopropylmethyl-6,7-dehydro-4,5α-epoxy-3,14β-dihydroxy-6,7,2',3'-(4'-aminoquinolino)morphinan 10 was dissolved in methanol, and a hydrogen chloride/methanol solution was added to acidify the resultant solution, followed by concentration to form a hydrochloride. The hydrochloride was dissolved in a mixed solvent of 1.5 ml of acetic acid and 10 ml of 20% aqueous sulfuric acid solution, and the resultant solution was then cooled to 0° C. To the solution was added dropwise 1 ml of an aqueous solution of 140.3 mg (2.03 mmol) of sodium nitrite, and the resultant mixture was stirred at 0° C. for 1.5 hours as it was, and then heated under reflux for 1.5 hours. The reaction solution was allowed to cool, concentrated to a volume of about ½, and then made basic by adding about 42 ml of a 2N aqueous sodium hydroxide solution. After extraction with chloroform-ammonia-saturated chloroform-methanol (2:2:1) (30 ml+10 ml×2), the organic layers were together dried over anhydrous sodium sulfate, and then concentrated. 611 mg of the thus-obtained crude product was purified by silica gel column chromatography (chloroform:methanol=30:1→15:1) to obtain 359.8 mg (yield 51%) of title compound.

Examples 36–37

In accordance with the method of Reference Example 8, 17-cyclopropylmethyl-6,7-dehydro-4,5α-epoxy-14β-hydroxy- 3-methoxy-6,7,2',3'-(4'-hydroxyquinolino) morphinan 48 and 17-cyclopropylmethyl-6,7-dehydro-4,5α-epoxy-3,14β-dihydroxy-6,7,2',3'-(4'-amino-6'-methoxyquinolino)morphinan 21 were used in place of 17-cyclopropylmethyl-6,7-dehydro-4,5α-epoxy-14β-hydroxy-3-methoxy-6,7,2',3'-(7',8'-benzoquinolino) morphinan 2 to obtain 17-cyclopropylmethyl-6,7-dehydro-4,5α-epoxy-3,14β-dihydroxy-6,7,2',3'-(4'-hydroxyquinolino)morphinan 49 and 17-cyclopropylmethyl-6,7-dehydro-4,5α-epoxy-3,14β-dihydroxy-6,7,2',3'-(4'-amino-6'-hydroxyquinolino) morphinan 50, respectively.

Examples 38–40

In accordance with the method of Example 19, 2'-amino-3'-hydroxyacetophenone, 1-(2'-aminophenyl)-2-methyl-1-propanone, and 1-(2'-aminophenyl)-1-propanone were used in place of 2'-aminoacetophenone to obtain 17-cyclopropylmethyl-6,7-dehydro-4,5α-epoxy-3,14β-dihydroxy-6,7,2',3'-(4'-methyl-8'-hydroxyquinolino) morphinan 51, 17-cyclopropylmethyl-6,7-dehydro-4,5α-epoxy-3,14β-dihydroxy-6,7,2',3'-(4'-isopropylquinolino) morphinan 52, and 17-cyclopropylmethyl-6,7-dehydro-4,5α-epoxy-3,14β-dihydroxy-6,7,2',3'-(4'-ethylquinolino) morphinan 53, respectively.

Example 41

17-cyclopropylmethyl-6,7-dehydro-4,5α-epoxy-3,14β-dihydroxy-6,7,2',3'-(4'-aminocarbonylquinolino)morphinan 54.methanesulfonate Oxalyl chloride (0.12 ml, 1.38 mmol), DMF (2 droplets) and 210 mg (0.45 mmol) of 17-cyclopropylmethyl-6,7-dehydro-4,5α-epoxy-3,14β-dihydroxy-6,7,2',3'-(4'-carboxyquinolino)morphinan 30 were added to methylene chloride (10 ml), followed by stirring at room temperature in a nitrogen atmosphere for 22 hours. After concentration, water (5 ml), 28% ammonia water (10 ml) and chloroform (10 ml) were added to the residue, followed by stirring for 16 hours. To the solution was added water (50 ml), and the resultant mixture was extracted with chloroform (50 ml×2). The organic layers were together dried over anhydrous sodium sulfate, and then concentrated. The thus-obtained product was purified by medium pressure silica gel column chromatography (chloroform:methanol=40:1→20:1), and methanesulfonic acid was added to the product, followed by purification by a Sephadex column to obtain 88 mg (42%) of title compound as a methanesulfonate.

Example 42

17-cyclopropylmethyl-6,7-dehydro-4,5α-epoxy-3,14β-dihydroxy-6,7,2',3'-[4'-(benzylamino)quinolino]morphinan 55.methanesulfonate 203 mg (0.46 mmol) of 17-cyclopropylmethyl-6,7-dehydro-4,5α-epoxy-3,14β-dihydroxy-6,7,2',3'-(4'-aminoquinolino)morphinan 10 was dissolved in THF, and benzaldehyde (94 μl, 0.92 mmol), piperidine (91 μl, 0.92 mmol) and toluene (10 ml) were added to the resultant solution, followed by heating under reflux for 5 hours, with the water separator provided. After the reaction solution was cooled, the solution was concentrated, and an aqueous saturated sodium hydrogencarbonate solution (50 ml) was added to the residue, followed by extraction with chloroform (50 ml×2). The organic layers were together dried over anhydrous sodium sulfate, and then concentrated. The resultant residue was purified by medium pressure silica gel column chromatography (chloroform:methanol=100:1→20:1) to obtain 93 mg of imine intermediate. The thus-obtained imine intermediate (93 mg, 0.18 mmol) was dissolved in THF, and lithium borohydride (19 mg, 0.88 mmol) was added to the resultant solution, followed by heating under reflux in a nitrogen atmosphere for 3 hours. To the solution was further added lithium borohydride (20 mg, 0.91 mmol), and the resultant mixture was heated under reflux for 5 hours. The reaction solution was cooled, and a saturated aqueous sodium hydrogencarbonate solution (50 ml) was added to the solution, followed by extraction with chloroform (50 ml×2). The organic layers were together dried over anhydrous sodium sulfate and then concentrated. The residue was purified by medium pressure silica gel column chromatography (chloroform→chloroform:methanol=50:1) to obtain 57 mg (23%) of title compound. The compound was isolated as a methanesulfonate.

Example 43

In accordance with the method of Example 42, cyclohexanecarboaldehyde was used in place of benzaldehyde to obtain 17-cyclopropylmethyl-6,7-dehydro-4,5α-epoxy-3,14β-dihydroxy-6,7,2',3'-[4'-(cyclohexylamino)quinolino]morphinan 56.

Example 44

6,7-dehydro-4,5α-epoxy-3,14β-dihydroxy-6,7,2',3'-(4'-aminoquinolino)morphinan 57.hydrochloride To 0.93 g (2.16 mmol) of 17-acetyl-6,7-dehydro-4,5α-epoxy-3,14β-dihydroxy-6,7,2',3'-(4'-aminoquinolino)morphinan 41 was added 80 ml of 6N hydrochloric acid in an argon atmosphere, and 80 ml of methanol was further added to the resultant mixture to form a solution, followed by heating under reflux for 15.5 hours. The solution was allowed to cool and then concentrated. The resultant crude product was purified by a Sephadex column (methanol) to obtain 529 mg (53%) of title compound.

Example 45

In accordance with the method of Example 27, a DMF-benzene mixed solvent was used in place of acetic acid, and methanesulfonic acid was used in place of scandium triflate to obtain 17-cyclopropylmethyl-6,7-dehydro-4,5α-epoxy-3,14β-dihydroxy-6,7,2',3'-[4',5'-[imino(iminomethano)]quinolino]morphinan 58.

The structural formulae, acid addition salts, production yields, and various spectral data of the compounds of the above reference examples and examples of the present invention are shown in the table below.

| Compound | NMR | Data |
| --- | --- | --- |
| Compound 1<br>Methanesulfonate<br>Yield: 78 (%)<br>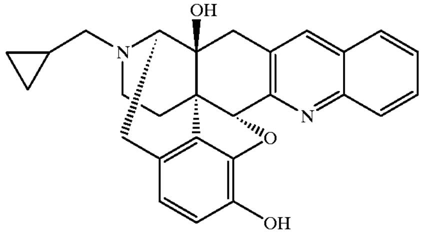 | NMR (ppm) (400 MHz, $CDCl_3$)<br>0.14–0.20 (2H, m). 0.53–0.62 (2H, m), 0.90 (1H, m), 1.83–1.91 (1H, m), 1.94 (2H, br s), 2.36–2.50 (4H, m), 2.68–2.77 (2H, m), 2.80 (1H, d, J=16.1 Hz), 2.87–2.91 (1H, m), 3.19 (1H, d, J=18.6 Hz), 3.34 (1H, d, J=6.8 Hz), 5.68 (1H, s), 6.59 (1H, d, J=8.1 Hz), 6.67 (1H, d, J=8.1 Hz), 7.45–7.50 (1H, m), 7.60–7.64 (1H, m), 7.69 (1H, d, J=7.8 Hz), 7.82 (1H, s), 8.08 (1H, d, J=8.8 Hz) | Melting Point 209 (dec) (° C.).<br>Elemental Analysis<br>as $C_{27}H_{26}N_2O_2 \cdot 2.0CH_3SO_3.1.7\ H_2O$<br>Calculated: C. 53.64; H, 5.81; N. 4.31; S, 9.88.<br>Found: C, 53.51; H, 5.84; N, 4.12; S, 10.22<br>IR($cm^{-1}$) (not measured)<br>Mass (EI) 426 ($M^-$) (data of salt-free compound) |
| Compound 2<br>Methanesulfonate<br>Yield 80 (%)<br>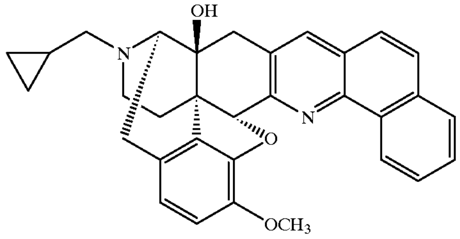 | NMR (ppm) (300 MHz, DMSO-$d_6$)<br>0.42–0.57 (2H, m), 0.61–0.80 (2H, m), 1.12 (1H, m), 1.94 (1H, m), 2.30 (3H, s), 2.64–2.89 (3H, m), 2.96 (1H, m), 3.08 (1H, d, J=17.0 Hz), 3.14–3.32 (2H, m), 3.36–3.43 (1H, m), 3.54–3.62 (1H, m), 3.66 (3H, s), 4.14 (1H, d, J=6.0 Hz), 5.87 (1H, s), 6.51 (1H, s), 6.79 (1H, d, J=8.3 Hz), 6.86 (1H, d, J=8.3 Hz), 7.75–7.85 (3H, m), 7.96 (1H, d, J=8.8 Hz), 8.05(1H, m), 8.16 (1H, s), 9.05 (1H, br s), 9.21 (1H, m). | Melting Point 207–213 (dec). (° C.).<br>Elemental Analysis<br>as $C_{32}H_{30}N_2O_3.CH_3SO_3H.0.4\ H_2O$<br>Calculated: C, 66.74; H, 5.91; N, 4.72; S, 5.40<br>Found: C, 66.52; H, 6.07; N, 4.80; S, 5.47<br>IR($cm^{-1}$) (KBr)<br>3400, 1638, 1508, 1454, 1408, 1288, 1265, 1209, 1125, 1048, 905, 814, 775, 553, 526.<br>Mass (FAB) 491 ($(M+H)^+$). |
| Compound 3<br>Methanesulfonate<br>Yield 49 (%)<br>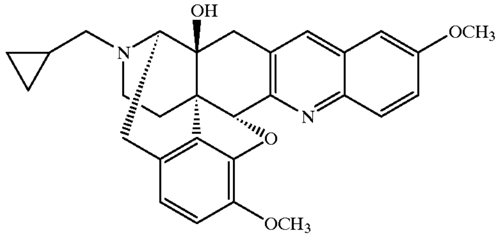 | NMR (ppm) (300 MHz, DMSO-$d_6$)<br>0.41–0.55 (2H, m), 0.60–0.79 (2H, m), 1.10 (1H, m), 1.88 (1H, d, J = 11.8 Hz), 2.30 (3.3H, s), 2.56–2.86 (2H, m), 2.77 (1H, d, J=16.5 Hz), 2.92–3.20 (1H, m), 3.01 (1H, d, J=16.8 Hz), 3.11–3.30 (2H, m), 3.36–3.49 (1H, m), 3.50 (1H, d, J=20.0 Hz), 6.45 (1H, br s), 6.77 (1H, d, J = 8.3 Hz), 6.85 (1H, d, J = 8.3 Hz), 7.32 (1H, d, J = 2.7 Hz), 7.40–7.44 (1H, m), 7.96 (1H, d, J = 9.3 Hz), 7.98 (1H, s), 9.01 (1H, br s). | Melting Point 195–207 (dec). (° C.).<br>Elemental Analysis<br>as $C_{29}H_{30}N_2O_4.1.1\ CH_3SO_3H.0.5\ H_2O$<br>Calculated: C, 61.77; H, 6.10; N, 4.79; S, 6.03.<br>Found: C, 61.65; H, 6.29; N, 4.74; S, 6.11.<br>IR($cm^{-1}$) (KBr)<br>3400, 1626, 1499, 1458, 1388, 1210, 1195, 1052, 899, 785, 561, 536.<br>Mass (EI) 470 ($M^+$) (data of salt-free compound) |
| Compound 4<br>Yield: 58 (%) | NMR (ppm) (300 MH'2, $CDCl_3$)<br>0.13–0.20 (2H, m), 0.50–0.60 (2H, m), 0.82–0.98 (1H, m), | Mass (EI) 516 ($M^+$) |

-continued

| | | |
|---|---|---|
| 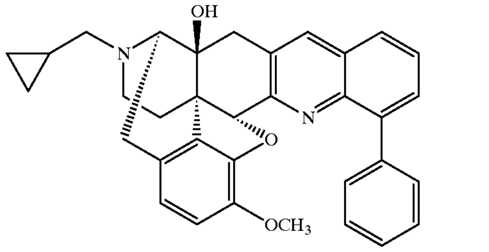 | 1.80–1.85 (1H, m), 2.35–2.50 (4H, m), 2.67–2.91 (4H, m), 3.21 (1H, d, J=18.0 Hz), 3.30–3.40 (1H, m), 3.81 (3H, s), 5.67 (1H, s), 6.61 (1H, d, J=8.7 Hz), 6.67 (1H, d, J=8.7 Hz), 7.38–7.43 (1H, m), 7.48–7.55 (3H, m), 7.66–7.74 (2H, m), 7.82–7.90 (3H, m). | |
| Compound 5<br>Yield: 39 (%) | NMR (ppm) (300 MHz, $CDCl_3$)<br>0.13–0.20 (2H, m), 0.53–0.60 (2H, m), 0.90 (1H, m), 1.82–1.98 (5H, m), 2.38–2.51 (4H, m), 2.67–2.76 (3H, m), 2.85–2.92 (3H, m) 3.20 (1H, d, J=18.7 Hz), 3.26–3.38 (2H, m), 3.42–3.55 (1H, m), 3.78 (3H, s), 4.91 (1H, br s), 5.72 (1H, s), 6.61 (1H, d, J=8.1 Hz) 6.66 (1H, d, J=8.1 Hz), 7.17 (1H, d, J=8.5 Hz), 7.41 (1H, d, J=8.2 Hz), 7.70 (1H, s). | Mass (EI) 494 ($M^+$) |
| 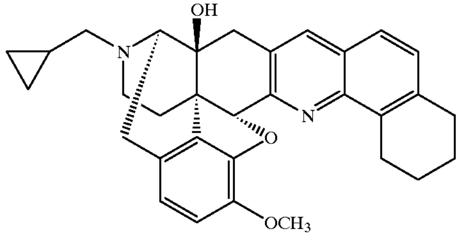 | | |
| Compound 6<br>Yield: 58 (%) | NMR (ppm) (300 MHz, $CDCl_3$)<br>0.13–0.20 (2H, m), 0.53–0.61 (2H, m), 0.82–0.94 (1H, m), 1.80–1.90 (1H, m), 2.37–2.50 (4H, m), 2.49 (3H, s), 2.66–2.90 (4H, m), 3.20 (1H, d, J=18.6 Hz), 3.33 (1H, d, J=6.5 Hz), 3.78 (3H, s), 5.69 (1H, s), 6.61 (1H, d, J=8.1 Hz), 6.66 (1H, d, J=8.1 Hz), 7.43 (1H, s), 7.45 (1H, d, J=8.7 Hz), 7.70 (1H, s), 8.03 (1H d J=8.7 Hz). | Mass (EI) 454 ($M^+$)<br>Mass (EI) 454 ($M^+$) |
| 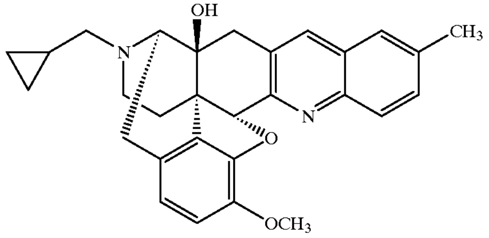 | | |
| Compound 7<br>Yield 20 (%) | NMR (ppm) (300 MHz, $CDCl_3$)<br>0.16–0.20 (2H, m), 0.55–0.60 (2H, m), 0.80–0.95 (1H, m), | Mass (EI) 483 ($M^+$) |

-continued

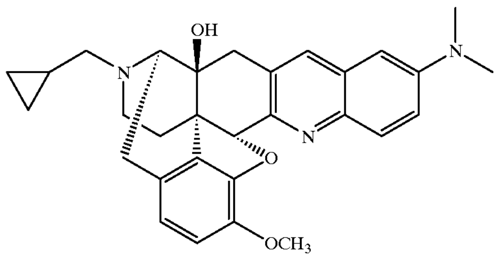

1.82–1.86 (1H, m), 2.39–2.48 (4H, m), 2.65–2.90 (4H, m), 3.05 (6H, s), 3.19 (1H, d, J=18.9 Hz), 3.30–3.38 (1H, m), 3.79 (3H, s), 5.67 (1H, s), 6.46–6.68 (3H, m), 7.30 (1H, dd, J=9.3, 2.7 Hz), 7.58 (1H, s), 7.99 (1H, d, J=9.3 Hz).

Compound 8
Methanesulfonate
Yield: 83 (%)

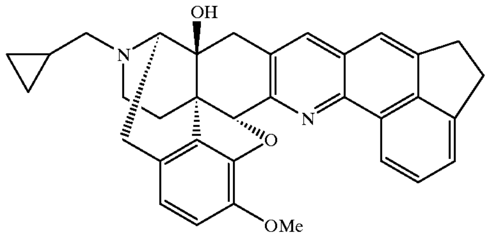

NMR (ppm) (300 MHz, DMSO-$d_6$)
0.42–0.57 (2H, m), 0.59–0.79 (2H, m), 1.12 (1H, m), 1.92 (1H, d, J = 12.1 Hz), 2.30 (3H, s), 2.62–2.90 (2H, m), 2.85 (1H, d, J=17.0 Hz), 2.92–3.05 (1H, m), 3.04 (1H, d, J=16.8 Hz), 3.13–3.35 (2H, m), 3.35–3.51 (5H, m), 3.57 (1H, d, J=20.3 Hz), 3.66 (3H, s), 4.12 (1H, d, J=.3 Hz), 5.85 (1H, s), 6.50 (1H, br s), 6.78 (1H, d, J=8.3 Hz), 6.85 (1H, d, J=8.3 Hz), 7.57 (1H, s), 7.64 (1H, d, J=6.9 Hz), 7.73–7.78 (1H, m), 8.07 (1H, s), 8.65 (1H, d, J=7.7 Hz), 9.04 (1H, br s).

Melting Point >220 (dec). (° C.).
Elemental Analysis
as $C_{34}H_{32}N_2O_3.CH_3SO_3H.0.7\ H_2O$
Calculated: C, 67.22; H, 6.03; N, 4.48; S, 5.13.
Found: C, 67.08; H, 5.94; N, 4.57; S, 5.42.
IR($cm^{-1}$) (KBr)
3400, 1630, 1508, 1454, 1423, 1332, 1288, 1207, 1123, 1050, 901, 779, 553.
Mass (FAB) 517 ($(M+H)^+$).

Compound 9
Yield 66 (%)

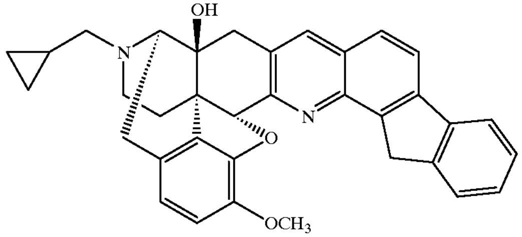

NMR (ppm) (300 MHz, $CDCl_3$)
0.15–0.21 (2H, m), 0.56–0.62 (2H, m), 0.83–0.95 (1H, m), 1.87–1.94 (1H, m), 2.35–2.50 (4H, m), 2.67–2.94 (4H, m), 3.22 (1H, d, J=18.6 Hz), 3.36 (1H, d, J=6.6 Hz), 3.79 (3H, s), 4.39 (1H, d, J=22.9 Hz), 4.50 (1H, d, J=22.9 Hz), 5.77 (1H, s), 6.63 7.67–7.74 (2H, m), 7.80–7.88 (2H, m), 7.91 (1H, d, J=8.1 Hz).

Mass (EI) 528 ($M^+$)
Mass (EI) 528 ($M^+$)

Compound 10
Hydrochloride
Yield: 38 (%)

NMR (ppm) (300 MHz, DMSO-$d_6$)
0.42–0.53 (2H, m), 0.61–0.75 (2H, m), 1.14 (1H, m), 1.89 (1H, d, J = 11.8 Hz), 2.34 (1H, d, J = 16.5 Hz), 2.65–2.80 (2H, m), Melting Point >240 (° C.).
Elemental Analysis
as $C_{27}H_{27}N_3O_3.1.9\ HCl.1.0\ H_2O$ -continued

| | | |
|---|---|---|
| 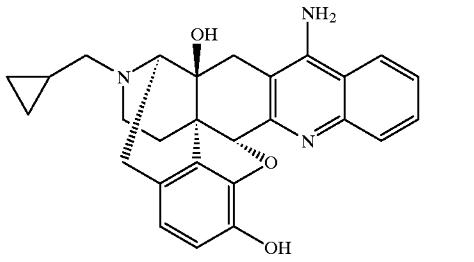 | 3.04–3.22 (4H, m), 3.31–3.40 (1H, m), 3.58 (1H, d, J=20.0 Hz), 4.17 (1H, d, J=5.8 Hz), 5.88 (1H, s), 6.71 (1H, d, J=8.2 Hz), 6.76 (1H, d, J=8.2 Hz), 7.01 (1H, br s), 7.65 (1H, m), 7.96 (1H, m), 8.07 (1H, d, J=8.2 Hz), 8.43 (1H, br s), 8.50 (1H, d, J=8.5 Hz), 9.24 (2H, m), 9.62 (1H, br s), 14.49 (1H, br s) | Calculated: C, 61.32; H, 5.89; N, 7.95; Cl, 12.74.<br>Found: C, 61.54; H, 5.86; N, 7.67; Cl, 12.79.<br>IR(Cm$^{-1}$) (KBr)<br>3400, 3200, 1650, 1595, 1502, 1460, 1433, 1379, 1323, 1251, 808, 764.<br>Mass (FAB) 442 ((M+H)$^+$) |
| Compound 11<br>Hydrochloride<br>Yield: 40(%)<br>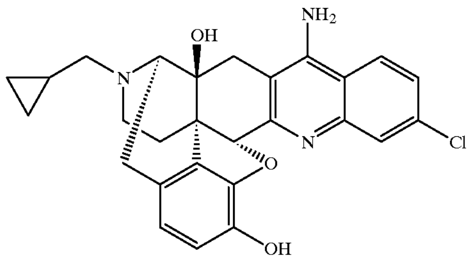 | NMR (ppm) (300 MHz, DMSO-$d_6$)<br>0.40–0.54(2H, m), 0.60–0.77(2H, m), 1.10(1H, m), 1.87(1H, m), 2.31(1H, d, J=16.8 Hz), 2.43–2.81(3H, m), 2.96(1H, d, J=17.3 Hz), 3.02–3.06(1H, m), 3.14–3.20(2H, m), 3.33–3.39 (1H, m), 3.58(1H, d J=20.0 Hz), 4.16(1H, d, J=6.6 Hz), 5.79 (1H, s), 6.69–6.77(2H, m), 7.08(1H, br, s), 7.69–7.72(1H, m), 8.03(1H, s), 8.44–8.68(1H, br s), 8.48(1H, d, J=8.8 Hz), 9.25 (1H, br s), 9.49(1H, br s), 9.63(1H, s), 14.67(1H, br s). | Melting Point >220 (dec) (° C.).<br>Elemental Analysis<br>as $C_{27}H_{28}ClN_3O_3.2HCl.0.3H_2O$<br>Calculated: C, 58.51; H, 5.20; Cl, 19.19; N, 7.58.<br>Found: C, 58.45; H, 5.30; Cl, 19.27; N, 7.50.<br>IR(cm$^{-1}$) (KBr)<br>3400, 3180, 1636, 1605, 1497, 1468, 1431, 1379, 1247, 1114, 924, 816.<br>Mass (FAB) 476 ((M+H)$^+$). |
| Compound 12<br>Hydrochloride<br>Yield: 33(%)<br>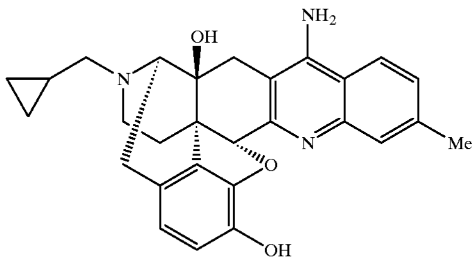 | NMR (ppm) (300 MHz, DMSO-$d_6$)<br>0.40–0.54(2H, m), 0.59–0.75(2H, m), 1.14(1H, m), 1.87(1H, d, J=11.0 Hz), 2.31(1H, d, J=16.8 Hz), 2.53(3H, s), 2.63–2.74 (2H, m), 3.00–3.22(4H, m), 3.34(1H, m), 3.57(1H, d, J=19.5 Hz), 4.17(1H, m), 5.85(1H, s), 6.70(1H, d, J=8.2 Hz), 6.76 (1H, d, J=8.2 Hz), 7.01(1H, br s), 7.49(1H, d, J=8.8 Hz), 7.82 (1H, s), 8.35(1H, br s), 8.39(1H, d, J=8.8 Hz), 9.26(2H, br s), 9.63(1H, s), 14.38(1H, br s). | Melting Point >240 (dec) (° C.).<br>Elemental Analysis<br>as $C_{28}H_{29}N_3O_3.1.9HCl.0.4H_2O$<br>Calculated: C, 63.21; H, 6.01; N, 7.90; Cl, 12.66.<br>Found: C, 63.09; H, 6.11; N, 7.96; Cl, 12.71.<br>IR(cm$^{-1}$) (KBr)<br>3400, 3200, 1642, 1599, 1504, 1468, 1431, 1380, 1319, 1249, 816, 748.<br>Mass (FAB) 456 ((M+H)$^+$). |
| Compound 13<br>Hydrochloride<br>Yield: 28(%) | NMR (ppm) (400 MHz, DMSO-$d_6$)<br>0.48(m, 2H), 0.65(m, 1H), 0.72(m, 1H), 1.14(m, 1H), 1.89 (br d, 1H, J=12.2 Hz), 2.40(d, 1H, J=17.1 Hz), 2.68(m, 1H), | Melting Point >250 (° C.)<br>Elemental Analysis<br>as $C_{27}H_{26}ClN_3O_3.2HCl.1.8H_2O$ |

-continued

| | | |
|---|---|---|
| 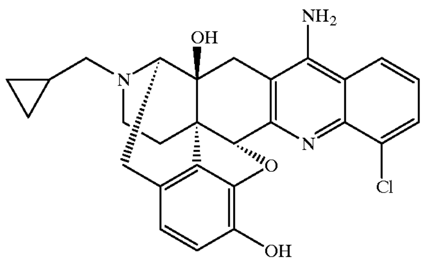 | 2.78(m, 1H), 2.98(d, 1H, J=17.1 Hz), 3.06–2.23(m, 3H), 3.58 (d, 1H, J=20.0 Hz), 4.19(d, 1H, J=6.8 Hz), 5.87(s, 1H), 6.73 (d, 1H, J=8.3 Hz), 6.76(d, 1H, J=8.3 Hz), 7.04(br s, 1H, OH), 7.74(br d, 1H, J=7.3 Hz), 7.88(br t, 1H, J=7.8 Hz), 8.08 (br d, 1H, J=8.3 Hz), 8.57(br s, 1H, NH), 8.81(br s, 1H, NH), 9.23 (br s, 1H, $NH^+$), 9.63(br s, 1H, OH), 14.72(br s, 1H, $NH^+$). | Calculated: C, 55.79; H, 5.61; Cl, 18.30; N, 7.23.<br>Found: C, 55.87; H, 5.61; Cl, 18.00; N, 7.07.<br>IR($cm^{-1}$) (KBr)<br>3392, 1630, 1595, 1545, 1493, 1460, 1402, 1323, 1276, 1249, 1178, 1116, 1052, 1031, 940, 806.<br>Mass (FAB) 461 ($(M+H)^+$). |
| Compound 14<br>Hydrochloride<br>Yield: 22(%)<br>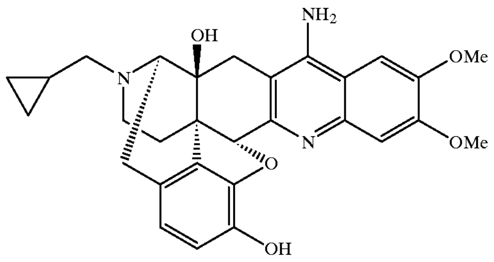 | NMR (ppm) (300 MHz, DMSO-$d_6$)<br>0.46(2H, m), 0.58–0.78(2H, m), 1.09(1H, m), 1.80–1.90 (1H, m), 2.29(1H, d, J=16.8 Hz), 2.54–3.42(7H, m), 3.44–62 (1H, m), 3.89(3H, s), 3.95(3H, s), 4.14(1H, m), 5.72(1H, s), 6.70(1H, s), 6.70(1H, s),7.02(1H, br s), 7.33(1H, s), 7.73 (1H, s), 8.05(1H, br s), 8.84(1H, br s), 9.24(1H, br s), 9.59 (1H, br s), 14.21(1H, br s). | Melting Point >230 (dec) (° C.).<br>Elemental Analysis<br>as $C_{29}H_{31}N_3O_3$.1.9HCl.0.7$H_2O$<br>Calculated: C, 59.70; H, 5.93; N, 7.20; Cl, 11.54.<br>Found: C, 59.82; H, 5.85; N, 7.16; Cl, 11.39.<br>IR($cm^{-1}$) (KBr)<br>3400, 3200, 1657, 1605, 1516, 1466, 1439, 1421, 1290, 1247, 1218.<br>Mass (FAB) 502 ($(M+H)^+$). |
| Compound 15<br>Hydrochloride<br>Yield: 37(%)<br>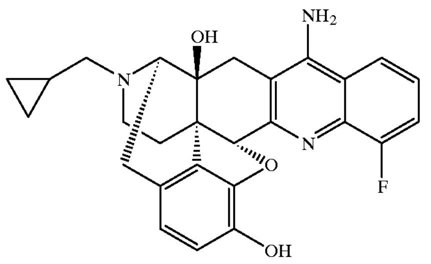 | NMR (ppm) (300 MHz, $CD_3OD$)<br>0.61(m, 2H), 0.85(m, 1H), 0.94(m, 1H), 1.25(m, 1H), 2.07 (m, 1H), 2.54(d, 1H, J=16.7 Hz), 2.86(m, 1H), 3.00(d, 1H, J=16.7 Hz), 3.02–3.15(m, 2H), 3.30–3.44(m, 2H), 3.48(m, 1H), 3.63(d, 1H, J=20.3 Hz), 4.36(d, 1H, J=6.6 Hz), 5.76(s, 1H), 6.77(d, 1H, J=8.2 Hz), 6.83(d, 1H, J=8.2 Hz), 7.38(br dd, 1H, J=13.7, 7.9 Hz), 7.79(br d, 1H, J=7.5 Hz), 7.90(m,1H). | Melting Point >267 (dec) (° C.).<br>Elemental Analysis<br>as $C_{27}H_{28}FN_3O_3$.1.8HCl.0.5$H_2O$<br>Calculated: C, 60.71; H, 5.43; Cl, 11.95; F, 3.56; N, 7.87.<br>Found: C, 60.66; H, 5.52; Cl, 11.85; F, 3.54; N, 7.90.<br>IR($cm^{-1}$) (KBr)<br>3378, 3194, 1642, 1605, 1504, 1466, 1417, 1377,1325, 1280, 1249, 1181, 1118, 1062, 1038, 922, 899, 808.<br>Mass (FAB) 460 ($(M+H)^+$). |
| Compound 16<br>Hydrochloride<br>Yield: 37(%) | NMR (ppm) (600 MHz, $CD_3OD$)<br>0.58 (m, 2H), 0.83(m, 1H), 0.92(m, 1H), 1.22(m, 1H), 2.05 (dd, 1H, J=13.5, 3.1 Hz), 2.54(d, 1H, J=16.5 Hz), 2.85(ddd, | Melting Point 265–280 (dec) (° C.).<br>Elemental Analysis<br>as $C_{27}H_{28}N_4O_6$.1.6HCl.0.6$H_2O$ |

-continued

| | | |
|---|---|---|
| 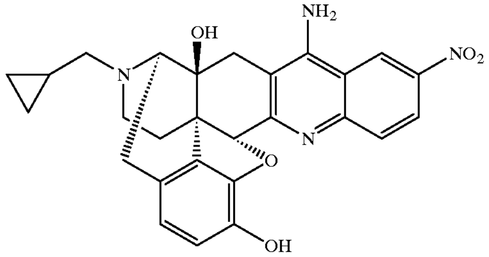 | 1H, J=13.4, 13.4, 4.9 Hz), 3.00(d, 1H, J=16.5 Hz), 3.02–3.11 (m, 2H), 3.28–3.40(m, 2H), 3.48(m, 1H), 3.61(d, 1H, J=19.8 Hz), 4.34(br d, 1H, J=4.6 Hz), 5.74(s, 1H), 6.74(d, 1H, J=8.1 Hz), 6.81(d, 1H, J=8.1 Hz), 8.05(br d, 1H, J=8.5 Hz), 8.54(m, 1H), 9.38(br s, 1H). | Calculated: C, 58.36; H, 5.22; Cl, 10.21; N, 10.08.<br>Found: C, 58.34; H, 5.39; Cl, 10.40; N, 9.86.<br>IR($cm^{-1}$) (KBr)<br>3346, 3174, 1644, 1611, 1506, 1466, 1433, 1381, 1338, 1278, 1178, 1116, 1052, 920, 835, 810, 746.<br>Mass (FAB) 487 ($(M+H)^+$). |
| Compound 17<br>Hydrochloride<br>Yield: 23(%)<br>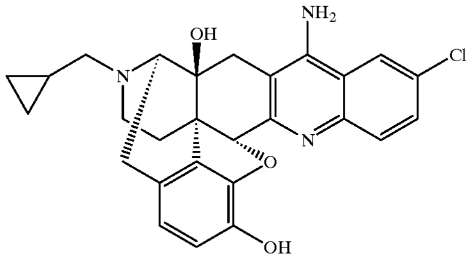 | NMR (ppm) (300 MHz, $CD_3OD$)<br>0.58 (m, 2H), 0.83(m, 1H), 0.92(m, 1H), 1.22(m, 1H), 2.05 (dd, 1H, J=13.5, 3.1 Hz), 2.54(d, 1H, J=16.5 Hz), 2.85(ddd, 1H, J=13.4, 13.4, 4.9 Hz), 3.00(d, 1H, J=16.5 Hz), 3.02–3.11 (m, 2H), 3.28–3.40(m, 2H), 3.48(m, 1H), 3.61(d, 1H, J=19.8 Hz), 4.34(br d, 1H, J=4.6 Hz), 5.74(s, 1H), 6.74(d, 1H, J=8.1 Hz), 6.81(d, 1H, J=8.1 Hz), 8.05(br d, 1H, J=8.5 Hz), 8.54(m, 1H), 9.38(br s, 1H). | Melting Point 220 (° C.).<br>Elemental Analysis<br>as $C_{27}H_{28}N_4O_6$.1.6HCl.0.6$H_2O$<br>Calculated: C, 58.36; H, 5.22; Cl, 10.21; N, 10.08.<br>Found: C, 58.34; H, 5.39; Cl, 10.40; N, 9.86.<br>IR($cm^{-1}$) (KBr)<br>3346, 3174, 1644, 1611, 1506, 1466, 1433, 1381, 1338, 1278, 1178, 1116, 1052, 920, 835, 810, 746.<br>Mass (FAB) 487 ($(M+H)^+$). |
| Compound 18<br>Hydrochloride<br>Yield: 23(%)<br>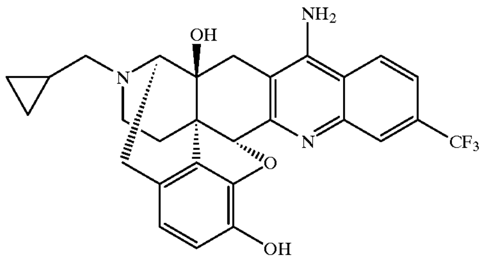 | NMR (ppm) (300 MHz, $CD_3OD$)<br>0.58 (m, 2H), 0.83(m, 1H), 0.92(m, 1H), 1.22(m, 1H), 2.05 (dd, 1H, J=13.5, 3.1 Hz), 2.54(d, 1H, J=16.5 Hz), 2.85(ddd, 1H, J=13.4, 13.4, 4.9 Hz), 3.00(d, 1H, J=16.5 Hz), 3.02–3.11 (m, 2H), 3.28–3.40(m, 2H), 3.48(m, 1H), 3.61(d, 1H, J=19.8 Hz), 4.34(br d, 1H, J=4.6 Hz), 5.74(s, 1H), 6.74(d, 1H, J=8.1 Hz), 6.81(d, 1H, J=8.1 Hz), 8.05(br d, 1H, J=8.5 Hz), 8.54(m, 1H), 9.38(br s, 1H). | Melting Point 230 (° C.).<br>Elemental Analysis<br>as $C_{27}H_{28}N_4O_6$.1.6HCl.0.6$H_2O$<br>Calculated: C, 58.36; H, 5.22; Cl, 10.21; N, 10.08.<br>Found: C, 58.34; H, 5.39; Cl, 10.40; N, 9.86.<br>IR($cm^{-1}$) (KBr)<br>3346, 3174, 1644, 1611, 1506, 1466, 1433, 1381, 1338, 1278, 1178, 1116, 1052, 920, 835, 810, 746.<br>Mass (FAB) 487 ($(M+H)^+$). |
| Compound 19<br>Methanesulfonate<br>Yield: 54(%) | NMR (ppm) (300 MHz, DMSO-$d_6$)<br>0.58 (m, 2H), 0.83(m, 1H), 0.92(m, 1H), 1.22(m, 1H), 2.05 (dd, 1H, J=13.5, 3.1 Hz), 2.54(d, 1H, J=16.5 Hz), 2.85(ddd, | Melting Point >220 (dec) (° C.).<br>Elemental Analysis<br>as $C_{27}H_{28}N_4O_6$.1.6HCl.0.6$H_2O$ |

-continued

| | | |
|---|---|---|
| 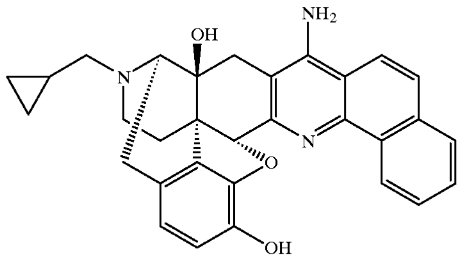 | 1H, J=13.4, 13.4, 4.9 Hz), 3.00(d, 1H, J=16.5 Hz), 3.02–3.11 (m, 2H), 3.28–3.40(m, 2H), 3.48(m, 1H), 3.61(d, 1H, J=19.8 Hz), 4.34(br d, 1H, J=4.6 Hz), 5.74(s, 1H), 6.74(d, 1H, J=8.1 Hz), 6.81(d, 1H, J=8.1 Hz), 8.05(br d, 1H, J=8.5 Hz), 8.54(m, 1H), 9.38(br s, 1H). | Calculated: C, 58.36; H, 5.22; Cl, 10.21; N, 10.08.<br>Found: C, 58.34; H, 5.39; Cl, 10.40; N, 9.86.<br>IR($cm^{-1}$) (KBr)<br>3346, 3174, 1644, 1611, 1506, 1466, 1433, 1381, 1338, 1278, 1178, 1116, 1052, 920, 835, 810, 746.<br>Mass (FAB) 487 ($(M+H)^+$). |
| Compound 20<br>Methanesulfonate<br>Yield: 29(%)<br>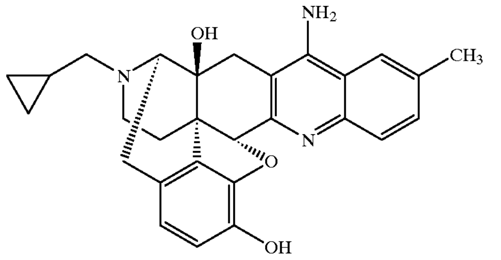 | NMR (ppm) (400 MHz, $CD_3OD$)<br>0.58 (m, 2H), 0.83(m, 1H), 0.92(m, 1H), 1.22(m, 1H), 2.05 (dd, 1H, J=13.5, 3.1 Hz), 2.54(d, 1H, J=16.5 Hz), 2.85(ddd, 1H, J=13.4, 13.4, 4.9 Hz), 3.00(d, 1H, J=16.5 Hz), 3.02–3.11 (m, 2H), 3.28–3.40(m, 2H), 3.48(m, 1H), 3.61(d, 1H, J=19.8 Hz), 4.34(br d, 1H, J=4.6 Hz), 5.74(s, 1H), 6.74(d, 1H, J=8.1 Hz), 6.81(d, 1H, J=8.1 Hz), 8.05(br d, 1H, J=8.5 Hz), 8.54(m, 1H), 9.38(br s, 1H). | Melting Point 215 (° C.).<br>Elemental Analysis<br>as $C_{27}H_{28}N_4O_6$.1.6HCl.0.6$H_2O$<br>Calculated: C, 58.36; H, 5.22; Cl, 10.21; N, 10.08.<br>Found: C, 58.34; H, 5.39; Cl, 10.40; N, 9.86.<br>IR($cm^{-1}$) (KBr)<br>3346, 3174, 1644, 1611, 1506, 1466, 1433, 1381, 1338, 1278, 1178, 1116, 1052, 920, 835, 810, 746.<br>Mass (FAB) 487 ($(M+H)^+$). |
| Compound 21<br>Hydrochloride<br>Yield: 18(%)<br>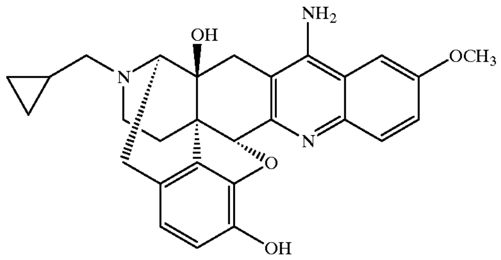 | NMR (ppm) (300 MHz, $CD_3OD$)<br>0.58 (m, 2H), 0.83(m, 1H), 0.92(m, 1H), 1.22(m, 1H), 2.05 (dd, 1H, J=13.5, 3.1 Hz), 2.54(d, 1H, J=16.5 Hz), 2.85(ddd, 1H, J=13.4, 13.4, 4.9 Hz), 3.00(d, 1H, J=16.5 Hz), 3.02–3.11 (m, 2H), 3.28–3.40(m, 2H), 3.48(m, 1H), 3.61(d, 1H, J=19.8 Hz), 4.34(br d, 1H, J=4.6 Hz), 5.74(s, 1H), 6.74(d, 1H, J=8.1 Hz), 6.81(d, 1H, J=8.1 Hz), 8.05(br d, 1H, J=8.5 Hz), 8.54(m, 1H), 9.38(br s, 1H). | Melting Point 185 (° C.).<br>Elemental Analysis<br>as $C_{27}H_{28}N_4O_6$.1.6HCl.0.6$H_2O$<br>Calculated: C, 58.36; H, 5.22; Cl, 10.21; N, 10.08.<br>Found: C, 58.34; H, 5.39; Cl, 10.40; N, 9.86.<br>IR($cm^{-1}$) (KBr)<br>3346, 3174, 1644, 1611, 1506, 1466, 1433, 1381, 1338, 1278, 1178, 1116, 1052, 920, 835, 810, 746.<br>Mass (FAB) 487 ($(M+H)^+$). |
| Compound 22<br>Hydrochloride<br>Yield: 70(%) | NMR (ppm) (300 MHz, DMSO-$d_6$)<br>0.40–0.54(2H, m), 0.60–0.77(2H, m), 1.10(1H, m), 1.86–1.90 (1H, m), 2.32(1H, d, J=17.0 Hz), 2.60–2.82(2H, m), 2.94–3.06 | Melting Point >240 (dec) (° C.).<br>Elemental Analysis<br>as $C_{28}H_{29}N_3O_3$.194HCl.0.4$H_2O$ |

-continued

| | | |
|---|---|---|
| 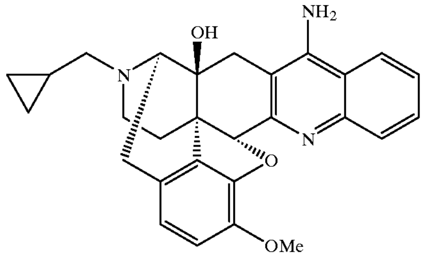 | (2H, m), 3.14–3.28(2H, m), 3.31–3.41(1H, m), 3.55–3.60(1H, m), 3.67(3H, s), 4.18–4.20(1H, m), 5.84(1H, s), 6.86(1H, d, J=8.5 Hz), 6.90(1H, d, J=8.5 Hz), 7.16(1H, br s), 7.62–7.67 (1H, m), 7.91–8.00(2H, m), 8.30–8.70(1H, br s), 8.43(1H, d, J=8.8 Hz), 9.30(1.7H, br s), 14.58(0.6H, br s). | Calculated: C, 63.04; H, 6.00; N, 7.88; Cl, 12.89.<br>Found: C, 63.07; H, 6.08; N, 7.88; Cl, 12.92.<br>IR($cm^{-1}$) (KBr)<br>3400, 1640, 1597, 1504, 1441, 1263, 1164, 1127, 1052, 913, 764.<br>Mass (FAB) 456 ($(M+H)^+$). |
| Compound 23<br>Methanesulfonate<br>Yield: 65(%) | NMR (ppm) (600 MHz, DMSO-$d_6$)<br>1.88–1.94(m, 1H), 2.33(s, 6H), 2.34(d, J=16.5 Hz, 1H), 2.64–2.67(m, 1H), 2.76–2.85(m, 1H), 2.93(d, J=16.5 Hz, 1H), 2.94–2.99(m, 3H), 3.15–3.24(m, 2H), 3.65(d, J=20.1 Hz, 1H), 3.71(s, 3H), 3.85–3.89(m, 1H), 5.85(br s, 1H), 6.66(br s, 1H), 6.88(d, J=8.2 Hz, 1H), 6.92(d, J=8.2 Hz, 1H), 7.66–7.71 (m, 1H), 7.95–8.01(m, 2H), 8.45(d, J=8.5 Hz, 1H), 8.46(br s, 1H), 9.23(br s, 1H), 9.35(br s, 1H), 14.2(br s, 1H). | Melting Point 245–250 (° C.).<br>Elemental Analysis<br>as $C_{25}H_{25}N_3O_3.2.0OCH_3SO_3H.0.65H_2O$<br>Calculated: C, 52.36; H, 5.58; N, 6.78; S, 10.35.<br>Found: C, 52.32; H, 5.59; N, 6.78; S, 10.53.<br>IR($cm^{-1}$) (KBr)<br>3450, 1657, 1611, 1597, 1508, 1456, 1286, 1265, 1201, 1060, 785.<br>Mass (FAB) 416 ($(M+H)^+$). |
| 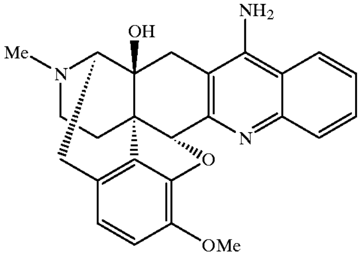 | | |
| Compound 24<br>Yield: 30(%) | NMR (ppm) (300 MHz, DMSO-$d_6$)<br>1.41–1.60(m, 1H), 2.05(s, 1.35H), 2.13(s, 1.65H), 2.23(d, J=16.2 Hz, 0.45H), 2.26(d, J=16.2 Hz, 0.55H), 2.24–2.36(m, 1H), 2.70(d, J=16.2 Hz, 0.45H), 2.74(d, J=16.2 Hz, 0.55H), 2.83(d, J=19.2 Hz, 0.45H), 2.98–3.15(m, 1H), 3.03(d, J=16.2 Hz, 0.55H), 3.17(dd, J=19.2, 6.9 Hz, 0.45H), 3.28(dd, J=19.2, 6.9 Hz, 0.55H), 3.63(s, 3H), 3.66–3.76(m, 0.45H), 4.14(d, J=6.9 Hz, 0.45H), 4.35–4.46(m, 0.55H), 4.98(s, 0.45H), 4.99 | IR($cm^{-1}$) (KBr)<br>3400; 1618, 1506, 1446, 1278, 1166, 1129, 1052, 909, |
| 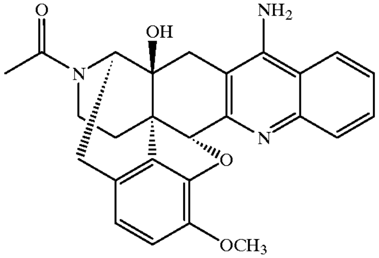 | | |
| Compound 54<br>Methanesulfonate<br>Yield: 42 (%) | NMR (ppm) (300 MHz, $CD_3OD$)<br>0.52 . 0.57 (2H, m), 0.74–0.91 (2H, m), 1.15 (1H, m), 2.01–2.06 (1H, m), 2.68 (3H, s), 2.77–2.88 (1H, m), 2.92–3.17 (4H, m), | Melting Point >230 (° C.)<br>Elemental Analysis<br>as $C_{28}H_{27}N_3O_4 \cdot CH_3SO_3H \cdot 0.8\ H_2O$ |

-continued

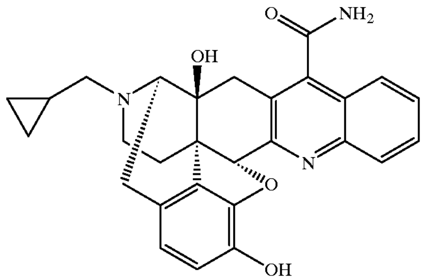

3.21–3.27 (1H, m), 3.32–3.34 (1H, m), 3.39–3.46 (1H, m), 3.53
(1H, d, J = 19.5 Hz), 4.27 (1H, d, J = 6.3 Hz), 5.71 (1H, s), 6.66
(1H, d, J = 8.2 Hz), 6.74 (1H, d, J = 8.2 Hz), 7.65–7.70 (1H, m),
7.80–7.85 (1H, m), 7.89–7.91 (1H, m), 8.13 (1H, d, J = 8.5 Hz).

IR ($cm^{-1}$) (KBr)
3400, 1665, 1504, 1462, 1330, 1197, 1060, 783, 774,
563, 536.

Mass (FAB) 470 ($(M + H)^+$).

Calculated: C, 60.05; H, 5.66; N, 7.24; S, 5.53.
Found: C, 60.00; H, 5.70; N, 7.17; S, 5.76.

Compound 55
Methanesulfonate
Yield: 23 (%)

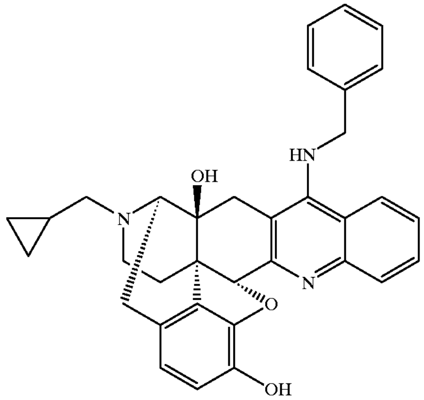

NMR (ppm) (300 MHz, DMSO-$d_6$)
0.41–0.55 (2H, m), 0.60–0.79 (2H, m), 1.07 (1H, m), 1.85–1.94
(1H, m), 2.35 (7H, s), 2.46–2.68 (2H, s), 2.72–2.85 (1H, m),
2.97–3.26 (4H, m), 3.33–3.42 (1H, m), 3.48–3.58 (1H, m), 4.04
(1H, br s), 4.16 (1H, d, J = 6.3 Hz), 4.92 (1H, d, J = 17.3 Hz),
5.08 (1H, d, J = 17.3 Hz), 5.77 (1H, s), 6.65 (1H, br s), 6.72
(1H, s), 6.72 (1H, s), 7.22–7.36 (5H, m), 7.48–7.55 (1H, m),
7.89–7.98 (2H, m), 8.14 (1H, m), 8.86 (1H, br s), 9.10 (1H, br
s), 9.54 (1H, br s).

IR ($cm^{-1}$) (KBr)
3300, 1638, 1578, 1535, 1510, 1460, 1421, 1330, 1199,
1044, 785, 774, 536.

Mass (FAB) 532 ($(M + H)^+$).

Melting Point 185–191 (° C.)

Elemental Analysis
as $C_{34}H_{33}N_3O_3 \cdot 2.4\ CH_3SO_3SO_3H \cdot 0.6\ H_2O$
Calculated: C, 56.55; H, 5.71; N, 5.44; S, 9.95.
Found: C, 56.72; H, 5.78; N, 5.41; S, 9.94.

-continued

| | | |
|---|---|---|
| Compound 56<br>Hydrochloride<br>Yield: 83 (%)<br>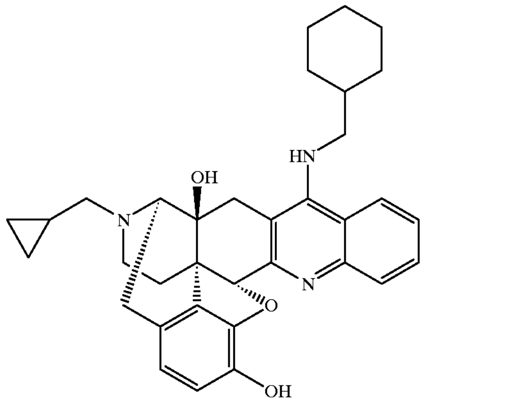<br>3.05–3.10 (2H, m), 3.25–3.50 (2H, m), 3.50–3.65 (2H, m), 3.79<br>Found: C, 65.92; H, 7.06; Cl, 10.97; N, 6.65.<br>(1H, dd, J = 14.1, 5.8 Hz), 6.81 (1H, d, J = 8.2 Hz), 7.60–7.67 (1H,<br>IR ($cm^{-1}$) (KBr)<br>6.74 (1H, d, J = 8.2 Hz), 6.81 (1H, d, J = 8.2 Hz), 7.60–7.67 (1H,<br>3400, 2932, 1634, 1609, 1576, 1526, 1508, 1460, 1359,<br>m[001b]), 7.93 (2H, d, J = 3.6 Hz), 8.36 (1H, d, J = 8.5 Hz).<br>Mass (FAB) 538 ($(M + H)^+$). | NMR (ppm) (300 MHz, $CD_3OD$)<br>0.50–0.60 (2H, m), 0.72–1.01 (4H, m), 1.05–1.30 (4H, m),<br>1.45–1.95 (7H, m), 2.00–2.08 (1H, m), 2.64 (1H, d, J = 16.5 Hz),<br>2.80 (1H, td, J = 13.5, 4.9 Hz), 3.00 (1H, d, J = 16.5 Hz),<br>Calculated: C, 65.91; H, 6.88; Cl, 10.87; N, 6.78.<br>1330, 1259, 1183, 1160, 1125, 1112, 1065, 1029, 926. | Melting Point >200 (dec) (° C.).<br>Elemental Analysis<br>as $C_{34}H_{39}N_3O_3 \cdot 1.9\ HCl \cdot 0.7\ H_2O$ |
| Compound 57<br>Hydrochloride<br>Yield: 53 (%)<br>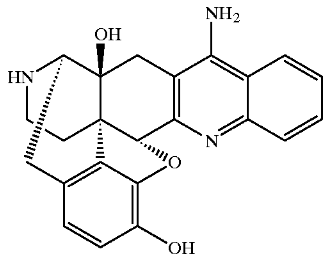<br>6.71–6.79 (2H, m), 7.62–7.69 (1H, m), 7.92–7.94 (2H, m),<br>Found: C, 56.76; H, 5.78; Cl, 14.86; N, 8.50.<br>8.31–8.34 (1H, m).<br>3400, 1651, 1502, 1468, 1431, 1375, 1319, 247, 1162,<br>1085, 1046, 925, 799, 762. | NMR (ppm) (300 MHz, $CD_3OD$)<br>1.96–2.02 (1H, m), 2.40–2.46 (1H, m), 2.75–2.82 (1H, m),<br>2.90–2.96 (1H, m), 3.01–3.15 (1H, m), 3.29–3.30 (2H, m),<br>3.43–3.52 (1H, m), 4.01 (1H, d, J = 6.0 Hz), 5.73 (1H, s),<br>Calculated: C, 57.03; H, 5.50; Cl, 14.48; N, 8.58.<br>IR ($cm^{-1}$) (KBr) | Melting Point >235 (dec) (° C.).<br>Elemental Analysis<br>as $C_{23}H_{21}N_3O_3 \cdot 2\ HCl \cdot 1.35\ H_2O \cdot 0.25\ CH_3OH$ |

-continued
Mass (FAB) 388 ((M + H)+).
| | | |
|---|---|---|
| Compound 58<br>Maleate<br>Yield: 10 (%)<br>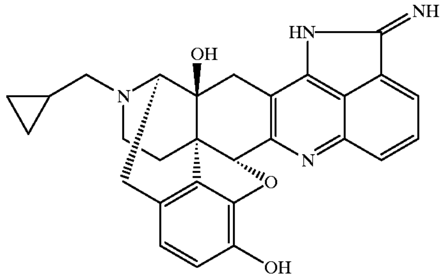<br>3.47 (1H, dd, J = 13.8, 7.5 Hz), 3.60 (1H, d, J = 20.1 Hz), 6.80 (1H, d, J = 6.3 Hz), 5.71 (1H, s), 6.74 (1H, d, J = 7.8 Hz), 6.80 (1H, d, J = 7.8 Hz), 7.92 (1H, dd, J = 8.4, 6.9 Hz), 8.20 (1H, d, J = 8.4 Hz), 8.21 (1H, d, J = 6.9 Hz). | NMR (ppm) (300 MHz, $CD_3OD$)<br>0.55–0.66 (2H, m), 0.80–0.99 (2H, m), 1.17–1.24 (1H, m), 2.03–2.08 (1H, m), 2.80–2.92 (2H, m), 2.86 (1H, d, J = 17.1 Hz), 3.03–3.15 (2H, m), 3.25–3.40 (2H, m), 3.36 (1H, d, J = 17.1 Hz),<br>Mass (FAB) 467 ((M + H)+). | Melting Point >190 (dec) (° C.).<br>IR ($cm^{-1}$) (KBr)<br>3300, 1470, 1357, 1280, 1251, 1176, 1116, 1067, 1033, |

Example 46

Infarction Inhibiting Action in Rat Model of Middle Cerebral Artery Ischemia

It is the well known fact that, in the acute stage of human cerebral infarction, significant cerebral edema is caused by cerebral ischemia accompanied with a grave lesion of the intracerebral blood vessels, and that when the blood flow is reopened in the acute stage of cerebral infarction, cerebral edema is significantly worsened. It is also known that, in this way, in the acute stage of cerebral infarction, the lesion proceeds to the peripheral tissue from the core of infarction, and death of the nerve cells is extended with the passage of several days. This possibly not only extends and makes grave aftereffects, and causes loss of motor and mental function, but also finally causes the critical influences on the life. As an in vivo experimental model of cerebral infarction which is capable of precisely evaluating the clinical effect of a medicine in conformity with clinical conditions of the disease of a patient of cerebral infarction, the middle cerebral artery occlusion (MCAo)-recirculation model comprising an embolus with a yarn using Wister rats is known [Document: Japan Journal of Stroke, vol. 8, 1 (1986)]. It is apparent that, in this model, a compound exhibiting the infarction inhibiting action is useful as an agent for curing or preventing worsening of cerebral stroke, traumatic cerebral diseases, cerebral edema, and cerebral neurodegenerative diseases. This action was evaluated by applying the MCAo model by the method which will be described below.

In rats of 10 weeks old, after etherization, a median incision of the cervical region was made up to the right carotid artery bifurcation under 1.0% halothane anesthetization with care to preserve the vagus nerves. The common carotid artery and the external carotid artery were separated from the periphery connective tissue with the right carotid artery bifurcation as the center, and each of the arteries was ligated by a 6-0 silk yarn (Eto yarn). Further, a yarn was wound on the internal carotid artery origin in preparation for ligation and fixing after insertion of the embolus. Next, the common carotid artery was incised, and the embolus was inserted from the common carotid artery to the internal carotid artery by about 15 to 16 mm, and ligated and fixed to the internal carotid artery by the silk yarn at the end thereof near the nylon yarn. In this operation, the end of the embolus was inserted into the anterior cerebral artery by about 1 to 2 mm beyond the middle cerebral artery bifurcation, and the inlet of the middle cerebral artery was occluded by the body (resin part) of the embolus for 1 hour. In recirculation, the embolus with a yarn was removed to recirculate the blood flow to the middle cerebral artery. 0.3 mg/kg or 3 mg/kg of each of test compounds was intraperitoneally administered 10 minutes before occlusion and 1 hour after recirculation of the blood flow. One day after occlusion and recirculation, the whole body was perfused with physiologic saline through the heart, and the brain was extracted. The extracted brain was cooled with ice and water for 5 minutes, and cut at intervals of 2.0 mm to form 7 sections of the cerebral coronal surface. Each of the sections was stained with TTC (Triphenyltetrazolium Chloride), and fixed by a 5% neutral buffer formalin solution. In each of the sections, the infarction area in the right cerebral hemisphere was measured by an image analyzer (Olympus), and the infarction was evaluated by volume ($mm^3$). The infarction volume was compared with the infarction volume of a control group to calculate the rate of inhibition of infarction. The results obtained are shown the table below.

TABLE

Action to inhibit infarction in rat model of middle cerebral atery ischemia

| | Rate of inhibition of infarction | |
|---|---|---|
| Compound | 0.3 mg/kg | 3 mg/kg |
| 1 | 19 | 60 |
| 2 | | 17 |
| 10 | 56 | 66 |
| 12 | | 25 |
| 13 | | 16 |
| 14 | 16 | 21 |
| 15 | | 13 |
| 16 | | 18 |
| 17 | 13 | 42 |
| 18 | | 39 |
| 19 | 22 | 32 |
| 20 | 31 | |
| 22 | | 60 |
| 25 | 32 | 50 |
| 26 | 41 | 55 |
| 34 | 58 | 65 |
| 36 | 62 | 89 |
| 37 | 55 | |
| 38 | 29 | |
| 39 | | 25 |
| 40 | 18 | |
| 41 | 20 | |
| 42 | | 35 |
| 44 | 12 | |

Industrial Applicability

It was made apparent that these compounds of the present invention have the action to protect the cerebral nerve cells from various damages caused by occurrence of cerebral ischemia to inhibit evolution of infarction, and the action to prevent worsening of disease conditions of cerebral infarction. Therefore, it was found that the compounds of the present invention are useful as agents for curing or preventing worsening of cerebral stroke, traumatic cerebral diseases, cerebral edema, and cerebral neurodegenerative diseases.

What is claimed is:

1. A quinolinomorphinan compound or pharmacologically acceptable acid addition salt thereof represented by the following formula (II):

(II)

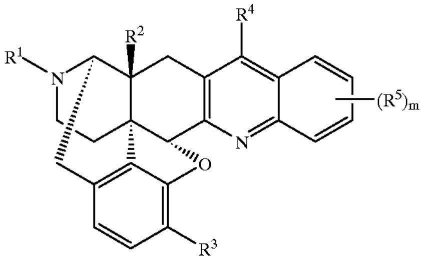

wherein $R^1$ is represents hydrogen, alkyl having 1 to 5 carbon atoms, cycloalkylalkyl having 4 to 7 carbon atoms, cycloalkenylalkyl having 5 to 7 carbon atoms, aryl having 6 to 12 carbon atoms, aralkyl having 7 to 13 carbon atoms, alkenyl having 2 to 7 carbon atoms, alkanoyl having 1 to 5 carbon atoms, furan-2-ylalkyl (wherein an alkyl moiety has 1 to 5 carbons atoms), or thiophene-2-ylalkyl (wherein an alkyl moiety has 1 to 5 carbon atoms);

$R^2$ and $R^3$ independently represent hydrogen, hydroxy, alkoxy having 1 to 5 carbon atoms, alkanoyloxy having 1 to 5 carbon atoms, aralkyloxy having 7 to 13 carbon atoms, or arylcarbonyloxy having 7 to 13 carbon atoms;

m represents an integer of 0 to 4;

$R^5$ is each of m substituents on the benzene ring, which independently represent $R^{18}$, or two $R^5$ substituted at adjacent carbons form together a fused ring structure A (wherein residual 0 to 2 substituents $R^5$ independently represent $R^{18}$ or another fused ring structure A);

the fused ring structure A is a benzo, indeno, naphtho, pyrido, or cycloalkeno having 5 to 7 carbon atoms, which is substituted by 0 to 4 substituents $R^9$, or unsubstituted dioxoleno;

$R^9$ and $R^{18}$ (1) independently represent fluoro, chloro, bromo, iodo, nitro, hydroxy, alkyl having 1 to 5 carbon atoms, alkoxy having 1 to 5 carbon atoms, isothiocyanato, trifluoromethyl, trifluoromethoxy, cyano, phenyl, hydroxyalkyl having 1 to 3 carbon atoms, $SR^6$, $SOR^6$, $SO_2R^6$, $(CH_2)_kCO_2R^7$, $SO_2NR^7R^8$, $CONR^7R^8$, $(CH_2)_kNR^7R^8$, or $(CH_2)_kN(R^7)COR^8$ (wherein k represents an integer of 0 to 5, $R^6$ represents alkyl having 1 to 5 carbon atoms, and $R^7$ and $R^8$ independently represent hydrogen, alkyl having 1 to 5 carbon atoms, or cycloalkylalkyl having 4 to 6 carbon atoms), and/or (2) $R^9$ and $R^{18}$ substituted at adjacent carbons with a ring junction therebetween form together any one of ethano, propano and o-benzeno bridged structures $R^9$—$R^{18}$;

$R^4$ represents hydrogen, alkyl having 1 to 5 carbon atoms, hydroxyalkyl having 1 to 5 carbon atoms, aryl having 6 to 12 carbon atoms (which may be substituted by at least one substituent $R^{17}$), $NR^{10}R^{11}$, $OR^{12}$ $COOR^{13}$ or $CONR^{14}R^{15}$, or any one of bridged structures $R^4$—$R^5$ of $N(R^{16})CO$, $N(R^{16})C({=}NH)$, $N(R^{16})CH_2$, o-benzeno, ethano, propano, and butano, which are formed together by $R^4$ and $R^5$ substituted at the peri position;

$R^{17}$ represents fluoro, chloro, bromo, iodo, nitro, amino, hydroxy, alkyl having 1 to 5 carbon atoms, alkoxy having 1 to 5 carbon atoms, alkanoyloxy having 1 to 5 carbon atoms, trifluoromethyl, trifluoromethoxy or cyano;

$R^{10}$, $R^{11}$, $R^{12}$ and $R^{16}$ independently represent hydrogen, alkyl having 1 to 5 carbon atoms, cycloalkylalkyl having 4 to 7 carbon atoms, aralkyl having 7 to 13 carbon atoms, or alkanoyl having 1 to 5 carbon atoms; and $R^{13}$, $R^{14}$ and $R^{15}$ independently represent hydrogen, alkyl having 1 to 5 carbon atoms, aryl having 6 to 12 carbon atoms, or aralkyl having 7 to 13 carbon atoms; (wherein when $R^4$ is hydrogen, and (1) when m is 1, $R^5$ is $R^{18}$ which represents hydroxy, and (2) when m is an integer of 2 to 4, $R^5$ is $R^{18}$ at least one of which represents hydroxy, or two $R^5$ form together a fused ring structure A, and the residual 0 to 2 $R^5$ independently represent $R^{18}$ (wherein when the fused ring structure A is benzo, pyrido, or cycloalkeno having 5 to 7 carbon atoms, at least one $R^{18}$ represents hydroxy, or at least one $R^9$ and one $R^{18}$ substituted at adjacent carbons with ring junction therebetween form together a bridged structure $R^9$—$R^{18}$ which is any one of ethano, propano and o-benzeno), or must form another fused ring structure A); and formula (II) includes (+) form, (−) form and (±) form.

2. A quinolinomorphinan compound or pharmacologically acceptable acid addition salt thereof according to claim 1, wherein $R^4$ is hydrogen, alkyl having 1 to 5 carbon atoms, or $NR^{10}R^{11}$, or $R^4$ and $R^5$ substituted at the peri position form together a bridged structure $R^4$—$R^5$ of $N(R^{16})CO$ or $N(R^{16})C({=}NH)$.

3. A quinolinomorphinan compound or pharmacologically acceptable acid addition salt thereof according to claim 1, wherein $R^4$ is hydroxyalkyl having 1 to 5 carbon atoms, aryl having 6 to 12 carbon atoms (which may be substituted by at least one substituent $R^{17}$), $OR^{12}$, $COOR^{13}$, or $CONR^{14}R^{15}$.

4. A quinolinomorphinan compound or pharmacologically acceptable acid addition salt thereof according to claim 2, wherein $R^5$ is each of m substituents on the benzene ring, which are independently $R^{18}$.

5. A quinolinomorphinan compound or pharmacologically acceptable acid addition salt thereof according to claim 2, wherein two $R^5$ groups substituted at adjacent carbons form together a fused ring structure A (the remaining 0 to 2 $R^5$ groups independently represent $R^{18}$ or form another fused ring structure A).

6. A quinolinomorphinan compound or pharmacologically acceptable acid addition salt thereof according to claim 3, wherein $R^5$ is each of m substituents on the benzene ring, which are independently $R^{18}$.

7. A quinolinomorphinan compound or pharmacologically acceptable acid addition salt thereof according to claim 4, wherein $R^4$ is hydrogen.

8. A quinolinomorphinan compound or pharmacologically acceptable acid addition salt thereof according to claim 4, wherein $R^4$ is alkyl having 1 to 5 carbon atoms.

9. A quinolinomorphinan compound or pharmacologically acceptable acid addition salt thereof according to claim 4, wherein $R^4$ is $NR^{10}R^{11}$.

10. A quinolinomorphinan compound or pharmacologically acceptable acid addition salt thereof according to claim 4, wherein $R^4$ and $R^5$ substituted at the peri position form together a bridged structure $R^4$—$R^5$ of $N(R^{16})CO$ or $N(R^{16})C({=}NH)$.

11. A quinolinomorphinan compound or pharmacologically acceptable acid addition salt thereof according to claim 5, wherein $R^4$ is hydrogen.

12. A quinolinomorphinan compound or pharmacologically acceptable acid addition salt thereof according to claim 5, wherein $R^4$ is $NR^{10}R^{11}$.

13. A quinolinomorphinan compound or pharmacologically acceptable acid addition salt thereof according to claim 9, wherein $R^{10}$ and $R^{11}$ are hydrogen.

14. A quinolinomorphinan compound or pharmacologically acceptable acid addition salt thereof according to claim 10, wherein $R^{16}$ is hydrogen.

15. A medical composition containing an effective amount of quinolinomorphinan compound or pharmacologically acceptable acid addition salt thereof represented by the following formula (II):

(II)

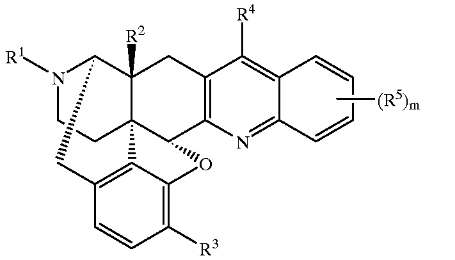

wherein $R^1$ is represents hydrogen, alkyl having 1 to 5 carbon atoms, cycloalkylalkyl having 4 to 7 carbon atoms, cycloalkenylalkyl having 5 to 7 carbon atoms, aryl having 6 to 12 carbon atoms, aralkyl having 7 to 13 carbon atoms, alkenyl having 2 to 7 carbon atoms, alkanoyl having 1 to 5 carbon atoms, furan-2-ylalkyl (wherein an alkyl moiety has 1 to 5 carbons atoms), or thiophene-2-ylalkyl (wherein an alkyl moiety has 1 to 5 carbon atoms);

$R^2$ and $R^3$ independently represent hydrogen, hydroxy, alkoxy having 1 to 5 carbon atoms, alkanoyloxy having 1 to 5 carbon atoms, aralkyloxy having 7 to 13 carbon atoms, or arylcarbonyloxy having 7 to 13 carbon atoms;

m represents an integer of 0 to 4;

$R^5$ is each of m substituents on the benzene ring, which independently represent $R^{18}$, or two $R^5$ substituted at adjacent carbons form together a fused ring structure A (wherein residual 0 to 2 substituents $R^5$ independently represent $R^{18}$ or another fused ring structure A);

the fused ring structure A is a benzo, indeno, naphtho, pyrido, or cycloalkeno having 5 to 7 carbon atoms, which is substituted by 0 to 4 substituents $R^9$, or unsubstituted dioxoleno;

$R^9$ and $R^{18}$ (1) independently represent fluoro, chloro, bromo, iodo, nitro, hydroxy, alkyl having 1 to 5 carbon atoms, alkoxy having 1 to 5 carbon atoms, isothiocyanato, trifluoromethyl, trifluoromethoxy, cyano, phenyl, hydroxyalkyl having 1 to 3 carbon atoms, $SR^6$, $SOR^6$, $SO_2R^6$, $(CH_2)_kCO_2R^7$, $SO_2NR^7R^8$, $CONR^7R^8$, $(CH_2)_kNR^7R^8$, or $(CH_2)_kN(R^7)COR^8$ (wherein k represents an integer of 0 to 5, $R^6$ represents alkyl having 1 to 5 carbon atoms, and $R^7$ and $R^8$ independently represent hydrogen, alkyl having 1 to 5 carbon atoms, or cycloalkylalkyl having 4 to 6 carbon atoms), and/or (2) $R^9$ and $R^{18}$ substituted at adjacent carbons with a ring junction therebetween form together any one of ethano, propano and o-benzeno bridged structures $R^9$—$R^{18}$ ;

$R^4$ represents hydrogen, alkyl having 1 to 5 carbon atoms, hydroxyalkyl having 1 to 5 carbon atoms, aryl having 6 to 12 carbon atoms (which may be substituted by at least one substituent $R^{17}$), $NR^{10}R^{11}$, $OR^{12}$ $COOR^{13}$ or $CONR^{14}R^{15}$, or any one of bridged structures $R^4$—$R^5$ of $N(R^{16})CO$, $N(R^{16})C(=NH)$, $N(R^{16})CH_2$, o-benzeno, ethano, propano, and butano, which are formed together by $R^4$ and $R^5$ substituted at the peri position;

$R^{17}$ represents fluoro, chloro, bromo, iodo, nitro, amino, hydroxy, alkyl having 1 to 5 carbon atoms, alkoxy having 1 to 5 carbon atoms, alkanoyloxy having 1 to 5 carbon atoms, trifluoromethyl, trifluoromethoxy or cyano;

$R^{10}$, $R^{11}$, $R^{12}$ and $R^{16}$ independently represent hydrogen, alkyl having 1 to 5 carbon atoms, cycloalkylalkyl having 4 to 7 carbon atoms, aralkyl having 7 to 13 carbon atoms, or alkanoyl having 1 to 5 carbon atoms; and $R^{13}$, $R^{14}$ and $R^{15}$ independently represent hydrogen, alkyl having 1 to 5 carbon atoms, aryl having 6 to 12 carbon atoms, or aralkyl having 7 to 13 carbon atoms; (wherein when $R^4$ is hydrogen, and (1) when m is 1, $R^5$ is $R^{18}$ which represents hydroxy, and (2) when m is an integer of 2 to 4, $R^5$ is $R^{18}$ at least one of which represents hydroxy, or two $R^5$ form together a fused ring structure A, and the residual 0 to 2 $R^5$ independently represent $R^{18}$ (wherein when the fused ring structure A is benzo, pyrido, or cycloalkeno having 5 to 7 carbon atoms, at least one $R^{18}$ represents hydroxy, or at least one $R^9$ and one $R^{18}$ substituted at adjacent carbons with a ring junction therebetween form together a bridged structure $R^9$—$R^{18}$ which is any one of ethano, propano and o-benzeno), or must form another fused ring structure A); and formula (II) includes (+), form (−) form and (±) form.

16. A method of curing or preventing worsening of cerebral disorder comprising administering an effective amount of a quinolinomorphinan compound or a pharmacologically acceptable acid addition salt thereof, which is represented by the following formula (I):

(I)

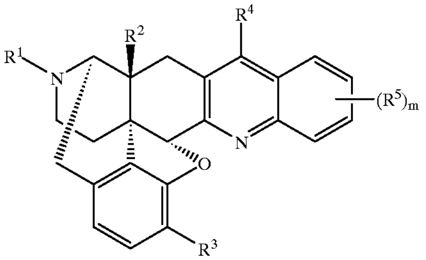

wherein $R^1$ represents hydrogen, alkyl having 1 to 5 carbon atoms, cycloalkylalkyl having 4 to 7 carbon atoms, cycloalkenylalkyl having 5 to 7 carbon atoms, aryl having 6 to 12 carbon atoms, aralkyl having 7 to 13 carbon atoms, alkenyl having 2 to 7 carbon atoms, alkanoyl having 1 to 5 carbon atoms, furan-2-ylalkyl (wherein an alkyl moiety has 1 to 5 carbon atoms), or thiophene-2-ylalkyl (wherein an alkyl moiety has 1 to 5 carbon atoms);

$R^2$ and $R^3$ independently represent hydrogen, hydroxy, alkoxy having 1 to 5 carbon atoms, alkanoyloxy having 1 to 5 carbon atoms, aralkyloxy having 7 to 13 carbon atoms, or arylcarbonyloxy having 7 to 13 carbon atoms;

m represents an integer of 0 to 4;

$R^5$ is each of m substituents on the benzene ring, which independently represent $R^{18}$, or two $R^5$ substituted at adjacent carbons form together a fused ring structure A (wherein residual 0 to 2 substituents $R^5$ independently represent $R^{18}$ or another fused ring structure A);

the fused ring structure A is a benzo, indeno, naphtho, pyrido, or cycloalkeno having 5 to 7 carbon atoms, which is substituted by 0 to 4 substituents $R^9$, or unsubstituted dioxoleno;

$R^9$ and $R^{18}$ (1) independently represent fluoro, chloro, bromo, iodo, nitro, hydroxy, alkyl having 1 to 5 carbon atoms, alkoxy having 1 to 5 carbon atoms, isothiocyanato, trifluoromethyl, trifluoromethoxy, cyano, phenyl, hydroxyalkyl having 1 to 3 carbon atoms, $SR^6$, $SOR^6$, $SO_2R^6$, $(CH_2)_kCO_2R^7$, $SO_2NR^7R^8$, $CONR^7R^8$, $(CH_2)_kNR^7R^8$, or $(CH_2)_kN(R^7)COR^8$ (wherein k represents an integer of 0 to 5, $R^6$ represents alkyl having 1 to 5 carbon atoms, and $R^7$ and $R^8$ independently represent hydrogen, alkyl having 1 to 5 carbon atoms, or cycloalkylalkyl having 4 to 6 carbon atoms), and/or (2) $R^9$ and $R^{18}$ substituted at adjacent carbons with a ring junction therebetween form together any one of ethano, propano and o-benzeno bridged structures $R^9$—$R^{18}$;

$R^4$ represents hydrogen, alkyl having 1 to 5 carbon atoms, hydroxyalkyl having 1 to 5 carbon atoms, aryl having 6 to 12 carbon atoms (which may be substituted by at least one substituent $R^{17}$), $NR^{10}R^{11}$, $OR^{12}$ $COOR^{13}$ or $CONR^{14}R^{15}$, or any one of bridged structures $R^4$—$R^5$ of $N(R^{16})CO$, $N(R^{16})C(=NH)$, $N(R^{16})CH_2$, o-benzeno, ethano, propano, and butano, which are formed together by $R^4$ and $R^5$ substituted at the peri position;

$R^{17}$ represents fluoro, chloro, bromo, iodo, nitro, amino, hydroxy, alkyl having 1 to 5 carbon atoms, alkoxy having 1 to 5 carbon atoms, alkanoyloxy having 1 to 5 carbon atoms, trifluoromethyl, trifluoromethoxy or cyano;

$R^{10}$, $R^{11}$, $R^{12}$ and $R^{16}$ independently represent hydrogen, alkyl having 1 to 5 carbon atoms, cycloalkylalkyl having 4 to 7 carbon atoms, aralkyl having 7 to 13 carbon atoms, or alkanoyl having 1 to 5 carbon atoms; and $R^{13}$, $R^{14}$ and $R^{15}$ independently represent hydrogen, alkyl having 1 to 5 carbon atoms, aryl having 6 to 12 carbon atoms, or aralkyl having 7 to 13 carbon atoms; and formula (I) includes (+) form, (−) form and (±) form.

17. A method of curing or preventing worsening of cerebral disorder according to claim 16, wherein $R^4$ is hydrogen, alkyl having 1 to 5 carbon atoms, or $NR^{10}R^{11}$, or $R^4$ and $R^5$ substituted at the peri position form together a bridged structure $R^4$—$R^5$ of $N(R^{16})CO$ or $N(R^{16})C(=NH)$.

18. A method of curing or preventing worsening of cerebral disorder according to claim 16, wherein $R^4$ is hydroxyalkyl having 1 to 5 carbon atoms, aryl having 6 to 12 carbon atoms (which may be substituted by at least one substituent $R^{17}$), $OR^{12}$, $COOR^{13}$, or $CONR^{14}R^{15}$.

19. A method of curing or preventing worsening of cerebral disorder according to claim 17, wherein $R^5$ is each of m substituents on the benzene ring, which are independently $R^{18}$.

20. A method of curing or preventing worsening of cerebral disorder according to claim 17, wherein two $R^5$ groups substituted at adjacent carbons form together a fused ring structure A (the remaining 0 to 2 $R^5$ groups independently represent $R^{18}$ or form another fused ring structure A).

21. A method of curing or preventing worsening of cerebral disorder according to claim 18, wherein $R^5$ is each of m substituents on the benzene ring, which are independently $R^{18}$.

22. A method of curing or preventing worsening of cerebral disorder according to claim 19, wherein $R^4$ is hydrogen.

23. A method of curing or preventing worsening of cerebral disorder according to claim 19, wherein $R^4$ is alkyl having 1 to 5 carbon atoms.

24. A method of curing or preventing worsening of cerebral disorder according to claim 19, wherein $R^4$ is $NR^{10}R^{11}$.

25. A method of curing or preventing worsening of cerebral disorder according to claim 19, wherein $R^4$ and $R^5$ substituted at the peri position form together a bridged structure $R^4$—$R^5$ of $N(R^{16})CO$ or $N(R^{16})C(=NH)$.

26. A method of curing or preventing worsening of cerebral disorder according to claim 20, wherein $R^4$ is hydrogen.

27. A method of curing or preventing worsening of cerebral disorder according to claim 20, wherein $R^4$ is $NR^{10}R^{11}$.

28. A method of curing or preventing worsening of cerebral disorder according to claim 24, wherein $R^{10}$ and $R^{11}$ are hydrogen.

29. A method of curing or preventing worsening of cerebral disorder according to claim 25, wherein $R^{16}$ is hydrogen.

* * * * *